United States Patent
Wang et al.

(10) Patent No.: US 12,004,838 B2
(45) Date of Patent: Jun. 11, 2024

(54) METHOD, APPARATUS, AND SYSTEM FOR WIRELESS VITAL MONITORING USING HIGH FREQUENCY SIGNALS

(71) Applicants: Fengyu Wang, Beijing (CN); Beibei Wang, Clarksville, MD (US); Xiaolu Zeng, Beijing (CN); Chenshu Wu, Hong Kong (CN); K. J. Ray Liu, Potomac, MD (US); Oscar Chi-Lim Au, San Jose, CA (US)

(72) Inventors: Fengyu Wang, Beijing (CN); Beibei Wang, Clarksville, MD (US); Xiaolu Zeng, Beijing (CN); Chenshu Wu, Hong Kong (CN); K. J. Ray Liu, Potomac, MD (US); Oscar Chi-Lim Au, San Jose, CA (US)

(73) Assignee: ORIGIN RESEARCH WIRELESS, INC., Rockville, MD (US)

( * ) Notice: Subject to any disclaimer, the term of this patent is extended or adjusted under 35 U.S.C. 154(b) by 0 days.

(21) Appl. No.: 17/945,995

(22) Filed: Sep. 15, 2022

(65) Prior Publication Data
US 2023/0081472 A1    Mar. 16, 2023

Related U.S. Application Data

(63) Continuation-in-part of application No. 16/790,610, filed on Feb. 13, 2020, now Pat. No. 11,928,894, and
(Continued)

(51) Int. Cl.
*A61B 5/00*    (2006.01)
*A61B 5/024*    (2006.01)
(Continued)

(52) U.S. Cl.
CPC .......... *A61B 5/0015* (2013.01); *A61B 5/0026* (2013.01); *A61B 5/02405* (2013.01);
(Continued)

(58) Field of Classification Search
CPC . A61B 5/0507; A61B 2503/22; A61B 5/0002; A61B 5/0015; A61B 5/002;
(Continued)

(56) References Cited

U.S. PATENT DOCUMENTS

| 2010/0152600 A1* | 6/2010 | Droitcour | ............. A61B 5/1113 600/534 |
| 2017/0032509 A1* | 2/2017 | Mannar | ..................... G06T 7/90 |

(Continued)

FOREIGN PATENT DOCUMENTS

| JP | 2004153559 | * | 5/2004 | .............. H04J 11/00 |

OTHER PUBLICATIONS

Liu et al., "Tracking Vital Signs During Sleep Leveraging Off-the-shelf WiFi", Jun. 2015, MobiHoc'15, pp. 267-276 (Year: 2015).*
(Continued)

*Primary Examiner* — Zhiyu Lu

(57) ABSTRACT

Methods, apparatus and systems for wireless vital sign monitoring are described. In one example, a described system comprises: a transmitter configured to transmit a wireless signal through a wireless channel of a venue; a receiver configured to receive the wireless signal through the wireless channel that is being impacted by an object motion of an object in the venue; and a processor. At least one of the transmitter or the receiver comprises an array of antennas used to transmit or receive the wireless signal. The object motion comprises at least one non-periodic body motion of the object and at least one periodic vital-sign motion of the object. The processor is configured for: segmenting space around the venue into a plurality of sectors based on a
(Continued)

beamforming and the received wireless signal, wherein each sector of the plurality of sectors is associated with a spatial direction relative to the array of antennas, obtaining a plurality of time series of channel information (CI) of the wireless channel based on the beamforming, wherein each time series of CI (TSCI) of the plurality of TSCI is associated with a respective sector of the plurality of sectors, isolating the object motion of the object in the plurality of TSCI to generate a plurality of isolated TSCI, compensating for the at least one non-periodic body motion of the object in the plurality of isolated TSCI to generate a plurality of compensated TSCI, and monitoring the at least one periodic vital-sign motion of the object based on the plurality of compensated TSCI.

20 Claims, 32 Drawing Sheets

Related U.S. Application Data a continuation-in-part of application No. 16/871,000, filed on May 10, 2020, now Pat. No. 11,500,056, and a continuation-in-part of application No. 16/871,004, filed on May 10, 2020, and a continuation-in-part of application No. 16/909,913, filed on Jun. 23, 2020, and a continuation-in-part of application No. 16/945,827, filed on Aug. 1, 2020, now Pat. No. 11,444,710, and a continuation-in-part of application No. 16/945,837, filed on Aug. 1, 2020, now Pat. No. 11,439,344, and a continuation-in-part of application No. 17/019,270, filed on Sep. 13, 2020, and a continuation-in-part of application No. 17/113,023, filed on Dec. 5, 2020, now Pat. No. 11,770,197, and a continuation-in-part of application No. 17/149,625, filed on Jan. 14, 2021, and a continuation-in-part of application No. 17/149,667, filed on Jan. 14, 2021, now abandoned, and a continuation-in-part of application No. 17/180,763, filed on Feb. 20, 2021, now Pat. No. 11,592,913, and a continuation-in-part of application No. 17/180,762, filed on Feb. 20, 2021, now Pat. No. 11,531,087, and a continuation-in-part of application No. 17/180,766, filed on Feb. 20, 2021, and a continuation-in-part of application No. 17/214,841, filed on Mar. 27, 2021, now Pat. No. 11,500,058, and a continuation-in-part of application No. 17/214,836, filed on Mar. 27, 2021, now Pat. No. 11,500,057, and a continuation-in-part of application No. 17/352,185, filed on Jun. 18, 2021, now Pat. No. 11,906,659, and a continuation-in-part of application No. 17/352,306, filed on Jun. 20, 2021, and a continuation-in-part of application No. 17/492,599, filed on Oct. 2, 2021, now Pat. No. 11,448,727, and a continuation-in-part of application No. 17/492,598, filed on Oct. 2, 2021, now Pat. No. 11,448,728, and a continuation-in-part of application No. 17/537,432, filed on Nov. 29, 2021, and a continuation-in-part of application No. 17/539,058, filed on Nov. 30, 2021, and a continuation-in-part of application No. 17/540,156, filed on Dec. 1, 2021, and a continuation-in-part of application No. 17/827,902, filed on May 30, 2022, and a continuation-in-part of application No. 17/492,642, filed on Oct. 3, 2021, now Pat. No. 11,639,981, and a continuation-in-part of application No. 17/838,228, filed on Jun. 12, 2022, and a continuation-in-part of application No. 17/838,231, filed on Jun. 12, 2022, and a continuation-in-part of application No. 17/838,244, filed on Jun. 12, 2022, and a continuation-in-part of application No. 17/888,429, filed on Aug. 15, 2022, now Pat. No. 11,771,366, and a continuation-in-part of application No. 17/891,037, filed on Aug. 18, 2022.

(60) Provisional application No. 63/253,083, filed on Oct. 6, 2021, provisional application No. 63/276,652, filed on Nov. 7, 2021, provisional application No. 63/281,043, filed on Nov. 18, 2021, provisional application No. 63/293,065, filed on Dec. 22, 2021, provisional application No. 63/308,927, filed on Feb. 10, 2022, provisional application No. 63/332,658, filed on Apr. 19, 2022, provisional application No. 63/349,082, filed on Jun. 4, 2022, provisional application No. 63/300,042, filed on Jan. 16, 2022, provisional application No. 63/354,184, filed on Jun. 21, 2022, provisional application No. 63/388,625, filed on Jul. 12, 2022.

(51) Int. Cl.
*A61B 5/0507* (2021.01)
*G01S 13/88* (2006.01)

(52) U.S. Cl.
CPC .......... *A61B 5/0507* (2013.01); *A61B 5/7207* (2013.01); *G01S 13/88* (2013.01)

(58) Field of Classification Search
CPC . A61B 5/0026; A61B 5/02405; A61B 5/0816; A61B 5/7207; A61B 5/7235; A61B 5/7253; G06F 21/32; G06F 2218/04; G06F 2218/10; G06F 2218/12; G06F 2221/2111; G06F 21/552; G01S 13/88; G10L 2025/783; G10L 25/18; G10L 25/30; G10L 25/78; G10L 25/90; H04W 4/027; H04W 4/029; H04W 4/021; H01Q 3/22; H04B 17/17; H04B 17/309
See application file for complete search history.

(56) References Cited

U.S. PATENT DOCUMENTS

2019/0384409 A1* 12/2019 Omer .................... G01S 13/003
2020/0107505 A1*  4/2020 Werner .................. G05B 15/02

OTHER PUBLICATIONS

Wu et al., "A Time-Reversal Paradigm for Indoor Positioning System", 2015, IEEE, vol. 60 No. 4, pp. 1331-1339 (Year: 2015).*
Ravichandran et al., "WiBreathe: Estimating Respiration Rate Using Wireless Signals in Natural Settings in the Home", 2015, IEEE, pp. 131-139 (Year: 2015).*

* cited by examiner

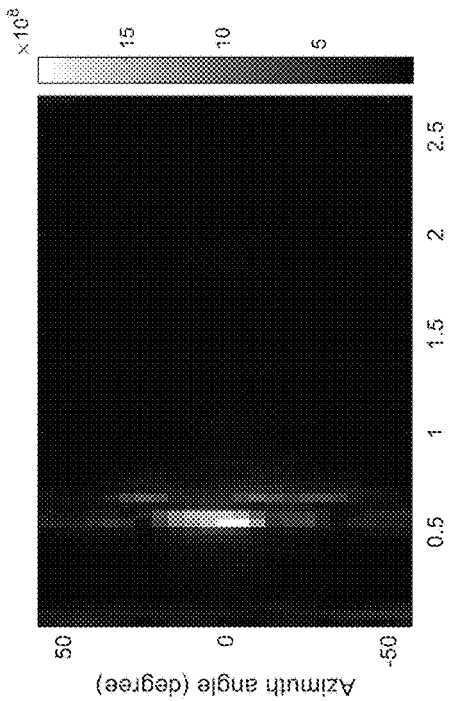
FIG. 4A
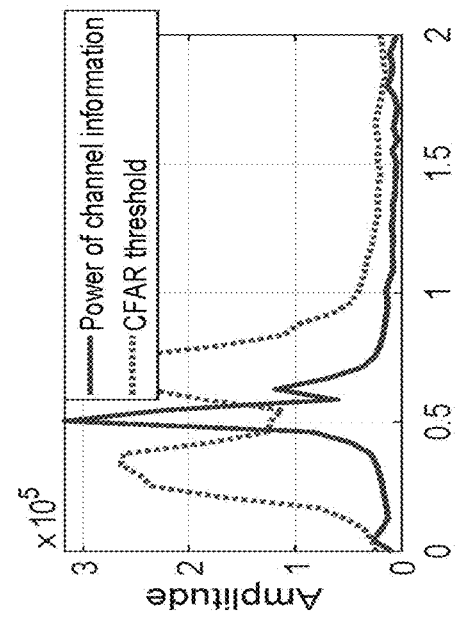
FIG. 4B
FIG. 4C
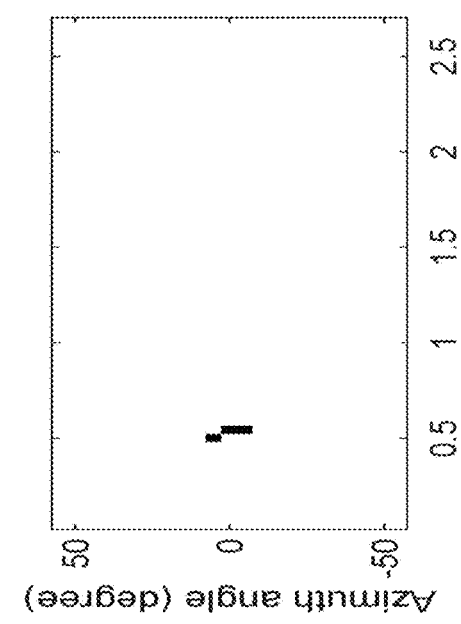
FIG. 4D

METHOD, APPARATUS, AND SYSTEM FOR WIRELESS VITAL MONITORING USING HIGH FREQUENCY SIGNALS

CROSS-REFERENCE TO RELATED APPLICATIONS

The present application hereby incorporates by reference the entirety of the disclosures of, and claims priority to, each of the following cases:

(a) U.S. patent application Ser. No. 16/790,610, entitled "METHOD, APPARATUS, AND SYSTEM FOR WIRELESS GAIT RECOGNITION", filed Feb. 13, 2020, (b) U.S. patent application Ser. No. 16/871,000, entitled "METHOD, APPARATUS, AND SYSTEM FOR WIRELESS TRACKING WITH GRAPH-BASED PARTICLE FILTERING", filed on May 10, 2020, (c) U.S. patent application Ser. No. 16/871,004, entitled "METHOD, APPARATUS, AND SYSTEM FOR PEOPLE COUNTING AND RECOGNITION BASED ON RHYTHMIC MOTION MONITORING", filed on May 10, 2020, (d) U.S. patent application Ser. No. 16/909,913, entitled "METHOD, APPARATUS, AND SYSTEM FOR IMPROVING TOPOLOGY OF WIRELESS SENSING SYSTEMS", filed on Jun. 23, 2020, (e) U.S. patent application Ser. No. 16/945,827, entitled "METHOD, APPARATUS, AND SYSTEM FOR PROCESSING AND PRESENTING LIFE LOG BASED ON A WIRELESS SIGNAL", filed on Aug. 1, 2020, (f) U.S. patent application Ser. No. 16/945,837, entitled "METHOD, APPARATUS, AND SYSTEM FOR WIRELESS SLEEP MONITORING", filed on Aug. 1, 2020, (g) U.S. patent application Ser. No. 17/019,270, entitled "METHOD, APPARATUS, AND SYSTEM FOR VEHICLE WIRELESS MONITORING", filed on Sep. 13, 2020, (h) U.S. patent application Ser. No. 17/113,023, entitled "METHOD, APPARATUS, AND SYSTEM FOR ACCURATE WIRELESS MONITORING", filed on Dec. 5, 2020, (i) U.S. patent application Ser. No. 17/492,642, entitled "METHOD, APPARATUS, AND SYSTEM FOR MOVEMENT TRACKING", filed on Oct. 3, 2021, (j) U.S. patent application Ser. No. 17/149,625, entitled "METHOD, APPARATUS, AND SYSTEM FOR WIRELESS MONITORING WITH MOTION LOCALIZATION", filed on Jan. 14, 2021, (k) U.S. patent application Ser. No. 17/149,667, entitled "METHOD, APPARATUS, AND SYSTEM FOR WIRELESS MONITORING WITH FLEXIBLE POWER SUPPLY", filed on Jan. 14, 2021, (l) U.S. patent application Ser. No. 17/180,763, entitled "METHOD, APPARATUS, AND SYSTEM FOR WIRELESS WRITING TRACKING", filed on Feb. 20, 2021, (m) U.S. patent application Ser. No. 17/180,762, entitled "METHOD, APPARATUS, AND SYSTEM FOR FALL-DOWN DETECTION BASED ON A WIRELESS SIGNAL", filed on Feb. 20, 2021, (n) U.S. patent application Ser. No. 17/180,766, entitled "METHOD, APPARATUS, AND SYSTEM FOR WIRELESS MOTION RECOGNITION", filed on Feb. 20, 2021, (o) U.S. patent application Ser. No. 17/214,841, entitled "METHOD, APPARATUS, AND SYSTEM FOR WIRELESS PROXIMITY SENSING", filed on Mar. 27, 2021, (p) U.S. patent application Ser. No. 17/214,836, entitled "METHOD, APPARATUS, AND SYSTEM FOR WIRELESSLY TRACKING KEYSTROKES", filed on Mar. 27, 2021, (q) U.S. patent application Ser. No. 17/352,185, entitled "METHOD, APPARATUS, AND SYSTEM FOR WIRELESS MICRO MOTION MONITORING", filed on Jun. 18, 2021, (r) U.S. patent application Ser. No. 17/352,306, entitled "METHOD, APPARATUS, AND SYSTEM FOR WIRELESS MONITORING TO ENSURE SECURITY", filed on Jun. 20, 2021, (s) U.S. Provisional Patent application 63/253,083, entitled "METHOD, APPARATUS, AND SYSTEM FOR WIRELESS SENSING, DETECTION AND TRACKING", filed on Oct. 6, 2021, (t) U.S. patent application Ser. No. 17/492,599, entitled "METHOD, APPARATUS, AND SYSTEM FOR HUMAN RECOGNITION BASED ON GAIT FEATURES", filed on Oct. 2, 2021, (u) U.S. patent application Ser. No. 17/492,598, entitled "METHOD, APPARATUS, AND SYSTEM FOR SOUND SENSING BASED ON WIRELESS SIGNALS", filed on Oct. 2, 2021, (v) U.S. Provisional Patent application 63/276,652, entitled "METHOD, APPARATUS, AND SYSTEM FOR WIRELESSLY MONITORING VITAL SIGN AND PERIODIC MOTIONS", filed on Nov. 7, 2021, (w) U.S. Provisional Patent application 63/281,043, entitled "METHOD, APPARATUS, AND SYSTEM FOR SENSING", filed on Nov. 18, 2021, (x) U.S. patent application Ser. No. 17/537,432, entitled "METHOD, APPARATUS, AND SYSTEM FOR AUTOMATIC AND ADAPTIVE WIRELESS MONITORING AND TRACKING", filed on Nov. 29, 2021, (y) U.S. patent application Ser. No. 17/539,058, entitled "METHOD, APPARATUS, AND SYSTEM FOR HUMAN IDENTIFICATION BASED ON HUMAN RADIO BIOMETRIC INFORMATION", filed on Nov. 30, 2021, (z) U.S. patent application Ser. No. 17/540,156, entitled "METHOD, APPARATUS, AND SYSTEM FOR POSITIONING AND POWERING A WIRELESS MONITORING SYSTEM", filed on Dec. 1, 2021, (aa) U.S. Provisional Patent application 63/293,065, entitled "METHOD, APPARATUS, AND SYSTEM FOR SPEECH ENHANCEMENT AND SEPARATION", filed on Dec. 22, 2021, (bb) U.S. Provisional Patent application 63/300,042, entitled "METHOD, APPARATUS, AND SYSTEM FOR WIRELESS SENSING AND SLEEP TRACKING", filed on Jan. 16, 2022, (cc) U.S. Provisional Patent application 63/308,927, entitled "METHOD, APPARATUS, AND SYSTEM FOR WIRELESS SENSING BASED ON MULTIPLE GROUPS OF WIRELESS DEVICES", filed on Feb. 10, 2022, (dd) U.S. Provisional Patent application 63/332,658, entitled "METHOD, APPARATUS, AND SYSTEM FOR WIRELESS SENSING", filed on Apr. 19, 2022, (ee) U.S. patent application Ser. No. 17/827,902, entitled "METHOD, APPARATUS, AND SYSTEM FOR SPEECH ENHANCEMENT AND SEPARATION BASED ON AUDIO AND RADIO SIGNALS", filed on May 30, 2022,
(ff) U.S. Provisional Patent application 63/349,082, entitled "METHOD, APPARATUS, AND SYSTEM FOR WIRELESS SENSING VOICE ACTIVITY DETECTION", filed on Jun. 4, 2022,
(gg) U.S. patent application Ser. No. 17/838,228, entitled "METHOD, APPARATUS, AND SYSTEM FOR WIRELESS SENSING BASED ON CHANNEL INFORMATION", filed on Jun. 12, 2022,
(hh) U.S. patent application Ser. No. 17/838,231, entitled "METHOD, APPARATUS, AND SYSTEM FOR IDENTIFYING AND QUALIFYING DEVICES FOR WIRELESS SENSING", filed on Jun. 12, 2022,
(ii) U.S. patent application Ser. No. 17/838,244, entitled "METHOD, APPARATUS, AND SYSTEM FOR WIRELESS SENSING BASED ON LINKWISE MOTION STATISTICS", filed on Jun. 12, 2022,
(jj) U.S. Provisional Patent application 63/354,184, entitled "METHOD, APPARATUS, AND SYSTEM FOR MOTION LOCALIZATION AND OUTLIER REMOVAL", filed on Jun. 21, 2022,
(kk) U.S. Provisional Patent application 63/388,625, entitled "METHOD, APPARATUS, AND SYSTEM FOR WIRELESS SENSING AND INDOOR LOCALIZATION", filed on Jul. 12, 2022,
(ll) U.S. patent application Ser. No. 17/888,429, entitled "METHOD, APPARATUS, AND SYSTEM FOR RADIO BASED SLEEP TRACKING", filed on Aug. 15, 2022,
(mm) U.S. patent application Ser. No. 17/891,037, entitled "METHOD, APPARATUS, AND SYSTEM FOR MAP RECONSTRUCTION BASED ON WIRELESS TRACKING", filed on Aug. 18, 2022.

TECHNICAL FIELD

The present teaching generally relates to wireless vital monitoring. More specifically, the present teaching relates to heartbeat tracking and monitoring by processing wireless channel information (CI) and beamforming.

BACKGROUND

Heart Rate Variability (HRV), defined as the variation of the periods between consecutive heartbeats, i.e., Inter-Beat Intervals (IBI), is an important indicator of the overall health status of an individual. Analysis of the HRV has been proved to be a powerful tool to assess cardiac health and evaluate the state of the Autonomic Nervous System (ANS). High-accuracy HRV monitoring is required in numerous applications such as early diagnose of cardiovascular disease, stress evaluation, emotions recognition and anxiety treatment, etc.

Traditional measurements of the HRV are obtained by continuously measuring the IBIs using the electrocardiogram (ECG) or photoplethysmogram (PPG) sensors, both of which are dedicated medical devices and have to be physically contacted with the human skin. However, using ECG or PPG is uncomfortable for users and sometimes may cause skin allergies. To avoid the direct contact with users' skin, other wearable devices such as Inertial Measurement Units (IMUs) have been explored to measure the movements of the chest surfaces to determine the IBIs and then measure the HRV. Although some of the aforementioned methods are less invasive than ECG and PPG-based approaches, all of them require users to wear dedicated devices, which is cumbersome and usually expensive for daily usage. Therefore, it is desirable to monitor the HRV in a non-contact and accurate way with a robust system.

As automobiles have become an essential part to facilitate people's daily life, Advanced Driver Assistance Systems (ADAS) have been gaining more and more interest in assisting drivers to enhance both safety and convenience. To respond timely in case of an emergency, ADAS needs to keep track of the driver's health/consciousness, which is generally achieved by monitoring the driver's vital signs including Respiration Rate (RR), Heart Rate (HR) and Heart Rate Variability (HRV). However, most of existing solutions requires an assumption that the human is stationary, which does not hold in practical driving scenarios.

SUMMARY

The present teaching generally relates to wireless vital monitoring. More specifically, the present teaching relates to heartbeat tracking and monitoring by processing wireless channel information (CI) and beamforming.

In one embodiment, a system for wireless monitoring is described. The system comprises: a transmitter configured for transmitting, using N1 transmit antennas, a first wireless signal through a wireless channel of a venue; a receiver configured for receiving, using N2 receive antennas, a second wireless signal through the wireless channel; and a processor. N1 and N2 are positive integers. The second wireless signal comprises a reflection of the first wireless signal by at least one living being having at least one repetitive motion in the venue. The processor is configured for: obtaining a plurality of time series of channel information (TSCI) of the wireless channel based on the second wireless signal, wherein each of the plurality of TSCI is associated with a respective transmit antenna of the transmitter and a respective receive antenna of the receiver; generating, for each living being of the at least one living being, a vital signal representing all repetitive motions of the living being based on the plurality of TSCI; extracting, from the vital signal of each living being, a heartbeat signal; and monitoring, for each living being in the venue, a heart rate variability based on the heartbeat signal.

In another embodiment, a wireless device of a wireless monitoring system is described. The wireless device comprises: a processor; a memory communicatively coupled to the processor; and a receiver communicatively coupled to the processor. An additional wireless device of the wireless monitoring system is configured for transmitting a first wireless signal through a wireless channel of a venue. The receiver is configured for receiving a second wireless signal through the wireless channel. The second wireless signal comprises a reflection of the first wireless signal by at least one living being having at least one repetitive motion in the venue. The processor is configured for: obtaining a time series of channel information (TSCI) of the wireless channel based on the second wireless signal; generating, for each living being of the at least one living being, a vital signal representing all repetitive motions of the living being based on the TSCI; extracting, from the vital signal of each living being, a heartbeat signal; and monitoring, for each living being in the venue, a heart rate variability based on the heartbeat signal.

In yet another embodiment, a method of a wireless monitoring system is described. The method comprises: transmitting a first wireless signal through a wireless channel of a venue; receiving a second wireless signal through the wireless channel, wherein the second wireless signal comprises a reflection of the first wireless signal by a plurality of human beings in the venue; obtaining a time series of channel information (TSCI) of the wireless channel based on the second wireless signal, wherein each CI comprises at least one of: a channel state information (CSI), a channel impulse response (CIR), channel frequency response (CFR), or received signal strength index (RSSI); generating, for each of the plurality of human beings, a vital signal representing all repetitive motions of the human being based on the TSCI; extracting, from the vital signal of each human being, a heartbeat signal; and simultaneously monitoring, for each of the plurality of human beings, a heart rate variability based on the heartbeat signal.

In a different embodiment, a system for vital sign monitoring based on wireless beamforming is described. The system comprises: a transmitter configured to transmit a wireless signal through a wireless channel of a venue; a receiver configured to receive the wireless signal through the wireless channel that is being impacted by an object motion of an object in the venue; and a processor. At least one of the transmitter or the receiver comprises an array of antennas used to transmit or receive the wireless signal. The object motion comprises at least one non-periodic body motion of the object and at least one periodic vital-sign motion of the object. The processor is configured for: segmenting space around the venue into a plurality of sectors based on a beamforming and the received wireless signal, wherein each sector of the plurality of sectors is associated with a spatial direction relative to the array of antennas, obtaining a plurality of time series of channel information (CI) of the wireless channel based on the beamforming, wherein each time series of CI (TSCI) of the plurality of TSCI is associated with a respective sector of the plurality of sectors, isolating the object motion of the object in the plurality of TSCI to generate a plurality of isolated TSCI, compensating for the at least one non-periodic body motion of the object in the plurality of isolated TSCI to generate a plurality of compensated TSCI, and monitoring the at least one periodic vital-sign motion of the object based on the plurality of compensated TSCI.

In another embodiment, a wireless device of a vital sign monitoring system is described. The wireless device comprises: a processor; a memory communicatively coupled to the processor; and a receiver communicatively coupled to the processor. An additional wireless device of the vital sign monitoring system is configured for transmitting a wireless signal through a wireless channel of a venue. The receiver is configured for receiving the wireless signal through the wireless channel that is being impacted by an object motion of an object in the venue. At least one of the transmitter or the receiver comprises an array of antennas used to transmit or receive the wireless signal. The object motion comprises at least one non-periodic body motion of the object and at least one periodic vital-sign motion of the object. The processor is configured for: segmenting space around the venue into a plurality of sectors based on a beamforming and the received wireless signal, wherein each sector of the plurality of sectors is associated with a spatial direction relative to the array of antennas, obtaining a plurality of time series of channel information (CI) of the wireless channel based on the beamforming, wherein each time series of CI (TSCI) of the plurality of TSCI is associated with a respective sector of the plurality of sectors, isolating the object motion of the object in the plurality of TSCI to generate a plurality of isolated TSCI, compensating for the at least one non-periodic body motion of the object in the plurality of isolated TSCI to generate a plurality of compensated TSCI, and monitoring the at least one periodic vital-sign motion of the object based on the plurality of compensated TSCI.

In yet another embodiment, a method of a vital sign monitoring system is described. The method comprises: transmitting, by a transmitter, a wireless signal through a wireless channel of a venue; receiving, by a receiver, the wireless signal through the wireless channel that is being impacted by an object motion of an object in the venue, wherein at least one of the transmitter or the receiver comprises an array of antennas used to transmit or receive the wireless signal, the object motion comprises at least one non-periodic body motion of the object and at least one periodic vital-sign motion of the object; segmenting space around the venue into a plurality of sectors based on a beamforming and the received wireless signal, wherein each sector of the plurality of sectors is associated with a spatial direction relative to the array of antennas; obtaining a plurality of time series of channel information (CI) of the wireless channel based on the beamforming, wherein each time series of CI (TSCI) of the plurality of TSCI is associated with a respective sector of the plurality of sectors; isolating the object motion of the object in the plurality of TSCI to generate a plurality of isolated TSCI; compensating for the at least one non-periodic body motion of the object in the plurality of isolated TSCI to generate a plurality of compensated TSCI; and monitoring the at least one periodic vital-sign motion of the object based on the plurality of compensated TSCI.

Other concepts relate to software for implementing the present teaching on wireless vital sign monitoring. Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF DRAWINGS

The methods, systems, and/or devices described herein are further described in terms of exemplary embodiments. These exemplary embodiments are described in detail with reference to the drawings. These embodiments are non-limiting exemplary embodiments, in which like reference numerals represent similar structures throughout the several views of the drawings.

FIGS. 4A-4D illustrate exemplary performances of a reflecting object detector, according to some embodiments of the present disclosure.

DETAILED DESCRIPTION

Figure 1A:
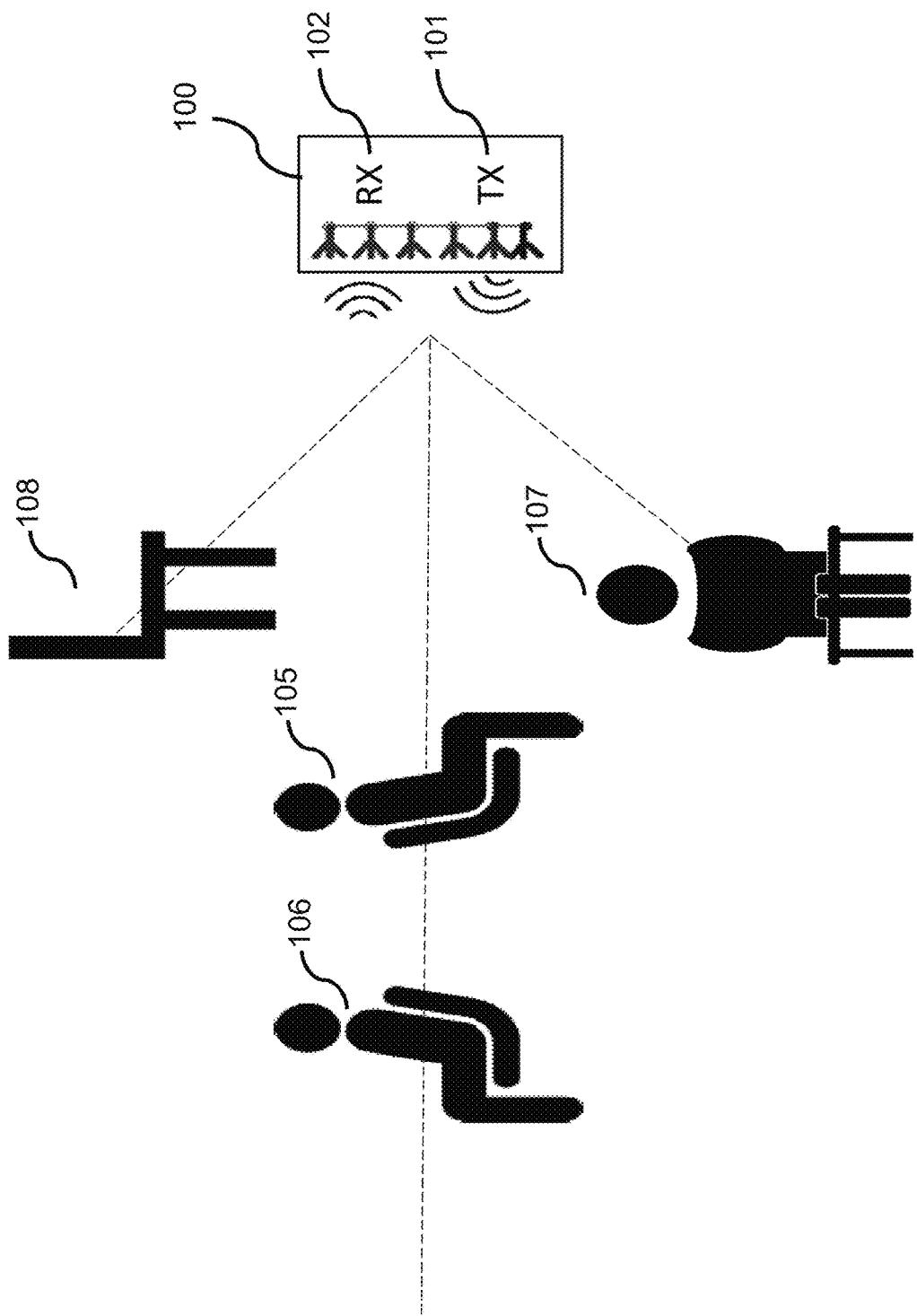
FIG. 1A illustrates an exemplary setup for a wireless vital monitoring system, according to some embodiments of the present disclosure.

In one embodiment, the present teaching discloses a method, apparatus, device, system, and/or software (method/apparatus/device/system/software) of a wireless monitoring system. A time series of channel information (CI) of a wireless multipath channel (channel) may be obtained (e.g. dynamically) using a processor, a memory communicatively coupled with the processor and a set of instructions stored in the memory. The time series of CI (TSCI) may be extracted from a wireless signal (signal) transmitted between a Type 1 heterogeneous wireless device (e.g. wireless transmitter, TX) and a Type 2 heterogeneous wireless device (e.g. wireless receiver, RX) in a venue through the channel. The channel may be impacted by an expression (e.g. motion, movement, expression, and/or change in position/pose/shape/expression) of an object in the venue. A characteristics and/or a spatial-temporal information (STI, e.g. motion information) of the object and/or of the motion of the object may be monitored based on the TSCI. A task may be performed based on the characteristics and/or STI. A presentation associated with the task may be generated in a user-interface (UI) on a device of a user. The TSCI may be a wireless signal stream. The TSCI or each CI may be preprocessed. A device may be a station (STA). The symbol "A/B" means "A and/or B" in the present teaching.

The expression may comprise placement, placement of moveable parts, location, position, orientation, identifiable place, region, spatial coordinate, presentation, state, static expression, size, length, width, height, angle, scale, shape, curve, surface, area, volume, pose, posture, manifestation, body language, dynamic expression, motion, motion sequence, gesture, extension, contraction, distortion, deformation, body expression (e.g. head, face, eye, mouth, tongue, hair, voice, neck, limbs, arm, hand, leg, foot, muscle, moveable parts), surface expression (e.g. shape, texture, material, color, electromagnetic (EM) characteristics, visual pattern, wetness, reflectance, translucency, flexibility), material property (e.g. living tissue, hair, fabric, metal, wood, leather, plastic, artificial material, solid, liquid, gas, temperature), movement, activity, behavior, change of expression, and/or some combination.

The wireless signal may comprise: transmitted/received signal, EM radiation, RF signal/transmission, signal in licensed/unlicensed/ISM band, bandlimited signal, baseband signal, wireless/mobile/cellular communication signal, wireless/mobile/cellular network signal, mesh signal, light signal/communication, downlink/uplink signal, unicast/multicast/broadcast signal, standard (e.g. WLAN, WWAN, WPAN, WBAN, international, national, industry, defacto, IEEE, IEEE 802, 802.11/15/16, WiFi, 802.11n/ac/ax/be, 3G/4G/LTF/5G/6G/7G18G, 3GPP, Bluetooth, BLE, Zigbee, RFID, UWB, WiMax) compliant signal, protocol signal, standard frame, beacon/pilot/probe/enquiry/acknowledgement/handshake/synchronization signal, management/control/data frame, management/control/data signal, standardized wireless/cellular communication protocol, reference signal, source signal, motion probe/detection/sensing signal, and/or series of signals. The wireless signal may comprise a line-of-sight (LOS), and/or a non-LOS component (or path/ link). Each CI may be extracted/generated/computed/sensed at a layer (e.g. PHY/MAC layer in OSI model) of Type 2 device and may be obtained by an application (e.g. software, firmware, driver, app, wireless monitoring software/system).

The wireless multipath channel may comprise: a communication channel, analog frequency channel (e.g. with analog carrier frequency near 700/800/900 MHz, 1.8/1.8/2.4/3/5/6/ 27/60 GHz), coded channel (e.g. in CDMA), and/or channel of a wireless network/system (e.g. WLAN, WiFi, mesh, LTE, 4G/5G, Bluetooth, Zigbee, UWB, RFID, microwave). It may comprise more than one channel. The channels may be consecutive (e.g. with adjacent/overlapping bands) or non-consecutive channels (e.g. non-overlapping WiFi channels, one at 2.4 GHz and one at 5 GHz).

The TSCI may be extracted from the wireless signal at a layer of the Type 2 device (e.g. a layer of OSI reference model, physical layer, data link layer, logical link control layer, media access control (MAC) layer, network layer, transport layer, session layer, presentation layer, application layer, TCP/IP layer, internet layer, link layer). The TSCI may be extracted from a derived signal (e.g. baseband signal, motion detection signal, motion sensing signal) derived from the wireless signal (e.g. RF signal). It may be (wireless) measurements sensed by the communication protocol (e.g. standardized protocol) using existing mechanism (e.g. wireless/cellular communication standard/network, 3G/LTE/4G/5G/6G/7G/8G, WiFi, IEEE 802.11/15/16). The derived signal may comprise a packet with at least one of: a preamble, a header and a payload (e.g. for data/control/ management in wireless links/networks). The TSCI may be extracted from a probe signal (e.g. training sequence, STF, LTF, L-STF, L-LTF, L-SIG, HE-STF, HE-LTF, HE-SIG-A, HE-SIG-B, CEF) in the packet. A motion detection/sensing signal may be recognized/identified base on the probe signal. The packet may be a standard-compliant protocol frame, management frame, control frame, data frame, sounding frame, excitation frame, illumination frame, null data frame, beacon frame, pilot frame, probe frame, request frame, response frame, association frame, reassociation frame, disassociation frame, authentication frame, action frame, report frame, poll frame, announcement frame, extension frame, enquiry frame, acknowledgement frame, RTS frame, CTS frame, QoS frame, CF-Poll frame, CF-Ack frame, block acknowledgement frame, reference frame, training frame, and/or synchronization frame.

The packet may comprise a control data and/or a motion detection probe. A data (e.g. ID/parameters/characteristics/ settings/control signal/command/instruction/notification/ broadcasting-related information of the Type 1 device) may be obtained from the payload. The wireless signal may be transmitted by the Type 1 device. It may be received by the Type 2 device. A database (e.g. in local server, hub device, cloud server, storage network) may be used to store the TSCI, characteristics, STI, signatures, patterns, behaviors, trends, parameters, analytics, output responses, identification information, user information, device information, channel information, venue (e.g. map, environmental model, network, proximity devices/networks) information, task information, class/category information, presentation (e.g. UI) information, and/or other information.

The Type 1/Type 2 device may comprise at least one of: electronics, circuitry, transmitter (TX)/receiver (RX)/transceiver, RF interface, "Origin Satellite"/"Tracker Bot", unicast/multicast/broadcasting device, wireless source device, source/destination device, wireless node, hub device, target device, motion detection device, sensor device, remote/ wireless sensor device, wireless communication device, wireless-enabled device, standard compliant device, and/or receiver. The Type 1 (or Type 2) device may be heterogeneous because, when there are more than one instances of Type 1 (or Type 2) device, they may have different circuitry, enclosure, structure, purpose, auxiliary functionality, chip/ IC, processor, memory, software, firmware, network connectivity, antenna, brand, model, appearance, form, shape, color, material, and/or specification. The Type 1/Type 2 device may comprise: access point, router, mesh router, internet-of-things (IoT) device, wireless terminal, one or more radio/RF subsystem/wireless interface (e.g. 2.4 GHz radio, 5 GHz radio, front haul radio, backhaul radio), modem, RF front end, RF/radio chip or integrated circuit (IC).

At least one of: Type 1 device, Type 2 device, a link between them, the object, the characteristics, the STI, the monitoring of the motion, and the task may be associated with an identification (ID) such as UUID. The Type 1/Type 2/another device may obtain/store/retrieve/access/preprocess/condition/process/analyze/monitor/apply the TSCI. The Type 1 and Type 2 devices may communicate network traffic in another channel (e.g. Ethernet, HDMI, USB, Bluetooth, BLE, WiFi, LTE, other network, the wireless multipath channel) in parallel to the wireless signal. The Type 2 device may passively observe/monitor/receive the wireless signal from the Type 1 device in the wireless multipath channel without establishing connection (e.g. association/ authentication) with, or requesting service from, the Type 1 device.

The transmitter (i.e. Type 1 device) may function as (play role of) receiver (i.e. Type 2 device) temporarily, sporadically, continuously, repeatedly, interchangeably, alternately, simultaneously, concurrently, and/or contemporaneously; and vice versa. A device may function as Type 1 device (transmitter) and/or Type 2 device (receiver) temporarily, sporadically, continuously, repeatedly, simultaneously, concurrently, and/or contemporaneously. There may be multiple wireless nodes each being Type 1 (TX) and/or Type 2 (RX) device. A TSCI may be obtained between every two nodes when they exchange/communicate wireless signals. The characteristics and/or STI of the object may be monitored individually based on a TSCI, or jointly based on two or more (e.g. all) TSCI.

The motion of the object may be monitored actively (in that Type 1 device, Type 2 device, or both, are wearable of/associated with the object) and/or passively (in that both Type 1 and Type 2 devices are not wearable of/associated with the object). It may be passive because the object may not be associated with the Type 1 device and/or the Type 2 device. The object (e.g. user, an automated guided vehicle or AGV) may not need to carry/install any wearables/fixtures (i.e. the Type 1 device and the Type 2 device are not wearable/attached devices that the object needs to carry in order perform the task). It may be active because the object may be associated with either the Type 1 device and/or the Type 2 device. The object may carry (or installed) a wearable/a fixture (e.g. the Type 1 device, the Type 2 device, a device communicatively coupled with either the Type 1 device or the Type 2 device).

The presentation may be visual, audio, image, video, animation, graphical presentation, text, etc. A computation of the task may be performed by a processor (or logic unit) of the Type 1 device, a processor (or logic unit) of an IC of the Type 1 device, a processor (or logic unit) of the Type 2 device, a processor of an IC of the Type 2 device, a local server, a cloud server, a data analysis subsystem, a signal analysis subsystem, and/or another processor. The task may be performed with/without reference to a wireless fingerprint or a baseline (e.g. collected, processed, computed, transmitted and/or stored in a training phase/survey/current survey/previous survey/recent survey/initial wireless survey, a passive fingerprint), a training, a profile, a trained profile, a static profile, a survey, an initial wireless survey, an initial setup, an installation, a re-training, an updating and a reset.

The Type 1 device (TX device) may comprise at least one heterogeneous wireless transmitter. The Type 2 device (RX device) may comprise at least one heterogeneous wireless receiver. The Type 1 device and the Type 2 device may be collocated. The Type 1 device and the Type 2 device may be the same device. Any device may have a data processing unit/apparatus, a computing unit/system, a network unit/system, a processor (e.g. logic unit), a memory communicatively coupled with the processor, and a set of instructions stored in the memory to be executed by the processor. Some processors, memories and sets of instructions may be coordinated.

There may be multiple Type 1 devices interacting (e.g. communicating, exchange signal/control/notification/other data) with the same Type 2 device (or multiple Type 2 devices), and/or there may be multiple Type 2 devices interacting with the same Type 1 device. The multiple Type 1 devices/Type 2 devices may be synchronized and/or asynchronous, with same/different window width/size and/or time shift, same/different synchronized start time, synchronized end time, etc. Wireless signals sent by the multiple Type 1 devices may be sporadic, temporary, continuous, repeated, synchronous, simultaneous, concurrent, and/or contemporaneous. The multiple Type 1 devices/Type 2 devices may operate independently and/or collaboratively. A Type 1 and/or Type 2 device may have/comprise/be heterogeneous hardware circuitry (e.g. a heterogeneous chip or a heterogeneous IC capable of generating/receiving the wireless signal, extracting CI from received signal, or making the CI available). They may be communicatively coupled to same or different servers (e.g. cloud server, edge server, local server, hub device).

Operation of one device may be based on operation, state, internal state, storage, processor, memory output, physical location, computing resources, network of another device. Difference devices may communicate directly, and/or via another device/server/hub device/cloud server. The devices may be associated with one or more users, with associated settings. The settings may be chosen once, pre-programmed, and/or changed (e.g. adjusted, varied, modified)/varied over time. There may be additional steps in the method. The steps and/or the additional steps of the method may be performed in the order shown or in another order. Any steps may be performed in parallel, iterated, or otherwise repeated or performed in another manner. A user may be human, adult, older adult, man, woman, juvenile, child, baby, pet, animal, creature, machine, computer module/software, etc.

In the case of one or multiple Type 1 devices interacting with one or multiple Type 2 devices, any processing (e.g. time domain, frequency domain) may be different for different devices. The processing may be based on locations, orientation, direction, roles, user-related characteristics, settings, configurations, available resources, available bandwidth, network connection, hardware, software, processor, co-processor, memory, battery life, available power, antennas, antenna types, directional/unidirectional characteristics of the antenna, power setting, and/or other parameters/characteristics of the devices.

The wireless receiver (e.g. Type 2 device) may receive the signal and/or another signal from the wireless transmitter (e.g. Type 1 device). The wireless receiver may receive another signal from another wireless transmitter (e.g. a second Type 1 device). The wireless transmitter may transmit the signal and/or another signal to another wireless receiver (e.g. a second Type 2 device). The wireless transmitter, wireless receiver, another wireless receiver and/or another wireless transmitter may be moving with the object and/or another object. The another object may be tracked.

The Type 1 and/or Type 2 device may be capable of wirelessly coupling with at least two Type 2 and/or Type 1 devices. The Type 1 device may be caused/controlled to switch/establish wireless coupling (e.g. association, authentication) from the Type 2 device to a second Type 2 device at another location in the venue. Similarly, the Type 2 device may be caused/controlled to switch/establish wireless coupling from the Type 1 device to a second Type 1 device at yet another location in the venue. The switching may be controlled by a server (or a hub device), the processor, the Type 1 device, the Type 2 device, and/or another device. The radio used before and after switching may be different. A second wireless signal (second signal) may be caused to be transmitted between the Type 1 device and the second Type 2 device (or between the Type 2 device and the second Type 1 device) through the channel. A second TSCI of the channel extracted from the second signal may be obtained. The second signal may be the first signal. The characteristics, STI and/or another quantity of the object may be monitored based on the second TSCI. The Type 1 device and the Type 2 device may be the same. The characteristics, STI and/or another quantity with different time stamps may form a waveform. The waveform may be displayed in the presentation.

The wireless signal and/or another signal may have data embedded. The wireless signal may be a series of probe signals (e.g. a repeated transmission of probe signals, a re-use of one or more probe signals). The probe signals may change/vary over time. A probe signal may be a standard compliant signal, protocol signal, standardized wireless protocol signal, control signal, data signal, wireless communication network signal, cellular network signal, WiFi signal, LTE/5G/6G/G signal, reference signal, beacon signal, motion detection signal, and/or motion sensing signal. A probe signal may be formatted according to a wireless network standard (e.g. WiFi), a cellular network standard (e.g. LTE/5G/6G), or another standard. A probe signal may comprise a packet with a header and a payload. A probe signal may have data embedded. The payload may comprise data. A probe signal may be replaced by a data signal. The probe signal may be embedded in a data signal. The wireless receiver, wireless transmitter, another wireless receiver and/or another wireless transmitter may be associated with at least one processor, memory communicatively coupled with respective processor, and/or respective set of instructions stored in the memory which when executed cause the processor to perform any and/or all steps needed to determine the STI (e.g. motion information), initial STI, initial time, direction, instantaneous location, instantaneous angle, and/or speed, of the object.

The processor, the memory and/or the set of instructions may be associated with the Type 1 device, one of the at least one Type 2 device, the object, a device associated with the object, another device associated with the venue, a cloud server, a hub device, and/or another server.

The Type 1 device may transmit the signal in a broadcasting manner to at least one Type 2 device(s) through the channel in the venue. The signal is transmitted without the Type 1 device establishing wireless connection (e.g. association, authentication) with any Type 2 device, and without any Type 2 device requesting services from the Type 1 device. The Type 1 device may transmit to a particular media access control (MAC) address common for more than one Type 2 devices. Each Type 2 device may adjust its MAC address to the particular MAC address. The particular MAC address may be associated with the venue. The association may be recorded in an association table of an Association Server (e.g. hub device). The venue may be identified by the Type 1 device, a Type 2 device and/or another device based on the particular MAC address, the series of probe signals, and/or the at least one TSCI extracted from the probe signals.

For example, a Type 2 device may be moved to a new location in the venue (e.g. from another venue). The Type 1 device may be newly set up in the venue such that the Type 1 and Type 2 devices are not aware of each other. During set up, the Type 1 device may be instructed/guided/caused/controlled (e.g. using dummy receiver, using hardware pin setting/connection, using stored setting, using local setting, using remote setting, using downloaded setting, using hub device, or using server) to send the series of probe signals to the particular MAC address. Upon power up, the Type 2 device may scan for probe signals according to a table of MAC addresses (e.g. stored in a designated source, server, hub device, cloud server) that may be used for broadcasting at different locations (e.g. different MAC address used for different venue such as house, office, enclosure, floor, multi-storey building, store, airport, mall, stadium, hall, station, subway, lot, area, zone, region, district, city, country, continent). When the Type 2 device detects the probe signals sent to the particular MAC address, the Type 2 device can use the table to identify the venue based on the MAC address.

A location of a Type 2 device in the venue may be computed based on the particular MAC address, the series of probe signals, and/or the at least one TSCI obtained by the Type 2 device from the probe signals. The computing may be performed by the Type 2 device.

The particular MAC address may be changed (e.g. adjusted, varied, modified) over time. It may be changed according to a time table, rule, policy, mode, condition, situation and/or change. The particular MAC address may be selected based on availability of the MAC address, a pre-selected list, collision pattern, traffic pattern, data traffic between the Type 1 device and another device, effective bandwidth, random selection, and/or a MAC address switching plan. The particular MAC address may be the MAC address of a second wireless device (e.g. a dummy receiver, or a receiver that serves as a dummy receiver).

The Type 1 device may transmit the probe signals in a channel selected from a set of channels. At least one CI of the selected channel may be obtained by a respective Type 2 device from the probe signal transmitted in the selected channel.

The selected channel may be changed (e.g. adjusted, varied, modified) over time. The change may be according to a time table, rule, policy, mode, condition, situation, and/or change. The selected channel may be selected based on availability of channels, random selection, a pre-selected list, co-channel interference, inter-channel interference, channel traffic pattern, data traffic between the Type 1 device and another device, effective bandwidth associated with channels, security criterion, channel switching plan, a criterion, a quality criterion, a signal quality condition, and/or consideration.

The particular MAC address and/or an information of the selected channel may be communicated between the Type 1 device and a server (e.g. hub device) through a network. The particular MAC address and/or the information of the selected channel may also be communicated between a Type 2 device and a server (e.g. hub device) through another network. The Type 2 device may communicate the particular MAC address and/or the information of the selected channel to another Type 2 device (e.g. via mesh network, Bluetooth, WiFi, NFC, ZigBee, etc.). The particular MAC address and/or selected channel may be chosen by a server (e.g. hub device). The particular MAC address and/or selected channel may be signaled in an announcement channel by the Type 1 device, the Type 2 device and/or a server (e.g. hub device). Before being communicated, any information may be pre-processed.

Wireless connection (e.g. association, authentication) between the Type 1 device and another wireless device may be established (e.g. using a signal handshake). The Type 1 device may send a first handshake signal (e.g. sounding frame, probe signal, request-to-send RTS) to the another device. The another device may reply by sending a second handshake signal (e.g. a command, or a clear-to-send CTS) to the Type 1 device, triggering the Type 1 device to transmit the signal (e.g. series of probe signals) in the broadcasting manner to multiple Type 2 devices without establishing connection with any Type 2 device. The second handshake signals may be a response or an acknowledge (e.g. ACK) to the first handshake signal. The second handshake signal may contain a data with information of the venue, and/or the Type 1 device. The another device may be a dummy device with a purpose (e.g. primary purpose, secondary purpose) to establish the wireless connection with the Type 1 device, to receive the first signal, and/or to send the second signal. The another device may be physically attached to the Type 1 device.

In another example, the another device may send a third handshake signal to the Type 1 device triggering the Type 1 device to broadcast the signal (e.g. series of probe signals) to multiple Type 2 devices without establishing connection (e.g. association, authentication) with any Type 2 device. The Type 1 device may reply to the third special signal by transmitting a fourth handshake signal to the another device. The another device may be used to trigger more than one Type 1 devices to broadcast. The triggering may be sequential, partially sequential, partially parallel, or fully parallel. The another device may have more than one wireless circuitries to trigger multiple transmitters in parallel. Parallel trigger may also be achieved using at least one yet another device to perform the triggering (similar to what as the another device does) in parallel to the another device. The another device may not communicate (or suspend communication) with the Type 1 device after establishing connection with the Type 1 device. Suspended communication may be resumed. The another device may enter an inactive mode, hibernation mode, sleep mode, stand-by mode, low-power mode, OFF mode and/or power-down mode, after establishing the connection with the Type 1 device. The another device may have the particular MAC address so that the Type 1 device sends the signal to the particular MAC address. The Type 1 device and/or the another device may be controlled and/or coordinated by a first processor associated with the Type 1 device, a second processor associated with the another device, a third processor associated with a designated source and/or a fourth processor associated with another device. The first and second processors may coordinate with each other.

A first series of probe signals may be transmitted by a first antenna of the Type 1 device to at least one first Type 2 device through a first channel in a first venue. A second series of probe signals may be transmitted by a second antenna of the Type 1 device to at least one second Type 2 device through a second channel in a second venue. The first series and the second series may/may not be different. The at least one first Type 2 device may/may not be different from the at least one second Type 2 device. The first and/or second series of probe signals may be broadcasted without connection (e.g. association, authentication) established between the Type 1 device and any Type 2 device. The first and second antennas may be same/different.

The two venues may have different sizes, shape, multipath characteristics. The first and second venues may overlap. The respective immediate areas around the first and second antennas may overlap. The first and second channels may be same/different. For example, the first one may be WiFi while the second may be LTE. Or, both may be WiFi, but the first one may be 2.4 GHz WiFi and the second may be 5 GHz WiFi. Or, both may be 2.4 GHz WiFi, but have different channel numbers, SSID names, and/or WiFi settings.

Each Type 2 device may obtain at least one TSCI from the respective series of probe signals, the CI being of the respective channel between the Type 2 device and the Type 1 device. Some first Type 2 device(s) and some second Type 2 device(s) may be the same. The first and second series of probe signals may be synchronous/asynchronous. A probe signal may be transmitted with data or replaced by a data signal. The first and second antennas may be the same.

The first series of probe signals may be transmitted at a first rate (e.g. 30 Hz). The second series of probe signals may be transmitted at a second rate (e.g. 200 Hz). The first and second rates may be same/different. The first and/or second rate may be changed (e.g. adjusted, varied, modified) over time. The change may be according to a time table, rule, policy, mode, condition, situation, and/or change. Any rate may be changed (e.g. adjusted, varied, modified) over time.

The first and/or second series of probe signals may be transmitted to a first MAC address and/or second MAC address respectively. The two MAC addresses may be same/different. The first series of probe signals may be transmitted in a first channel. The second series of probe signals may be transmitted in a second channel. The two channels may be same/different. The first or second MAC address, first or second channel may be changed over time. Any change may be according to a time table, rule, policy, mode, condition, situation, and/or change.

The Type 1 device and another device may be controlled and/or coordinated, physically attached, or may be of/in/of a common device. They may be controlled by/connected to a common data processor, or may be connected to a common bus interconnect/network/LAN/Bluetooth network/NFC network/BLE network/wired network/wireless network/mesh network/mobile network/cloud. They may share a common memory, or be associated with a common user, user device, profile, account, identity (ID), identifier, household, house, physical address, location, geographic coordinate, IP subnet, SSID, home device, office device, and/or manufacturing device.

Each Type 1 device may be a signal source of a set of respective Type 2 devices (i.e. it sends a respective signal (e.g. respective series of probe signals) to the set of respective Type 2 devices). Each respective Type 2 device chooses the Type 1 device from among all Type 1 devices as its signal source. Each Type 2 device may choose asynchronously. At least one TSCI may be obtained by each respective Type 2 device from the respective series of probe signals from the Type 1 device, the CI being of the channel between the Type 2 device and the Type 1 device.

The respective Type 2 device chooses the Type 1 device from among all Type 1 devices as its signal source based on identity (ID) or identifier of Type 1/Type 2 device, task to be performed, past signal source, history (e.g. of past signal source, Type 1 device, another Type 1 device, respective Type 2 receiver, and/or another Type 2 receiver), threshold for switching signal source, and/or information of a user, account, access info, parameter, characteristics, and/or signal strength (e.g. associated with the Type 1 device and/or the respective Type 2 receiver).

Initially, the Type 1 device may be signal source of a set of initial respective Type 2 devices (i.e. the Type 1 device sends a respective signal (series of probe signals) to the set of initial respective Type 2 devices) at an initial time. Each initial respective Type 2 device chooses the Type 1 device from among all Type 1 devices as its signal source.

The signal source (Type 1 device) of a particular Type 2 device may be changed (e.g. adjusted, varied, modified) when (1) time interval between two adjacent probe signals (e.g. between current probe signal and immediate past probe signal, or between next probe signal and current probe signal) received from current signal source of the Type 2 device exceeds a first threshold; (2) signal strength associated with current signal source of the Type 2 device is below a second threshold; (3) a processed signal strength associated with current signal source of the Type 2 device is below a third threshold, the signal strength processed with low pass filter, band pass filter, median filter, moving average filter, weighted averaging filter, linear filter and/or non-linear filter; and/or (4) signal strength (or processed signal strength) associated with current signal source of the Type 2 device is below a fourth threshold for a significant percentage of a recent time window (e.g. 70%, 80%, 90%). The percentage may exceed a fifth threshold. The first, second, third, fourth and/or fifth thresholds may be time varying.

Condition (1) may occur when the Type 1 device and the Type 2 device become progressively far away from each other, such that some probe signal from the Type 1 device becomes too weak and is not received by the Type 2 device. Conditions (2)-(4) may occur when the two devices become far from each other such that the signal strength becomes very weak.

The signal source of the Type 2 device may not change if other Type 1 devices have signal strength weaker than a factor (e.g. 1, 1.1, 1.2, or 1.5) of the current signal source.

If the signal source is changed (e.g. adjusted, varied, modified), the new signal source may take effect at a near future time (e.g. the respective next time). The new signal source may be the Type 1 device with strongest signal strength, and/or processed signal strength. The current and new signal source may be same/different.

A list of available Type 1 devices may be initialized and maintained by each Type 2 device. The list may be updated by examining signal strength and/or processed signal strength associated with the respective set of Type 1 devices. A Type 2 device may choose between a first series of probe signals from a first Type 1 device and a second series of probe signals from a second Type 1 device based on: respective probe signal rate, MAC addresses, channels, characteristics/properties/states, task to be performed by the Type 2 device, signal strength of first and second series, and/or another consideration.

The series of probe signals may be transmitted at a regular rate (e.g. 100 Hz). The series of probe signals may be scheduled at a regular interval (e.g. $0.01s$ for 100 Hz), but each probe signal may experience small time perturbation, perhaps due to timing requirement, timing control, network control, handshaking, message passing, collision avoidance, carrier sensing, congestion, availability of resources, and/or another consideration.

The rate may be changed (e.g. adjusted, varied, modified). The change may be according to a time table (e.g. changed once every hour), rule, policy, mode, condition and/or change (e.g. changed whenever some event occur). For example, the rate may normally be 100 Hz, but changed to 1000 Hz in demanding situations, and to 1 Hz in low power/standby situation. The probe signals may be sent in burst.

The probe signal rate may change based on a task performed by the Type 1 device or Type 2 device (e.g. a task may need 100 Hz normally and 1000 Hz momentarily for 20 seconds). In one example, the transmitters (Type 1 devices), receivers (Type 2 device), and associated tasks may be associated adaptively (and/or dynamically) to classes (e.g. classes that are: low-priority, high-priority, emergency, critical, regular, privileged, non-subscription, subscription, paying, and/or non-paying). A rate (of a transmitter) may be adjusted for the sake of some class (e.g. high priority class). When the need of that class changes, the rate may be changed (e.g. adjusted, varied, modified). When a receiver has critically low power, the rate may be reduced to reduce power consumption of the receiver to respond to the probe signals. In one example, probe signals may be used to transfer power wirelessly to a receiver (Type 2 device), and the rate may be adjusted to control the amount of power transferred to the receiver.

The rate may be changed by (or based on): a server (e.g. hub device), the Type 1 device and/or the Type 2 device. Control signals may be communicated between them. The server may monitor, track, forecast and/or anticipate the needs of the Type 2 device and/or the tasks performed by the Type 2 device, and may control the Type 1 device to change the rate. The server may make scheduled changes to the rate according to a time table. The server may detect an emergency situation and change the rate immediately. The server may detect a developing condition and adjust the rate gradually.

The characteristics and/or STI (e.g. motion information) may be monitored individually based on a TSCI associated with a particular Type 1 device and a particular Type 2 device, and/or monitored jointly based on any TSCI associated with the particular Type 1 device and any Type 2 device, and/or monitored jointly based on any TSCI associated with the particular Type 2 device and any Type 1 device, and/or monitored globally based on any TSCI associated with any Type 1 device and any Type 2 device. Any joint monitoring may be associated with: a user, user account, profile, household, map of venue, environmental model of the venue, and/or user history, etc.

A first channel between a Type 1 device and a Type 2 device may be different from a second channel between another Type 1 device and another Type 2 device. The two channels may be associated with different frequency bands, bandwidth, carrier frequency, modulation, wireless standards, coding, encryption, payload characteristics, networks, network ID, SSID, network characteristics, network settings, and/or network parameters, etc.

The two channels may be associated with different kinds of wireless system (e.g. two of the following: WiFi, LTE, LTE-A, LTE-U, 2.5G, 3G, 3.5G, 4G, beyond 4G, 5G, 6G, 7G, a cellular network standard, UMTS, 3GPP, GSM, EDGE, TDMA, FDMA, CDMA, WCDMA, TD-SCDMA, 802.11 system, 802.15 system, 802.16 system, mesh network, Zigbee, NFC, WiMax, Bluetooth, BLE, RFID, UWB, microwave system, radar like system). For example, one is WiFi and the other is LTE.

The two channels may be associated with similar kinds of wireless system, but in different network. For example, the first channel may be associated with a WiFi network named "Pizza and Pizza" in the 2.4 GHz band with a bandwidth of 20 MHz while the second may be associated with a WiFi network with SSID of "StarBud hotspot" in the 5 GHz band with a bandwidth of 40 MHz. The two channels may be different channels in same network (e.g. the "StarBud hotspot" network).

In one embodiment, a wireless monitoring system may comprise training a classifier of multiple events in a venue based on training TSCI associated with the multiple events. A CI or TSCI associated with an event may be considered/ may comprise a wireless sample/characteristics/fingerprint associated with the event (and/or the venue, the environment, the object, the motion of the object, a state/emotional state/mental state/condition/stage/gesture/gait/action/movement/activity/daily activity/history/event of the object, etc.).

For each of the multiple known events happening in the venue in a respective training (e.g. surveying, wireless survey, initial wireless survey) time period associated with the known event, a respective training wireless signal (e.g. a respective series of training probe signals) may be transmitted by an antenna of a first Type 1 heterogeneous wireless device using a processor, a memory and a set of instructions of the first Type 1 device to at least one first Type 2 heterogeneous wireless device through a wireless multipath channel in the venue in the respective training time period.

At least one respective time series of training CI (training TSCI) may be obtained asynchronously by each of the at least one first Type 2 device from the (respective) training signal. The CI may be CI of the channel between the first Type 2 device and the first Type 1 device in the training time period associated with the known event. The at least one training TSCI may be preprocessed. The training may be a wireless survey (e.g. during installation of Type 1 device and/or Type 2 device).

For a current event happening in the venue in a current time period, a current wireless signal (e.g. a series of current probe signals) may be transmitted by an antenna of a second Type 1 heterogeneous wireless device using a processor, a memory and a set of instructions of the second Type 1 device to at least one second Type 2 heterogeneous wireless device through the channel in the venue in the current time period associated with the current event.

At least one time series of current CI (current TSCI) may be obtained asynchronously by each of the at least one second Type 2 device from the current signal (e.g. the series of current probe signals). The CI may be CI of the channel between the second Type 2 device and the second Type 1 device in the current time period associated with the current event. The at least one current TSCI may be preprocessed.

The classifier may be applied to classify at least one current TSCI obtained from the series of current probe signals by the at least one second Type 2 device, to classify at least one portion of a particular current TSCI, and/or to classify a combination of the at least one portion of the particular current TSCI and another portion of another TSCI. The classifier may partition TSCI (or the characteristics/STI or other analytics or output responses) into clusters and associate the clusters to specific events/objects/subjects/locations/movements/activities. Labels/tags may be generated for the clusters. The clusters may be stored and retrieved. The classifier may be applied to associate the current TSCI (or characteristics/STI or the other analytics/output response, perhaps associated with a current event) with: a cluster, a known/specific event, a class/category/group/grouping/list/cluster/set of known events/subjects/locations/movements/activities, an unknown event, a class/category/group/grouping/list/cluster/set of unknown events/subjects/locations/movements/activities, and/or another event/subject/location/movement/activity/class/category/group/grouping/list/cluster/set. Each TSCI may comprise at least one CI each associated with a respective timestamp. Two TSCI associated with two Type 2 devices may be different with different: starting time, duration, stopping time, amount of CI, sampling frequency, sampling period. Their CI may have different features. The first and second Type 1 devices may be at same location in the venue. They may be the same device. The at least one second Type 2 device (or their locations) may be a permutation of the at least one first Type 2 device (or their locations). A particular second Type 2 device and a particular first Type 2 device may be the same device.

A subset of the first Type 2 device and a subset of the second Type 2 device may be the same. The at least one second Type 2 device and/or a subset of the at least one second Type 2 device may be a subset of the at least one first Type 2 device. The at least one first Type 2 device and/or a subset of the at least one first Type 2 device may be a permutation of a subset of the at least one second Type 2 device. The at least one second Type 2 device and/or a subset of the at least one second Type 2 device may be a permutation of a subset of the at least one first Type 2 device. The at least one second Type 2 device and/or a subset of the at least one second Type 2 device may be at same respective location as a subset of the at least one first Type 2 device. The at least one first Type 2 device and/or a subset of the at least one first Type 2 device may be at same respective location as a subset of the at least one second Type 2 device.

The antenna of the Type 1 device and the antenna of the second Type 1 device may be at same location in the venue. Antenna(s) of the at least one second Type 2 device and/or antenna(s) of a subset of the at least one second Type 2 device may be at same respective location as respective antenna(s) of a subset of the at least one first Type 2 device. Antenna(s) of the at least one first Type 2 device and/or antenna(s) of a subset of the at least one first Type 2 device may be at same respective location(s) as respective antenna(s) of a subset of the at least one second Type 2 device.

A first section of a first time duration of the first TSCI and a second section of a second time duration of the second section of the second TSCI may be aligned. A map between items of the first section and items of the second section may be computed. The first section may comprise a first segment (e.g. subset) of the first TSCI with a first starting/ending time, and/or another segment (e.g. subset) of a processed first TSCI. The processed first TSCI may be the first TSCI processed by a first operation. The second section may comprise a second segment (e.g. subset) of the second TSCI with a second starting time and a second ending time, and another segment (e.g. subset) of a processed second TSCI. The processed second TSCI may be the second TSCI processed by a second operation. The first operation and/or the second operation may comprise: subsampling, re-sampling, interpolation, filtering, transformation, feature extraction, pre-processing, and/or another operation.

A first item of the first section may be mapped to a second item of the second section. The first item of the first section may also be mapped to another item of the second section. Another item of the first section may also be mapped to the second item of the second section. The mapping may be one-to-one, one-to-many, many-to-one, many-to-many. At least one function of at least one of: the first item of the first section of the first TSCI, another item of the first TSCI, timestamp of the first item, time difference of the first item, time differential of the first item, neighboring timestamp of the first item, another timestamp associated with the first item, the second item of the second section of the second TSCI, another item of the second TSCI, timestamp of the second item, time difference of the second item, time differential of the second item, neighboring timestamp of the second item, and another timestamp associated with the second item, may satisfy at least one constraint.

One constraint may be that a difference between the timestamp of the first item and the timestamp of the second item may be upper-bounded by an adaptive (and/or dynamically adjusted) upper threshold and lower-bounded by an adaptive lower threshold.

The first section may be the entire first TSCI. The second section may be the entire second TSCI. The first time duration may be equal to the second time duration. A section of a time duration of a TSCI may be determined adaptively (and/or dynamically). A tentative section of the TSCI may be computed. A starting time and an ending time of a section (e.g. the tentative section, the section) may be determined. The section may be determined by removing a beginning portion and an ending portion of the tentative section. A beginning portion of a tentative section may be determined as follows. Iteratively, items of the tentative section with increasing timestamp may be considered as a current item, one item at a time.

In each iteration, at least one activity measure/index may be computed and/or considered. The at least one activity measure may be associated with at least one of: the current item associated with a current timestamp, past items of the tentative section with timestamps not larger than the current timestamp, and/or future items of the tentative section with timestamps not smaller than the current timestamp. The current item may be added to the beginning portion of the tentative section if at least one criterion (e.g. quality criterion, signal quality condition) associated with the at least one activity measure is satisfied.

The at least one criterion associated with the activity measure may comprise at least one of: (a) the activity measure is smaller than an adaptive (e.g. dynamically adjusted) upper threshold, (b) the activity measure is larger than an adaptive lower threshold, (c) the activity measure is smaller than an adaptive upper threshold consecutively for at least a predetermined amount of consecutive timestamps, (d) the activity measure is larger than an adaptive lower threshold consecutively for at least another predetermined amount of consecutive timestamps, (e) the activity measure is smaller than an adaptive upper threshold consecutively for at least a predetermined percentage of the predetermined amount of consecutive timestamps, (f) the activity measure is larger than an adaptive lower threshold consecutively for at least another predetermined percentage of the another predetermined amount of consecutive timestamps, (g) another activity measure associated with another timestamp associated with the current timestamp is smaller than another adaptive upper threshold and larger than another adaptive lower threshold, (h) at least one activity measure associated with at least one respective timestamp associated with the current timestamp is smaller than respective upper threshold and larger than respective lower threshold, (i) percentage of timestamps with associated activity measure smaller than respective upper threshold and larger than respective lower threshold in a set of timestamps associated with the current timestamp exceeds a threshold, and (j) another criterion (e.g. a quality criterion, signal quality condition).

An activity measure/index associated with an item at time T1 may comprise at least one of: (1) a first function of the item at time T1 and an item at time T1−D1, wherein D1 is a pre-determined positive quantity (e.g. a constant time offset), (2) a second function of the item at time T1 and an item at time T1+D1, (3) a third function of the item at time T1 and an item at time T2, wherein T2 is a pre-determined quantity (e.g. a fixed initial reference time; T2 may be changed (e.g. adjusted, varied, modified) over time; T2 may be updated periodically; T2 may be the beginning of a time period and T1 may be a sliding time in the time period), and (4) a fourth function of the item at time T1 and another item.

At least one of: the first function, the second function, the third function, and/or the fourth function may be a function (e.g. $F(X, Y, \ldots)$) with at least two arguments: X and Y. The two arguments may be scalars. The function (e.g. F) may be a function of at least one of: $X$, $Y$, $(X-Y)$, $(Y-X)$, $abs(X-Y)$, $X^a$, $Y^b$, $abs(X^a - Y^b)$, $(X-Y)^a$, $(X/Y)$, $(X+a)/(Y+b)$, $(X^a/Y^b)$, and $((X/Y)^a - b)$, wherein a and b are may be some predetermined quantities. For example, the function may simply be $abs(X-Y)$, or $(X-Y)^2$, $(X-Y)^4$. The function may be a robust function. For example, the function may be $(X-Y)^2$ when $abs(X-Y)$ is less than a threshold T, and $(X-Y)+a$ when $abs(X-Y)$ is larger than T. Alternatively, the function may be a constant when $abs(X-Y)$ is larger than T. The function may also be bounded by a slowly increasing function when $abs(X-y)$ is larger than T, so that outliers cannot severely affect the result. Another example of the function may be $(abs(X/Y)-a)$, where a=1. In this way, if X=Y (i.e. no change or no activity), the function will give a value of 0. If X is larger than Y, (X/Y) will be larger than 1 (assuming X and Y are positive) and the function will be positive. And if X is less than Y, (X/Y) will be smaller than 1 and the function will be negative. In another example, both arguments X and Y may be n-tuples such that $X=(x\_1, x\_2, \ldots, x\_n)$ and $Y=(y\_1, y\_2, \ldots, y\_n)$. The function may be a function of at least one of: $x\_i$, $y\_i$, $(x\_i - y\_i)$, $(y\_j - x\_i)$, $abs(x\_i - y\_i)$, $x\_i^a$, $y\_i^b$, $abs(x\_i^a - y\_i^b)$, $(x\_i - y\_i)^a$, $(x\_i/y\_i)$, $(x\_i + a)/(y\_i + b)$, $(x\_i^a/y\_i^b)$, and $((x\_i/y\_i)^a - b)$, wherein i is a component index of the n-tuple X and Y, and $1 <= i <= n$, e.g. component index of x_1 is i=1, component index of x_2 is i=2. The function may comprise a component-by-component summation of another function of at least one of the following: $x\_i$, $y\_i$, $(x\_i - y\_i)$, $(y\_i - x\_i)$, $abs(x\_i - y\_i)$, $x\_i^a$, $y\_i^b$, $abs(x\_i^a - y\_i^b)$, $(x\_i - y\_i)^a$, $(x\_i/y\_i)$, $(x\_i + a)/(y\_i + b)$, $(x\_i^a/y\_i^b)$, and $((x\_i/y\_i)^a - b)$, wherein i is the component index of the n-tuple X and Y. For example, the function may be in a form of $\operatorname{sum}\_\{i=1\}^n (abs(x\_i/y\_i)-1)/n$, or $\operatorname{sum}\_\{i=1\}^n w\_i * (abs(x\_i/y\_i)-1)$, where w_i is some weight for component i.

The map may be computed using dynamic time warping (DTW). The DTW may comprise a constraint on at least one of: the map, the items of the first TSCI, the items of the second TSCI, the first time duration, the second time duration, the first section, and/or the second section. Suppose in the map, the $i^{\{th\}}$ domain item is mapped to the $j^{\{th\}}$ range item. The constraint may be on admissible combination of i and j (constraint on relationship between i and j). Mismatch cost between a first section of a first time duration of a first TSCI and a second section of a second time duration of a second TSCI may be computed.

The first section and the second section may be aligned such that a map comprising more than one links may be established between first items of the first TSCI and second items of the second TSCI.

With each link, one of the first items with a first timestamp may be associated with one of the second items with a second timestamp. A mismatch cost between the aligned first section and the aligned second section may be computed. The mismatch cost may comprise a function of: an item-wise cost between a first item and a second item associated by a particular link of the map, and a link-wise cost associated with the particular link of the map.

The aligned first section and the aligned second section may be represented respectively as a first vector and a second vector of same vector length. The mismatch cost may comprise at least one of: an inner product, inner-product-like quantity, quantity based on correlation, correlation indicator, quantity based on covariance, discriminating score, distance, Euclidean distance, absolute distance, Lk distance (e.g. L1, L2, . . . ), weighted distance, distance-like quantity and/or another similarity value, between the first vector and the second vector. The mismatch cost may be normalized by the respective vector length.

A parameter derived from the mismatch cost between the first section of the first time duration of the first TSCI and the second section of the second time duration of the second TSCI may be modeled with a statistical distribution. At least one of: a scale parameter, location parameter and/or another parameter, of the statistical distribution may be estimated.

The first section of the first time duration of the first TSCI may be a sliding section of the first TSCI. The second section of the second time duration of the second TSCI may be a sliding section of the second TSCI.

A first sliding window may be applied to the first TSCI and a corresponding second sliding window may be applied to the second TSCI. The first sliding window of the first TSCI and the corresponding second sliding window of the second TSCI may be aligned.

Mismatch cost between the aligned first sliding window of the first TSCI and the corresponding aligned second sliding window of the second TSCI may be computed. The current event may be associated with at least one of: the known event, the unknown event and/or the another event, based on the mismatch cost.

The classifier may be applied to at least one of: each first section of the first time duration of the first TSCI, and/or each second section of the second time duration of the second TSCI, to obtain at least one tentative classification results. Each tentative classification result may be associated with a respective first section and a respective second section.

The current event may be associated with at least one of: the known event, the unknown event, a class/category/group/grouping/list/set of unknown events, and/or the another event, based on the mismatch cost. The current event may be associated with at least one of: the known event, the unknown event and/or the another event, based on a largest number of tentative classification results in more than one sections of the first TSCI and corresponding more than sections of the second TSCI. For example, the current event may be associated with a particular known event if the mismatch cost points to the particular known event for N consecutive times (e.g. N=10). In another example, the current event may be associated with a particular known event if the percentage of mismatch cost within the immediate past N consecutive N pointing to the particular known event exceeds a certain threshold (e.g. >80%).

In another example, the current event may be associated with a known event that achieves smallest mismatch cost for the most times within a time period. The current event may be associated with a known event that achieves smallest overall mismatch cost, which is a weighted average of at least one mismatch cost associated with the at least one first sections. The current event may be associated with a particular known event that achieves smallest of another overall cost. The current event may be associated with the "unknown event" if none of the known events achieve mismatch cost lower than a first threshold T1 in a sufficient percentage of the at least one first section. The current event may also be associated with the "unknown event" if none of the events achieve an overall mismatch cost lower than a second threshold T2. The current event may be associated with at least one of: the known event, the unknown event and/or the another event, based on the mismatch cost and additional mismatch cost associated with at least one additional section of the first TSCI and at least one additional section of the second TSCI. The known events may comprise at least one of: a door closed event, door open event, window closed event, window open event, multi-state event, on-state event, off-state event, intermediate state event, continuous state event, discrete state event, human-present event, human-absent event, sign-of-life-present event, and/or a sign-of-life-absent event.

A projection for each CI may be trained using a dimension reduction method based on the training TSCI. The dimension reduction method may comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and/or another method. The projection may be applied to at least one of: the training TSCI associated with the at least one event, and/or the current TSCI, for the classifier.

The classifier of the at least one event may be trained based on the projection and the training TSCI associated with the at least one event. The at least one current TSCI may be classified/categorized based on the projection and the current TSCI. The projection may be re-trained using at least one of: the dimension reduction method, and another dimension reduction method, based on at least one of: the training TSCI, at least one current TSCI before retraining the projection, and/or additional training TSCI. The another dimension reduction method may comprise at least one of: principal component analysis (PCA), PCA with different kernels, independent component analysis (ICA), Fisher linear discriminant, vector quantization, supervised learning, unsupervised learning, self-organizing maps, auto-encoder, neural network, deep neural network, and/or yet another method. The classifier of the at least one event may be re-trained based on at least one of: the re-trained projection, the training TSCI associated with the at least one events, and/or at least one current TSCI. The at least one current TSCI may be classified based on: the re-trained projection, the re-trained classifier, and/or the current TSCI.

Each CI may comprise a vector of complex values. Each complex value may be preprocessed to give the magnitude of the complex value. Each CI may be preprocessed to give a vector of non-negative real numbers comprising the magnitude of corresponding complex values. Each training TSCI may be weighted in the training of the projection. The projection may comprise more than one projected components. The projection may comprise at least one most significant projected component. The projection may comprise at least one projected component that may be beneficial for the classifier.

Channel/channel information/venue/spatial-temporal info/motion/object

The channel information (CI) may be associated with/may comprise signal strength, signal amplitude, signal phase, spectral power measurement, modem parameters (e.g. used in relation to modulation/demodulation in digital communication systems such as WiFi, 4G/LTE), dynamic beamforming information (including feedback or steering matrices generated by wireless communication devices, according to a standardized process, e.g., IEEE 802.11, or another standard i, transfer function components, radio state (e.g. used in digital communication systems to decode digital data, baseband processing state, RF processing state, etc.), measurable variables, sensed data, coarse-grained/fine-grained information of a layer (e.g. physical layer, data link layer, MAC layer, etc.), digital setting, gain setting, RF filter setting, RF front end switch setting, DC offset setting, DC correction setting, IQ compensation setting, effect(s) on the wireless signal by the environment (e.g. venue) during propagation, transformation of an input signal (the wireless signal transmitted by the Type 1 device) to an output signal (the wireless signal received by the Type 2 device), a stable behavior of the environment, a state profile, wireless channel measurements, received signal strength indicator (RSSI), channel state information (CSI), channel impulse response (CIR), channel frequency response (CFR), characteristics of frequency components (e.g. subcarriers) in a bandwidth, channel characteristics, channel filter response, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another channel information. Each CI may be associated with a time stamp, and/or an arrival time. A CSI can be used to equalize/undo/minimize/reduce the multipath channel effect (of the transmission channel) to demodulate a signal similar to the one transmitted by the transmitter through the multipath channel. The CI may be associated with information associated with a frequency band, frequency signature, frequency phase, frequency amplitude, frequency trend, frequency characteristics, frequency-like characteristics, time domain element, frequency domain element, time-frequency domain element, orthogonal decomposition characteristics, and/or non-orthogonal decomposition characteristics of the signal through the channel. The TSCI may be a stream of wireless signals (e.g. CI).

The CI may be preprocessed, processed, postprocessed, stored (e.g. in local memory, portable/mobile memory, removable memory, storage network, cloud memory, in a volatile manner, in a non-volatile manner), retrieved, transmitted and/or received. One or more modem parameters and/or radio state parameters may be held constant. The modem parameters may be applied to a radio subsystem. The modem parameters may represent a radio state. A motion detection signal (e.g. baseband signal, and/or packet decoded/demodulated from the baseband signal, etc.) may be obtained by processing (e.g. down-converting) the first wireless signal (e.g. RF/WiFi/LTE/5G signal) by the radio subsystem using the radio state represented by the stored modem parameters. The modem parameters/radio state may be updated (e.g. using previous modem parameters or previous radio state). Both the previous and updated modem parameters/radio states may be applied in the radio subsystem in the digital communication system. Both the previous and updated modem parameters/radio states may be compared/analyzed/processed/monitored in the task.

The channel information may also be modem parameters (e.g. stored or freshly computed) used to process the wireless signal. The wireless signal may comprise a plurality of probe signals. The same modem parameters may be used to process more than one probe signals. The same modem parameters may also be used to process more than one wireless signals. The modem parameters may comprise parameters that indicate settings or an overall configuration for the operation of a radio subsystem or a baseband subsystem of a wireless sensor device (or both). The modem parameters may include one or more of: a gain setting, an RF filter setting, an RF front end switch setting, a DC offset setting, or an IQ compensation setting for a radio subsystem, or a digital DC correction setting, a digital gain setting, and/or a digital filtering setting (e.g. for a baseband subsystem). The CI may also be associated with information associated with a time period, time signature, timestamp, time amplitude, time phase, time trend, and/or time characteristics of the signal. The CI may be associated with information associated with a time-frequency partition, signature, amplitude, phase, trend, and/or characteristics of the signal. The CI may be associated with a decomposition of the signal. The CI may be associated with information associated with a direction, angle of arrival (AoA), angle of a directional antenna, and/or a phase of the signal through the channel. The CI may be associated with attenuation patterns of the signal through the channel. Each CI may be associated with a Type 1 device and a Type 2 device. Each CI may be associated with an antenna of the Type 1 device and an antenna of the Type 2 device.

The CI may be obtained from a communication hardware (e.g. of Type 2 device, or Type 1 device) that is capable of providing the CI. The communication hardware may be a WiFi-capable chip/IC (integrated circuit), chip compliant with a 802.11 or 802.16 or another wireless/radio standard, next generation WiFi-capable chip, LTE-capable chip, 5G-capable chip, 6G/7G/8G-capable chip, Bluetooth-enabled chip, NFC (near field communication)-enabled chip, BLE (Bluetooth low power)-enabled chip, UWB chip, another communication chip (e.g. Zigbee, WiMax, mesh network), etc. The communication hardware computes the CI and stores the CI in a buffer memory and make the CI available for extraction. The CI may comprise data and/or at least one matrices related to channel state information (CSI). The at least one matrices may be used for channel equalization, and/or beam forming, etc. The channel may be associated with a venue. The attenuation may be due to signal propagation in the venue, signal propagating/reflection/refraction/diffraction through/at/around air (e.g. air of venue), refraction medium/reflection surface such as wall, doors, furniture, obstacles and/or barriers, etc. The attenuation may be due to reflection at surfaces and obstacles (e.g. reflection surface, obstacle) such as floor, ceiling, furniture, fixtures, objects, people, pets, etc. Each CI may be associated with a timestamp. Each CI may comprise N1 components (e.g. N1 frequency domain components in CFR, N1 time domain components in CIR, or N1 decomposition components). Each component may be associated with a component index. Each component may be a real, imaginary, or complex quantity, magnitude, phase, flag, and/or set. Each CI may comprise a vector or matrix of complex numbers, a set of mixed quantities, and/or a multi-dimensional collection of at least one complex numbers.

Components of a TSCI associated with a particular component index may form a respective component time series associated with the respective index. A TSCI may be divided into N1 component time series. Each respective component time series is associated with a respective component index. The characteristics/STI of the motion of the object may be monitored based on the component time series. In one example, one or more ranges of CI components (e.g. one range being from component 11 to component 23, a second range being from component 44 to component 50, and a third range having only one component) may be selected based on some criteria/cost function/signal quality metric (e.g. based on signal-to-noise ratio, and/or interference level) for further processing.

A component-wise characteristic of a component-feature time series of a TSCI may be computed. The component-wise characteristics may be a scalar (e.g. energy) or a function with a domain and a range (e.g. an autocorrelation function, transform, inverse transform). The characteristics/STI of the motion of the object may be monitored based on the component-wise characteristics. A total characteristics (e.g. aggregate characteristics) of the TSCI may be computed based on the component-wise characteristics of each component time series of the TSCI. The total characteristics may be a weighted average of the component-wise characteristics. The characteristics/STI of the motion of the object may be monitored based on the total characteristics. An aggregate quantity may be a weighted average of individual quantities.

The Type 1 device and Type 2 device may support WiFi, WiMax, 3G/beyond 3G, 4G/beyond 4G, LTE, LTE-A, 5G, 6G, 7G, Bluetooth, NFC, BLE, Zigbee, UWB, UMTS, 3GPP, GSM, EDGE, TDMA, FDMA, CDMA, WCDMA, TD-SCDMA, mesh network, proprietary wireless system, IEEE 802.11 standard, 802.15 standard, 802.16 standard, 3GPP standard, and/or another wireless system.

A common wireless system and/or a common wireless channel may be shared by the Type 1 transceiver and/or the at least one Type 2 transceiver. The at least one Type 2 transceiver may transmit respective signal contemporaneously (or: asynchronously, synchronously, sporadically, continuously, repeatedly, concurrently, simultaneously and/or temporarily) using the common wireless system and/or the common wireless channel. The Type 1 transceiver may transmit a signal to the at least one Type 2 transceiver using the common wireless system and/or the common wireless channel.

Each Type 1 device and Type 2 device may have at least one transmitting/receiving antenna. Each CI may be associated with one of the transmitting antenna of the Type 1 device and one of the receiving antenna of the Type 2 device. Each pair of a transmitting antenna and a receiving antenna may be associated with a link, a path, a communication path, signal hardware path, etc. For example, if the Type 1 device has M (e.g. 3) transmitting antennas, and the Type 2 device has N (e.g. 2) receiving antennas, there may be M×N (e.g. 3×2=6) links or paths. Each link or path may be associated with a TSCI.

The at least one TSCI may correspond to various antenna pairs between the Type 1 device and the Type 2 device. The Type 1 device may have at least one antenna. The Type 2 device may also have at least one antenna. Each TSCI may be associated with an antenna of the Type 1 device and an antenna of the Type 2 device. Averaging or weighted averaging over antenna links may be performed. The averaging or weighted averaging may be over the at least one TSCI. The averaging may optionally be performed on a subset of the at least one TSCI corresponding to a subset of the antenna pairs.

Timestamps of CI of a portion of a TSCI may be irregular and may be corrected so that corrected timestamps of time-corrected CI may be uniformly spaced in time. In the case of multiple Type 1 devices and/or multiple Type 2 devices, the corrected timestamp may be with respect to the same or different clock. An original timestamp associated with each of the CI may be determined. The original timestamp may not be uniformly spaced in time. Original timestamps of all CI of the particular portion of the particular TSCI in the current sliding time window may be corrected so that corrected timestamps of time-corrected CI may be uniformly spaced in time.

The characteristics and/or STI (e.g. motion information) may comprise: location, location coordinate, change in location, position (e.g. initial position, new position), position on map, height, horizontal location, vertical location, distance, displacement, speed, acceleration, rotational speed, rotational acceleration, direction, angle of motion, azimuth, direction of motion, rotation, path, deformation, transformation, shrinking, expanding, gait, gait cycle, head motion, repeated motion, periodic motion, pseudo-periodic motion, impulsive motion, sudden motion, fall-down motion, transient motion, behavior, transient behavior, period of motion, frequency of motion, time trend, temporal profile, temporal characteristics, occurrence, change, temporal change, change of CI, change in frequency, change in timing, change of gait cycle, timing, starting time, initiating time, ending time, duration, history of motion, motion type, motion classification, frequency, frequency spectrum, frequency characteristics, presence, absence, proximity, approaching, receding, identity/identifier of the object, composition of the object, head motion rate, head motion direction, mouth-related rate, eye-related rate, breathing rate, heart rate, tidal volume, depth of breath, inhale time, exhale time, inhale time to exhale time ratio, airflow rate, heart heat-to-beat interval, heart rate variability, hand motion rate, hand motion direction, leg motion, body motion, walking rate, hand motion rate, positional characteristics, characteristics associated with movement (e.g. change in position/location) of the object, tool motion, machine motion, complex motion, and/or combination of multiple motions, event, signal statistics, signal dynamics, anomaly, motion statistics, motion parameter, indication of motion detection, motion magnitude, motion phase, similarity score, distance score, Euclidean distance, weighted distance, L_1 norm, L_2 norm, L_k norm for k>2, statistical distance, correlation, correlation indicator, auto-correlation, covariance, auto-covariance, cross-covariance, inner product, outer product, motion signal transformation, motion feature, presence of motion, absence of motion, motion localization, motion identification, motion recognition, presence of object, absence of object, entrance of object, exit of object, a change of object, motion cycle, motion count, gait cycle, motion rhythm, deformation motion, gesture, handwriting, head motion, mouth motion, heart motion, internal organ motion, motion trend, size, length, area, volume, capacity, shape, form, tag, starting/initiating location, ending location, starting/initiating quantity, ending quantity, event, fall-down event, security event, accident event, home event, office event, factory event, warehouse event, manufacturing event, assembly line event, maintenance event, car-related event, navigation event, tracking event, door event, door-open event, door-close event, window event, window-open event, window-close event, repeatable event, one-time event, consumed quantity, unconsumed quantity, state, physical state, health state, well-being state, emotional state, mental state, another event, analytics, output responses, and/or another information. The characteristics and/or STI may be computed/monitored based on a feature computed from a CI or a TSCI (e.g. feature computation/extraction). A static segment or profile (and/or a dynamic segment/profile) may be identified/computed/analyzed/monitored/extracted/obtained/marked/presented/indicated/highlighted/stored/communicated based on an analysis of the feature. The analysis may comprise a motion detection/movement assessment/presence detection. Computational workload may be shared among the Type 1 device, the Type 2 device and another processor.

The Type 1 device and/or Type 2 device may be a local device. The local device may be: a smart phone, smart device, TV, sound bar, set-top box, access point, router, repeater, wireless signal repeater/extender, remote control, speaker, fan, refrigerator, microwave, oven, coffee machine, hot water pot, utensil, table, chair, light, lamp, door lock, camera, microphone, motion sensor, security device, fire hydrant, garage door, switch, power adapter, computer, dongle, computer peripheral, electronic pad, sofa, tile, accessory, home device, vehicle device, office device, building device, manufacturing device, watch, glasses, clock, television, oven, air-conditioner, accessory, utility, appliance, smart machine, smart vehicle, internet-of-thing (IoT) device, internet-enabled device, computer, portable computer, tablet, smart house, smart office, smart building, smart parking lot, smart system, and/or another device.

Each Type 1 device may be associated with a respective identifier (e.g. ID). Each Type 2 device may also be associated with a respective identify (ID). The ID may comprise: numeral, combination of text and numbers, name, password, account, account ID, web link, web address, index to some information, and/or another ID. The ID may be assigned. The ID may be assigned by hardware (e.g. hardwired, via dongle and/or other hardware), software and/or firmware. The ID may be stored (e.g. in database, in memory, in server (e.g. hub device), in the cloud, stored locally, stored remotely, stored permanently, stored temporarily) and may be retrieved. The ID may be associated with at least one record, account, user, household, address, phone number, social security number, customer number, another ID, another identifier, timestamp, and/or collection of data. The ID and/or part of the ID of a Type 1 device may be made available to a Type 2 device. The ID may be used for registration, initialization, communication, identification, verification, detection, recognition, authentication, access control, cloud access, networking, social networking, logging, recording, cataloging, classification, tagging, association, pairing, transaction, electronic transaction, and/or intellectual property control, by the Type 1 device and/or the Type 2 device.

The object may be person, user, subject, passenger, child, older person, baby, sleeping baby, baby in vehicle, patient, worker, high-value worker, expert, specialist, waiter, customer in mall, traveler in airport/train station/bus terminal/ shipping terminals, staff/worker/customer service personnel in factory/mall/supermarket/office/workplace, serviceman in sewage/air ventilation system/lift well, lifts in lift wells, elevator, inmate, people to be tracked/monitored, animal, plant, living object, pet, dog, cat, smart phone, phone accessory, computer, tablet, portable computer, dongle, computing accessory, networked devices, WiFi devices, IoT devices, smart watch, smart glasses, smart devices, speaker, keys, smart key, wallet, purse, handbag, backpack, goods, cargo, luggage, equipment, motor, machine, air conditioner, fan, air conditioning equipment, light fixture, moveable light, television, camera, audio and/or video equipment, stationary, surveillance equipment, parts, signage, tool, cart, ticket, parking ticket, toil ticket, airplane ticket, credit card, plastic card, access card, food packaging, utensil, table, chair, cleaning equipment/tool, vehicle, car, cars in parking facilities, merchandise in warehouse/store/supermarket/distribution center, boat, bicycle, airplane, drone, remote control car/plane/boat, robot, manufacturing device, assembly line, material/unfinished part/robot/wagon/transports on factory floor, object to be tracked in airport/shopping mart/ supermarket, non-object, absence of an object, presence of an object, object with form, object with changing form, object with no form, mass of fluid, mass of liquid, mass of gas/smoke, fire, flame, electromagnetic (EM) source, EM medium, and/or another object.

The object itself may be communicatively coupled with some network, such as WiFi, MiFi, 3G/4G/LTE/5G/6G/7G, Bluetooth, NFC, BLE, WiMax, Zigbee, UMTS, 3GPP, GSM, EDGE, TDMA, FDMA, CDMA, WCDMA, TD-SCDMA, mesh network, adhoc network, and/or other network. The object itself may be bulky with AC power supply, but is moved during installation, cleaning, maintenance, renovation, etc. It may also be installed in moveable platform such as lift, pad, movable, platform, elevator, conveyor belt, robot, drone, forklift, car, boat, vehicle, etc. The object may have multiple parts, each part with different movement (e.g. change in position/location). For example, the object may be a person walking forward. While walking, his left hand and right hand may move in different direction, with different instantaneous speed, acceleration, motion, etc.

The wireless transmitter (e.g. Type 1 device), the wireless receiver (e.g. Type 2 device), another wireless transmitter and/or another wireless receiver may move with the object and/or another object (e.g. in prior movement, current movement and/or future movement. They may be communicatively coupled to one or more nearby device. They may transmit TSCI and/or information associated with the TSCI to the nearby device, and/or each other. They may be with the nearby device. The wireless transmitter and/or the wireless receiver may be part of a small (e.g. coin-size, cigarette box size, or even smaller), light-weight portable device. The portable device may be wirelessly coupled with a nearby device.

The nearby device may be smart phone, iPhone, Android phone, smart device, smart appliance, smart vehicle, smart gadget, smart TV, smart refrigerator, smart speaker, smart watch, smart glasses, smart pad, iPad, computer, wearable computer, notebook computer, gateway. The nearby device may be connected to a cloud server, local server (e.g. hub device) and/or other server via internet, wired internet connection and/or wireless internet connection. The nearby device may be portable. The portable device, the nearby device, a local server (e.g. hub device) and/or a cloud server may share the computation and/or storage for a task (e.g. obtain TSCI, determine characteristics/STI of the object associated with the movement (e.g. change in position/ location) of the object, computation of time series of power (e.g. signal strength) information, determining/computing the particular function, searching for local extremum, classification, identifying particular value of time offset, denoising, processing, simplification, cleaning, wireless smart sensing task, extract CI from signal, switching, segmentation, estimate trajectory/path/track, process the map, processing trajectory/path/track based on environment models/ constraints/limitations, correction, corrective adjustment, adjustment, map-based (or model-based) correction, detecting error, checking for boundary hitting, thresholding) and information (e.g. TSCI). The nearby device may/may not move with the object. The nearby device may be portable/ not portable/moveable/non-moveable. The nearby device may use battery power, solar power, AC power and/or other power source. The nearby device may have replaceable/non-replaceable battery, and/or rechargeable/non-rechargeable battery. The nearby device may be similar to the object. The nearby device may have identical (and/or similar) hardware and/or software to the object. The nearby device may be a smart device, network enabled device, device with connection to WiFi/3G/4G/5G/6G/Zigbee/Bluetooth/NFC/UMTS/ 3GPP/GSM/EDGE/TDMA/FDMA/CDMA/WCDMA/TD-SCDMA/adhoc network/other network, smart speaker, smart watch, smart clock, smart appliance, smart machine, smart equipment, smart tool, smart vehicle, internet-of-thing (IoT) device, internet-enabled device, computer, portable computer, tablet, and another device. The nearby device and/or at least one processor associated with the wireless receiver, the wireless transmitter, the another wireless receiver, the another wireless transmitter and/or a cloud server (in the cloud) may determine the initial STI of the object. Two or more of them may determine the initial spatial-temporal info jointly. Two or more of them may share intermediate information in the determination of the initial STI (e.g. initial position).

In one example, the wireless transmitter (e.g. Type 1 device, or Tracker Bot) may move with the object. The wireless transmitter may send the signal to the wireless receiver (e.g. Type 2 device, or Origin Register) or determining the initial STI (e.g. initial position) of the object. The wireless transmitter may also send the signal and/or another signal to another wireless receiver (e.g. another Type 2 device, or another Origin Register) for the monitoring of the motion (spatial-temporal info) of the object. The wireless receiver may also receive the signal and/or another signal from the wireless transmitter and/or the another wireless transmitter for monitoring the motion of the object. The location of the wireless receiver and/or the another wireless receiver may be known. In another example, the wireless receiver (e.g. Type 2 device, or Tracker Bot) may move with the object. The wireless receiver may receive the signal transmitted from the wireless transmitter (e.g. Type 1 device, or Origin Register) for determining the initial spatial-temporal info (e.g. initial position) of the object. The wireless receiver may also receive the signal and/or another signal from another wireless transmitter (e.g. another Type 1 device, or another Origin Register) for the monitoring of the current motion (e.g. spatial-temporal info) of the object. The wireless transmitter may also transmit the signal and/or another signal to the wireless receiver and/or the another wireless receiver (e.g. another Type 2 device, or another Tracker Bot) for monitoring the motion of the object. The location of the wireless transmitter and/or the another wireless transmitter may be known.

The venue may be a space such as a sensing area, room, house, office, property, workplace, hallway, walkway, lift, lift well, escalator, elevator, sewage system, air ventilations system, staircase, gathering area, duct, air duct, pipe, tube, enclosed space, enclosed structure, semi-enclosed structure, enclosed area, area with at least one wall, plant, machine, engine, structure with wood, structure with glass, structure with metal, structure with walls, structure with doors, structure with gaps, structure with reflection surface, structure with fluid, building, roof top, store, factory, assembly line, hotel room, museum, classroom, school, university, government building, warehouse, garage, mall, airport, train station, bus terminal, hub, transportation hub, shipping terminal, government facility, public facility, school, university, entertainment facility, recreational facility, hospital, pediatric/neonatal wards, seniors home, elderly care facility, geriatric facility, community center, stadium, playground, park, field, sports facility, swimming facility, track and/or field, basketball court, tennis court, soccer stadium, baseball stadium, gymnasium, hall, garage, shopping mart, mall, supermarket, manufacturing facility, parking facility, construction site, mining facility, transportation facility, highway, road, valley, forest, wood, terrain, landscape, den, patio, land, path, amusement park, urban area, rural area, suburban area, metropolitan area, garden, square, plaza, music hall, downtown facility, over-air facility, semi-open facility, closed area, train platform, train station, distribution center, warehouse, store, distribution center, storage facility, underground facility, space (e.g. above ground, outer-space) facility, floating facility, cavern, tunnel facility, indoor facility, open-air facility, outdoor facility with some walls/doors/reflective barriers, open facility, semi-open facility, car, truck, bus, van, container, ship/boat, submersible, train, tram, airplane, vehicle, mobile home, cave, tunnel, pipe, channel, metropolitan area, downtown area with relatively tall buildings, valley, well, duct, pathway, gas line, oil line, water pipe, network of interconnecting pathways/alleys/roads/tubes/cavities/caves/pipe-like structure/air space/fluid space, human body, animal body, body cavity, organ, bone, teeth, soft tissue, hard tissue, rigid tissue, non-rigid tissue, blood/body fluid vessel, windpipe, air duct, den, etc. The venue may be indoor space, outdoor space, The venue may include both the inside and outside of the space. For example, the venue may include both the inside of a building and the outside of the building. For example, the venue can be a building that has one floor or multiple floors, and a portion of the building can be underground. The shape of the building can be, e.g., round, square, rectangular, triangle, or irregular-shaped. These are merely examples. The disclosure can be used to detect events in other types of venue or spaces.

The wireless transmitter (e.g. Type 1 device) and/or the wireless receiver (e.g. Type 2 device) may be embedded in a portable device (e.g. a module, or a device with the module) that may move with the object (e.g. in prior movement and/or current movement). The portable device may be communicatively coupled with the object using a wired connection (e.g. through USB, microUSB, Firewire, HDMI, serial port, parallel port, and other connectors) and/or a connection (e.g. Bluetooth, Bluetooth Low Energy (BLE), WiFi, LTE, NFC, ZigBee). The portable device may be a lightweight device. The portable may be powered by battery, rechargeable battery and/or AC power. The portable device may be very small (e.g. at sub-millimeter scale and/or sub-centimeter scale), and/or small (e.g. coin-size, card-size, pocket-size, or larger). The portable device may be large, sizable, and/or bulky (e.g. heavy machinery to be installed). The portable device may be a WiFi hotspot, access point, mobile WiFi (MiFi), dongle with USB/micro USB/Firewire/other connector, smartphone, portable computer, computer, tablet, smart device, internet-of-thing (IoT) device, WiFi-enabled device, LTE-enabled device, a smart watch, smart glass, smart mirror, smart antenna, smart battery, smart light, smart pen, smart ring, smart door, smart window, smart clock, small battery, smart wallet, smart belt, smart handbag, smart clothing/garment, smart ornament, smart packaging, smart paper/book/magazine/poster/printed matter/signage/display/lighted system/lighting system, smart key/tool, smart bracelet/chain/necklace/wearable/accessory, smart pad/cushion, smart tile/block/brick/building material/other material, smart garbage can/waste container, smart food carriage/storage, smart ball/racket, smart chair/sofa/bed, smart shoe/footwear/carpet/mat/shoe rack, smart glove/hand wear/ring/hand ware, smart hat/headwear/makeup/sticker/tattoo, smart mirror, smart toy, smart pill, smart utensil, smart bottle/food container, smart tool, smart device, IoT device, WiFi enabled device, network enabled device, 3G/4G/5G/6G enabled device, UMTS devices, 3GPP devices, GSM devices, EDGE devices, TDMA devices, FDMA devices, CDMA devices, WCDMA devices, TD-SCDMA devices, embeddable device, implantable device, air conditioner, refrigerator, heater, furnace, furniture, oven, cooking device, television/set-top box (STB)/DVD player/audio player/video player/remote control, hi-fi, audio device, speaker, lamp/light, wall, door, window, roof, roof tile/shingle/structure/attic structure/device/feature/installation/fixtures, lawn mower/garden tools/yard tools/mechanics tools/garage tools/, garbage can/container, 20-ft/40-ft container, storage container, factory/manufacturing/production device, repair tools, fluid container, machine, machinery to be installed, vehicle, cart, wagon, warehouse vehicle, car, bicycle, motorcycle, boat, vessel, airplane, basket/box/bag/bucket/container, smart plate/cup/bowl/pot/mat/utensils/kitchen tools/kitchen devices/kitchen accessories/cabinets/tables/chairs/tiles/lights/water pipes/taps/gas range/oven/dishwashing machine/etc. The portable device may have a battery that may be replaceable, irreplaceable, rechargeable, and/or non-rechargeable. The portable device may be wirelessly charged. The portable device may be a smart payment card. The portable device may be a payment card used in parking lots, highways, entertainment parks, or other venues/facilities that need payment. The portable device may have an identity (ID)/identifier as described above.

An event may be monitored based on the TSCI. The event may be an object related event, such as fall-down of the object (e.g. an person and/or a sick person), rotation, hesitation, pause, impact (e.g. a person hitting a sandbag, door, window, bed, chair, table, desk, cabinet, box, another person, animal, bird, fly, table, chair, ball, bowling ball, tennis ball, football, soccer ball, baseball, basketball, volley ball), two-body action (e.g. a person letting go a balloon, catching a fish, molding a clay, writing a paper, person typing on a computer), car moving in a garage, person carrying a smart phone and walking around an airport/mall/government building/office/etc., autonomous moveable object/machine moving around (e.g. vacuum cleaner, utility vehicle, car, drone, self-driving car).

The task or the wireless smart sensing task may comprise: object detection, presence detection, proximity detection, object recognition, activity recognition, object verification, object counting, daily activity monitoring, well-being monitoring, vital sign monitoring, health condition monitoring, baby monitoring, elderly monitoring, sleep monitoring, sleep stage monitoring, walking monitoring, exercise monitoring, tool detection, tool recognition, tool verification, patient detection, patient monitoring, patient verification, machine detection, machine recognition, machine verification, human detection, human recognition, human verification, baby detection, baby recognition, baby verification, human breathing detection, human breathing recognition, human breathing estimation, human breathing verification, human heart beat detection, human heart beat recognition, human heart beat estimation, human heart beat verification, fall-down detection, fall-down recognition, fall-down estimation, fall-down verification, emotion detection, emotion recognition, emotion estimation, emotion verification, motion detection, motion degree estimation, motion recognition, motion estimation, motion verification, periodic motion detection, periodic motion recognition, periodic motion estimation, periodic motion verification, repeated motion detection, repeated motion recognition, repeated motion estimation, repeated motion verification, stationary motion detection, stationary motion recognition, stationary motion estimation, stationary motion verification, cyclo-stationary motion detection, cyclo-stationary motion recognition, cyclo-stationary motion estimation, cyclo-stationary motion verification, transient motion detection, transient motion recognition, transient motion estimation, transient motion verification, trend detection, trend recognition, trend estimation, trend verification, breathing detection, breathing recognition, breathing estimation, breathing estimation, human biometrics detection, human biometric recognition, human biometrics estimation, human biometrics verification, environment informatics detection, environment informatics recognition, environment informatics estimation, environment informatics verification, gait detection, gait recognition, gait estimation, gait verification, gesture detection, gesture recognition, gesture estimation, gesture verification, machine learning, supervised learning, unsupervised learning, semi-supervised learning, clustering, feature extraction, featuring training, principal component analysis, eigen-decomposition, frequency decomposition, time decomposition, time-frequency decomposition, functional decomposition, other decomposition, training, discriminative training, supervised training, unsupervised training, semi-supervised training, neural network, sudden motion detection, fall-down detection, danger detection, life-threat detection, regular motion detection, stationary motion detection, cyclo-stationary motion detection, intrusion detection, suspicious motion detection, security, safety monitoring, navigation, guidance, map-based processing, map-based correction, model-based processing/correction, irregularity detection, locationing, room sensing, tracking, multiple object tracking, indoor tracking, indoor position, indoor navigation, energy management, power transfer, wireless power transfer, object counting, car tracking in parking garage, activating a device/system (e.g. security system, access system, alarm, siren, speaker, television, entertaining system, camera, heater/air-conditioning (HVAC) system, ventilation system, lighting system, gaming system, coffee machine, cooking device, cleaning device, housekeeping device), geometry estimation, augmented reality, wireless communication, data communication, signal broadcasting, networking, coordination, administration, encryption, protection, cloud computing, other processing and/or other task. The task may be performed by the Type 1 device, the Type 2 device, another Type 1 device, another Type 2 device, a nearby device, a local server (e.g. hub device), edge server, a cloud server, and/or another device. The task may be based on TSCI between any pair of Type 1 device and Type 2 device. A Type 2 device may be a Type 1 device, and vice versa. A Type 2 device may play/perform the role (e.g. functionality) of Type 1 device temporarily, continuously, sporadically, simultaneously, and/or contemporaneously, and vice versa. A first part of the task may comprise at least one of: preprocessing, processing, signal conditioning, signal processing, post-processing, processing sporadically/continuously/simultaneously/contemporaneously/dynamically/adaptive/on-demand/as-needed, calibrating, denoising, feature extraction, coding, encryption, transformation, mapping, motion detection, motion estimation, motion change detection, motion pattern detection, motion pattern estimation, motion pattern recognition, vital sign detection, vital sign estimation, vital sign recognition, periodic motion detection, periodic motion estimation, repeated motion detection/estimation, breathing rate detection, breathing rate estimation, breathing pattern detection, breathing pattern estimation, breathing pattern recognition, heart beat detection, heart beat estimation, heart pattern detection, heart pattern estimation, heart pattern recognition, gesture detection, gesture estimation, gesture recognition, speed detection, speed estimation, object locationing, object tracking, navigation, acceleration estimation, acceleration detection, fall-down detection, change detection, intruder (and/or illegal action) detection, baby detection, baby monitoring, patient monitoring, object recognition, wireless power transfer, and/or wireless charging.

A second part of the task may comprise at least one of: a smart home task, smart office task, smart building task, smart factory task (e.g. manufacturing using a machine or an assembly line), smart internet-of-thing (IoT) task, smart system task, smart home operation, smart office operation, smart building operation, smart manufacturing operation (e.g. moving supplies/parts/raw material to a machine/an assembly line), IoT operation, smart system operation, turning on a light, turning off the light, controlling the light in at least one of: a room, region, and/or the venue, playing a sound clip, playing the sound clip in at least one of: the room, the region, and/or the venue, playing the sound clip of at least one of: a welcome, greeting, farewell, first message, and/or a second message associated with the first part of the task, turning on an appliance, turning off the appliance, controlling the appliance in at least one of: the room, the region, and/or the venue, turning on an electrical system, turning off the electrical system, controlling the electrical system in at least one of: the room, the region, and/or the venue, turning on a security system, turning off the security system, controlling the security system in at least one of: the room, the region, and/or the venue, turning on a mechanical system, turning off a mechanical system, controlling the mechanical system in at least one of: the room, the region, and/or the venue, and/or controlling at least one of: an air conditioning system, heating system, ventilation system, lighting system, heating device, stove, entertainment system, door, fence, window, garage, computer system, networked device, networked system, home appliance, office equipment, lighting device, robot (e.g. robotic arm), smart vehicle, smart machine, assembly line, smart device, internet-of-thing (IoT) device, smart home device, and/or a smart office device.

The task may include: detect a user returning home, detect a user leaving home, detect a user moving from one room to another, detect/control/lock/unlock/open/close/partially open a window/door/garage door/blind/curtain/panel/solar panel/sun shade, detect a pet, detect/monitor a user doing something (e.g. sleeping on sofa, sleeping in bedroom, running on treadmill, cooking, sitting on sofa, watching TV, eating in kitchen, eating in dining room, going upstairs/downstairs, going outside/coming back, in the rest room), monitor/detect location of a user/pet, do something (e.g. send a message, notify/report to someone) automatically upon detection, do something for the user automatically upon detecting the user, turn on/off/dim a light, turn on/off music/radio/home entertainment system, turn on/off/adjust/control TV/HiFi/set-top-box (STB)/home entertainment system/smart speaker/smart device, turn on/off/adjust air conditioning system, turn on/off/adjust ventilation system, turn on/off/adjust heating system, adjust/control curtains/light shades, turn on/off/wake a computer, turn on/off/pre-heat/control coffee machine/hot water pot, turn on/off/control/preheat cooker/oven/microwave oven/another cooking device, check/adjust temperature, check weather forecast, check telephone message box, check mail, do a system check, control/adjust a system, check/control/arm/disarm security system/baby monitor, check/control refrigerator, give a report (e.g. through a speaker such as Google home, Amazon Echo, on a display/screen, via a webpage/email/messaging system/notification system).

For example, when a user arrives home in his car, the task may be to, automatically, detect the user or his car approaching, open the garage door upon detection, turn on the driveway/garage light as the user approaches the garage, turn on air conditioner/heater/fan, etc. As the user enters the house, the task may be to, automatically, turn on the entrance light, turn off driveway/garage light, play a greeting message to welcome the user, turn on the music, turn on the radio and tuning to the user's favorite radio news channel, open the curtain/blind, monitor the user's mood, adjust the lighting and sound environment according to the user's mood or the current/imminent event (e.g. do romantic lighting and music because the user is scheduled to eat dinner with girlfriend in 1 hour) on the user's daily calendar, warm the food in microwave that the user prepared in the morning, do a diagnostic check of all systems in the house, check weather forecast for tomorrow's work, check news of interest to the user, check user's calendar and to-do list and play reminder, check telephone answer system/messaging system/email and give a verbal report using dialog system/speech synthesis, remind (e.g. using audible tool such as speakers/HiFi/speech synthesis/sound/voice/music/song/sound field/background sound field/dialog system, using visual tool such as TV/entertainment system/computer/notebook/smart pad/display/light/color/brightness/patterns/symbols, using haptic tool/virtual reality tool/gesture/tool, using a smart device/appliance/material/furniture/fixture, using web tool/server/hub device/cloud server/fog server/edge server/home network/mesh network, using messaging tool/notification tool/communication tool/scheduling tool/email, using user interface/GUI, using scent/smell/fragrance/taste, using neural tool/nervous system tool, using a combination) the user of his mother's birthday and to call her, prepare a report, and give the report (e.g. using a tool for reminding as discussed above). The task may turn on the air conditioner/heater/ventilation system in advance, or adjust temperature setting of smart thermostat in advance, etc. As the user moves from the entrance to the living room, the task may be to turn on the living room light, open the living room curtain, open the window, turn off the entrance light behind the user, turn on the TV and set-top box, set TV to the user's favorite channel, adjust an appliance according to the user's preference and conditions/states (e.g. adjust lighting and choose/play music to build a romantic atmosphere), etc.

Another example may be: When the user wakes up in the morning, the task may be to detect the user moving around in the bedroom, open the blind/curtain, open the window, turn off the alarm clock, adjust indoor temperature from night-time temperature profile to day-time temperature profile, turn on the bedroom light, turn on the restroom light as the user approaches the restroom, check radio or streaming channel and play morning news, turn on the coffee machine and preheat the water, turn off security system, etc. When the user walks from bedroom to kitchen, the task may be to turn on the kitchen and hallway lights, turn off the bedroom and restroom lights, move the music/message/reminder from the bedroom to the kitchen, turn on the kitchen TV, change TV to morning news channel, lower the kitchen blind and open the kitchen window to bring in fresh air, unlock backdoor for the user to check the backyard, adjust temperature setting for the kitchen, etc. Another example may be: When the user leaves home for work, the task may be to detect the user leaving, play a farewell and/or have-a-good-day message, open/close garage door, turn on/off garage light and driveway light, turn off/dim lights to save energy (just in case the user forgets), close/lock all windows/doors (just in case the user forgets), turn off appliance (especially stove, oven, microwave oven), turn on/arm the home security system to guard the home against any intruder, adjust air conditioning/heating/ventilation systems to "away-from-home" profile to save energy, send alerts/reports/updates to the user's smart phone, etc.

A motion may comprise at least one of: a no-motion, resting motion, non-moving motion, movement, change in position/location, deterministic motion, transient motion, fall-down motion, repeating motion, periodic motion, pseudo-periodic motion, periodic/repeated motion associated with breathing, periodic/repeated motion associated with heartbeat, periodic/repeated motion associated with living object, periodic/repeated motion associated with machine, periodic/repeated motion associated with man-made object, periodic/repeated motion associated with nature, complex motion with transient element and periodic element, repetitive motion, non-deterministic motion, probabilistic motion, chaotic motion, random motion, complex motion with non-deterministic element and deterministic element, stationary random motion, pseudo-stationary random motion, cyclo-stationary random motion, non-stationary random motion, stationary random motion with periodic autocorrelation function (ACF), random motion with periodic ACF for period of time, random motion that is pseudo-stationary for a period of time, random motion of which an instantaneous ACF has a pseudo-periodic/repeating element for a period of time, machine motion, mechanical motion, vehicle motion, drone motion, air-related motion, wind-related motion, weather-related motion, water-related motion, fluid-related motion, ground-related motion, change in electro-magnetic characteristics, subsurface motion, seismic motion, plant motion, animal motion, human motion, normal motion, abnormal motion, dangerous motion, warning motion, suspicious motion, rain, fire, flood, tsunami, explosion, collision, imminent collision, human body motion, head motion, facial motion, eye motion, mouth motion, tongue motion, neck motion, finger motion, hand motion, arm motion, shoulder motion, body motion, chest motion, abdominal motion, hip motion, leg motion, foot motion, body joint motion, knee motion, elbow motion, upper body motion, lower body motion, skin motion, below-skin motion, subcutaneous tissue motion, blood vessel motion, intravenous motion, organ motion, heart motion, lung motion, stomach motion, intestine motion, bowel motion, eating motion, breathing motion, facial expression, eye expression, mouth expression, talking motion, singing motion, eating motion, gesture, hand gesture, arm gesture, keystroke, typing stroke, user-interface gesture, man-machine interaction, gait, dancing movement, coordinated movement, and/or coordinated body movement.

The heterogeneous IC of the Type 1 device and/or Type 2 receiver may comprise low-noise amplifier (LNA), power amplifier, transmit-receive switch, media access controller, baseband radio, 2.4 GHz radio, 3.65 GHz radio, 4.9 GHz radio, 5 GHz radio, 5.9 GHz radio, below 6 GHz radio, below 60 GHz radio and/or another radio. The heterogeneous IC may comprise a processor, a memory communicatively coupled with the processor, and a set of instructions stored in the memory to be executed by the processor. The IC and/or any processor may comprise at least one of: general purpose processor, special purpose processor, microprocessor, multi-processor, multi-core processor, parallel processor, CISC processor, RISC processor, microcontroller, central processing unit (CPU), graphical processor unit (GPU), digital signal processor (DSP), application specific integrated circuit (ASIC), field programmable gate array (FPGA), embedded processor (e.g. ARM), logic circuit, other programmable logic device, discrete logic, and/or a combination. The heterogeneous IC may support broadband network, wireless network, mobile network, mesh network, cellular network, wireless local area network (WLAN), wide area network (WAN), and metropolitan area network (MAN), WLAN standard, WiFi, LTE, LTE-A, LTE-U, 802.11 standard, 802.11a, 802.11b, 802.11g, 802.11n, 802.11ac, 802.11ad, 802.11af, 802.11ah, 802.11ax, 802.11ay, mesh network standard, 802.15 standard, 802.16 standard, cellular network standard, 3G, 3.5G, 4G, beyond 4G, 4.5G, 5G, 6G, 7G, 8G, 9G, UMTS, 3GPP, GSM, EDGE, TDMA, FDMA, CDMA, WCDMA, TD-SCDMA, Bluetooth, Bluetooth Low-Energy (BLE), NFC, Zigbee, WiMax, and/or another wireless network protocol.

The processor may comprise general purpose processor, special purpose processor, microprocessor, microcontroller, embedded processor, digital signal processor, central processing unit (CPU), graphical processing unit (GPU), multi-processor, multi-core processor, and/or processor with graphics capability, and/or a combination. The memory may be volatile, non-volatile, random access memory (RAM), Read Only Memory (ROM), Electrically Programmable ROM (EPROM), Electrically Erasable Programmable ROM (EEPROM), hard disk, flash memory, CD-ROM, DVD-ROM, magnetic storage, optical storage, organic storage, storage system, storage network, network storage, cloud storage, edge storage, local storage, external storage, internal storage, or other form of non-transitory storage medium known in the art. The set of instructions (machine executable code) corresponding to the method steps may be embodied directly in hardware, in software, in firmware, or in combinations thereof. The set of instructions may be embedded, pre-loaded, loaded upon boot up, loaded on the fly, loaded on demand, pre-installed, installed, and/or downloaded.

The presentation may be a presentation in an audio-visual way (e.g. using combination of visual, graphics, text, symbols, color, shades, video, animation, sound, speech, audio, etc.), graphical way (e.g. using GUI, animation, video), textual way (e.g. webpage with text, message, animated text), symbolic way (e.g. emoticon, signs, hand gesture), or mechanical way (e.g. vibration, actuator movement, haptics, etc.).

Basic Computation

Computational workload associated with the method is shared among the processor, the Type 1 heterogeneous wireless device, the Type 2 heterogeneous wireless device, a local server (e.g. hub device), a cloud server, and another processor.

An operation, pre-processing, processing and/or postprocessing may be applied to data (e.g. TSCI, autocorrelation, features of TSCI). An operation may be preprocessing, processing and/or postprocessing. The preprocessing, processing and/or postprocessing may be an operation. An operation may comprise preprocessing, processing, postprocessing, scaling, computing a confidence factor, computing a line-of-sight (LOS) quantity, computing a non-LOS (NLOS) quantity, a quantity comprising LOS and NLOS, computing a single link (e.g. path, communication path, link between a transmitting antenna and a receiving antenna) quantity, computing a quantity comprising multiple links, computing a function of the operands, filtering, linear filtering, nonlinear filtering, folding, grouping, energy computation, lowpass filtering, bandpass filtering, highpass filtering, median filtering, rank filtering, quartile filtering, percentile filtering, mode filtering, finite impulse response (FIR) filtering, infinite impulse response (IIR) filtering, moving average (MA) filtering, autoregressive (AR) filtering, autoregressive moving averaging (ARMA) filtering, selective filtering, adaptive filtering, interpolation, decimation, subsampling, upsampling, resampling, time correction, time base correction, phase correction, magnitude correction, phase cleaning, magnitude cleaning, matched filtering, enhancement, restoration, denoising, smoothing, signal conditioning, enhancement, restoration, spectral analysis, linear transform, nonlinear transform, inverse transform, frequency transform, inverse frequency transform, Fourier transform (FT), discrete time FT (DTFT), discrete FT (DFT), fast FT (FFT), wavelet transform, Laplace transform, Hilbert transform, Hadamard transform, trigonometric transform, sine transform, cosine transform, DCT, power-of-2 transform, sparse transform, graph-based transform, graph signal processing, fast transform, a transform combined with zero padding, cyclic padding, padding, zero padding, feature extraction, decomposition, projection, orthogonal projection, non-orthogonal projection, over-complete projection, eigen-decomposition, singular value decomposition (SVD), principle component analysis (PCA), independent component analysis (ICA), grouping, sorting, thresholding, soft thresholding, hard thresholding, clipping, soft clipping, first derivative, second order derivative, high order derivative, convolution, multiplication, division, addition, subtraction, integration, maximization, minimization, least mean square error, recursive least square, constrained least square, batch least square, least absolute error, least mean square deviation, least absolute deviation, local maximization, local minimization, optimization of a cost function, neural network, recognition, labeling, training, clustering, machine learning, supervised learning, unsupervised learning, semi-supervised learning, comparison with another TSCI, similarity score computation, quantization, vector quantization, matching pursuit, compression, encryption, coding, storing, transmitting, normalization, temporal normalization, frequency domain normalization, classification, clustering, labeling, tagging, learning, detection, estimation, learning network, mapping, remapping, expansion, storing, retrieving, transmitting, receiving, representing, merging, combining, splitting, tracking, monitoring, matched filtering, Kalman filtering, particle filter, intrapolation, extrapolation, histogram estimation, importance sampling, Monte Carlo sampling, compressive sensing, representing, merging, combining, splitting, scrambling, error protection, forward error correction, doing nothing, time varying processing, conditioning averaging, weighted averaging, arithmetic mean, geometric mean, harmonic mean, averaging over selected frequency, averaging over antenna links, logical operation, permutation, combination, sorting, AND, OR, XOR, union, intersection, vector addition, vector subtraction, vector multiplication, vector division, inverse, norm, distance, and/or another operation. The operation may be the preprocessing, processing, and/or post-processing. Operations may be applied jointly on multiple time series or functions.

The function (e.g. function of operands) may comprise: scalar function, vector function, discrete function, continuous function, polynomial function, characteristics, feature, magnitude, phase, exponential function, logarithmic function, trigonometric function, transcendental function, logical function, linear function, algebraic function, nonlinear function, piecewise linear function, real function, complex function, vector-valued function, inverse function, derivative of function, integration of function, circular function, function of another function, one-to-one function, one-to-many function, many-to-one function, many-to-many function, zero crossing, absolute function, indicator function, mean, mode, median, range, statistics, histogram, variance, standard deviation, measure of variation, spread, dispersion, deviation, divergence, range, interquartile range, total variation, absolute deviation, total deviation, arithmetic mean, geometric mean, harmonic mean, trimmed mean, percentile, square, cube, root, power, sine, cosine, tangent, cotangent, secant, cosecant, elliptical function, parabolic function, hyperbolic function, game function, zeta function, absolute value, thresholding, limiting function, floor function, rounding function, sign function, quantization, piecewise constant function, composite function, function of function, time function processed with an operation (e.g. filtering), probabilistic function, stochastic function, random function, ergodic function, stationary function, deterministic function, periodic function, repeated function, transformation, frequency transform, inverse frequency transform, discrete time transform, Laplace transform, Hilbert transform, sine transform, cosine transform, triangular transform, wavelet transform, integer transform, power-of-2 transform, sparse transform, projection, decomposition, principle component analysis (PCA), independent component analysis (ICA), neural network, feature extraction, moving function, function of moving window of neighboring items of time series, filtering function, convolution, mean function, histogram, variance/standard deviation function, statistical function, short-time transform, discrete transform, discrete Fourier transform, discrete cosine transform, discrete sine transform, Hadamard transform, eigen-decomposition, eigenvalue, singular value decomposition (SVD), singular value, orthogonal decomposition, matching pursuit, sparse transform, sparse approximation, any decomposition, graph-based processing, graph-based transform, graph signal processing, classification, identifying a class/group/category, labeling, learning, machine learning, detection, estimation, feature extraction, learning network, feature extraction, denoising, signal enhancement, coding, encryption, mapping, remapping, vector quantization, lowpass filtering, highpass filtering, bandpass filtering, matched filtering, Kalman filtering, preprocessing, postprocessing, particle filter, FIR filtering, IIR filtering, autoregressive (AR) filtering, adaptive filtering, first order derivative, high order derivative, integration, zero crossing, smoothing, median filtering, mode filtering, sampling, random sampling, resampling function, downsampling, down-converting, upsampling, up-converting, interpolation, extrapolation, importance sampling, Monte Carlo sampling, compressive sensing, statistics, short term statistics, long term statistics, autocorrelation function, cross correlation, moment generating function, time averaging, weighted averaging, special function, Bessel function, error function, complementary error function, Beta function, Gamma function, integral function, Gaussian function, Poisson function, etc.

Machine learning, training, discriminative training, deep learning, neural network, continuous time processing, distributed computing, distributed storage, acceleration using GPU/DSP/coprocessor/multicore/multiprocessing may be applied to a step (or each step) of this disclosure.

A frequency transform may include Fourier transform, Laplace transform, Hadamard transform, Hilbert transform, sine transform, cosine transform, triangular transform, wavelet transform, integer transform, power-of-2 transform, combined zero padding and transform, Fourier transform with zero padding, and/or another transform. Fast versions and/or approximated versions of the transform may be performed. The transform may be performed using floating point, and/or fixed point arithmetic.

An inverse frequency transform may include inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, inverse Fourier transform with zero padding, and/or another transform. Fast versions and/or approximated versions of the transform may be performed. The transform may be performed using floating point, and/or fixed point arithmetic.

A quantity/feature from a TSCI may be computed. The quantity may comprise statistic of at least one of: motion, location, map coordinate, height, speed, acceleration, movement angle, rotation, size, volume, time trend, pattern, one-time pattern, repeating pattern, evolving pattern, time pattern, mutually excluding patterns, related/correlated patterns, cause-and-effect, correlation, short-term/long-term correlation, tendency, inclination, statistics, typical behavior, atypical behavior, time trend, time profile, periodic motion, repeated motion, repetition, tendency, change, abrupt change, gradual change, frequency, transient, breathing, gait, action, event, suspicious event, dangerous event, alarming event, warning, belief, proximity, collision, power, signal, signal power, signal strength, signal intensity, received signal strength indicator (RSSI), signal amplitude, signal phase, signal frequency component, signal frequency band component, channel state information (CSI), map, time, frequency, time-frequency, decomposition, orthogonal decomposition, non-orthogonal decomposition, tracking, breathing, heart beat, statistical parameters, cardiopulmonary statistics/analytics (e.g. output responses), daily activity statistics/analytics, chronic disease statistics/analytics, medical statistics/analytics, an early (or instantaneous or contemporaneous or delayed) indication/suggestion/sign/indicator/verifier/detection/symptom of a disease/condition/situation, biometric, baby, patient, machine, device, temperature, vehicle, parking lot, venue, lift, elevator, spatial, road, fluid flow, home, room, office, house, building, warehouse, storage, system, ventilation, fan, pipe, duct, people, human, car, boat, truck, airplane, drone, downtown, crowd, impulsive event, cyclo-stationary, environment, vibration, material, surface, 3-dimensional, 2-dimensional, local, global, presence, and/or another measurable quantity/variable.

Sliding Window/Algorithm

Sliding time window may have time varying window width. It may be smaller at the beginning to enable fast acquisition and may increase over time to a steady-state size. The steady-state size may be related to the frequency, repeated motion, transient motion, and/or STI to be monitored. Even in steady state, the window size may be adaptively (and/or dynamically) changed (e.g. adjusted, varied, modified) based on battery life, power consumption, available computing power, change in amount of targets, the nature of motion to be monitored, etc.

The time shift between two sliding time windows at adjacent time instance may be constant/variable/locally adaptive/dynamically adjusted over time. When shorter time shift is used, the update of any monitoring may be more frequent which may be used for fast changing situations, object motions, and/or objects. Longer time shift may be used for slower situations, object motions, and/or objects.

The window width/size and/or time shift may be changed (e.g. adjusted, varied, modified) upon a user request/choice. The time shift may be changed automatically (e.g. as controlled by processor/computer/server/hub device/cloud server) and/or adaptively (and/or dynamically).

At least one characteristics (e.g. characteristic value, or characteristic point) of a function (e.g. auto-correlation function, auto-covariance function, cross-correlation function, cross-covariance function, power spectral density, time function, frequency domain function, frequency transform) may be determined (e.g. by an object tracking server, the processor, the Type 1 heterogeneous device, the Type 2 heterogeneous device, and/or another device). The at least one characteristics of the function may include: a maximum, minimum, extremum, local maximum, local minimum, local extremum, local extremum with positive time offset, first local extremum with positive time offset, n^th local extremum with positive time offset, local extremum with negative time offset, first local extremum with negative time offset, n^th local extremum with negative time offset, constrained maximum, constrained minimum, constrained extremum, significant maximum, significant minimum, significant extremum, slope, derivative, higher order derivative, maximum slope, minimum slope, local maximum slope, local maximum slope with positive time offset, local minimum slope, constrained maximum slope, constrained minimum slope, maximum higher order derivative, minimum higher order derivative, constrained higher order derivative, zero-crossing, zero crossing with positive time offset, n^th zero crossing with positive time offset, zero crossing with negative time offset, n^th zero crossing with negative time offset, constrained zero-crossing, zero-crossing of slope, zero-crossing of higher order derivative, and/or another characteristics. At least one argument of the function associated with the at least one characteristics of the function may be identified. Some quantity (e.g. spatial-temporal information of the object) may be determined based on the at least one argument of the function.

A characteristics (e.g. characteristics of motion of an object in the venue) may comprise at least one of: an instantaneous characteristics, short-term characteristics, repetitive characteristics, recurring characteristics, history, incremental characteristics, changing characteristics, deviational characteristics, phase, magnitude, degree, time characteristics, frequency characteristics, time-frequency characteristics, decomposition characteristics, orthogonal decomposition characteristics, non-orthogonal decomposition characteristics, deterministic characteristics, probabilistic characteristics, stochastic characteristics, autocorrelation function (ACF), mean, variance, standard deviation, measure of variation, spread, dispersion, deviation, divergence, range, interquartile range, total variation, absolute deviation, total deviation, statistics, duration, timing, trend, periodic characteristics, repetition characteristics, long-term characteristics, historical characteristics, average characteristics, current characteristics, past characteristics, future characteristics, predicted characteristics, location, distance, height, speed, direction, velocity, acceleration, change of the acceleration, angle, angular speed, angular velocity, angular acceleration of the object, change of the angular acceleration, orientation of the object, angular of rotation, deformation of the object, shape of the object, change of shape of the object, change of size of the object, change of structure of the object, and/or change of characteristics of the object.

At least one local maximum and at least one local minimum of the function may be identified. At least one local signal-to-noise-ratio-like (SNR-like) parameter may be computed for each pair of adjacent local maximum and local minimum. The SNR-like parameter may be a function (e.g. linear, log, exponential function, monotonic function) of a fraction of a quantity (e.g. power, magnitude) of the local maximum over the same quantity of the local minimum. It may also be the function of a difference between the quantity of the local maximum and the same quantity of the local minimum. Significant local peaks may be identified or selected. Each significant local peak may be a local maximum with SNR-like parameter greater than a threshold T1 and/or a local maximum with amplitude greater than a threshold T2. The at least one local minimum and the at least one local minimum in the frequency domain may be identified/computed using a persistence-based approach.

A set of selected significant local peaks may be selected from the set of identified significant local peaks based on a selection criterion (e.g. a quality criterion, a signal quality condition). The characteristics/STI of the object may be computed based on the set of selected significant local peaks and frequency values associated with the set of selected significant local peaks. In one example, the selection criterion may always correspond to select the strongest peaks in a range. While the strongest peaks may be selected, the unselected peaks may still be significant (rather strong).

Unselected significant peaks may be stored and/or monitored as "reserved" peaks for use in future selection in future sliding time windows. As an example, there may be a particular peak (at a particular frequency) appearing consistently over time. Initially, it may be significant but not selected (as other peaks may be stronger). But in later time, the peak may become stronger and more dominant and may be selected. When it became "selected", it may be back-traced in time and made "selected" in the earlier time when it was significant but not selected. In such case, the back-traced peak may replace a previously selected peak in an early time. The replaced peak may be the relatively weakest, or a peak that appear in isolation in time (i.e. appearing only briefly in time).

In another example, the selection criterion may not correspond to select the strongest peaks in the range. Instead, it may consider not only the "strength" of the peak, but the "trace" of the peak—peaks that may have happened in the past, especially those peaks that have been identified for a long time.

For example, if a finite state machine (FSM) is used, it may select the peak(s) based on the state of the FSM. Decision thresholds may be computed adaptively (and/or dynamically) based on the state of the FSM.

A similarity score and/or component similarity score may be computed (e.g. by a server (e.g. hub device), the processor, the Type 1 device, the Type 2 device, a local server, a cloud server, and/or another device) based on a pair of temporally adjacent CI of a TSCI. The pair may come from the same sliding window or two different sliding windows. The similarity score may also be based on a pair of, temporally adjacent or not so adjacent, CI from two different TSCI. The similarity score and/or component similar score may be/comprise: time reversal resonating strength (TRRS), correlation, cross-correlation, auto-correlation, correlation indicator, covariance, cross-covariance, auto-covariance, inner product of two vectors, distance score, norm, metric, quality metric, signal quality condition, statistical characteristics, discrimination score, neural network, deep learning network, machine learning, training, discrimination, weighted averaging, preprocessing, denoising, signal conditioning, filtering, time correction, timing compensation, phase offset compensation, transformation, component-wise operation, feature extraction, finite state machine, and/or another score. The characteristics and/or STI may be determined/computed based on the similarity score.

Any threshold may be pre-determined, adaptively (and/or dynamically) determined and/or determined by a finite state machine. The adaptive determination may be based on time, space, location, antenna, path, link, state, battery life, remaining battery life, available power, available computational resources, available network bandwidth, etc.

A threshold to be applied to a test statistics to differentiate two events (or two conditions, or two situations, or two states), A and B, may be determined. Data (e.g. CI, channel state information (CSI), power parameter) may be collected under A and/or under B in a training situation. The test statistics may be computed based on the data. Distributions of the test statistics under A may be compared with distributions of the test statistics under B (reference distribution), and the threshold may be chosen according to some criteria. The criteria may comprise: maximum likelihood (ML), maximum aposterior probability (MAP), discriminative training, minimum Type 1 error for a given Type 2 error, minimum Type 2 error for a given Type 1 error, and/or other criteria (e.g. a quality criterion, signal quality condition). The threshold may be adjusted to achieve different sensitivity to the A, B and/or another event/condition/situation/state. The threshold adjustment may be automatic, semi-automatic and/or manual. The threshold adjustment may be applied once, sometimes, often, periodically, repeatedly, occasionally, sporadically, and/or on demand. The threshold adjustment may be adaptive (and/or dynamically adjusted). The threshold adjustment may depend on the object, object movement/location/direction/action, object characteristics/ STI/size/property/trait/habit/behavior, the venue, feature/ fixture/furniture/barrier/material/machine/living thing/ thing/object/boundary/surface/medium that is in/at/of the venue, map, constraint of the map (or environmental model), the event/state/situation/condition, time, timing, duration, current state, past history, user, and/or a personal preference, etc.

A stopping criterion (or skipping or bypassing or blocking or pausing or passing or rejecting criterion) of an iterative algorithm may be that change of a current parameter (e.g. offset value) in the updating in an iteration is less than a threshold. The threshold may be 0.5, 1, 1.5, 2, or another number. The threshold may be adaptive (and/or dynamically adjusted). It may change as the iteration progresses. For the offset value, the adaptive threshold may be determined based on the task, particular value of the first time, the current time offset value, the regression window, the regression analysis, the regression function, the regression error, the convexity of the regression function, and/or an iteration number.

The local extremum may be determined as the corresponding extremum of the regression function in the regression window. The local extremum may be determined based on a set of time offset values in the regression window and a set of associated regression function values. Each of the set of associated regression function values associated with the set of time offset values may be within a range from the corresponding extremum of the regression function in the regression window.

The searching for a local extremum may comprise robust search, minimization, maximization, optimization, statistical optimization, dual optimization, constraint optimization, convex optimization, global optimization, local optimization an energy minimization, linear regression, quadratic regression, higher order regression, linear programming, nonlinear programming, stochastic programming, combinatorial optimization, constraint programming, constraint satisfaction, calculus of variations, optimal control, dynamic programming, mathematical programming, multi-objective optimization, multi-modal optimization, disjunctive programming, space mapping, infinite-dimensional optimization, heuristics, metaheuristics, convex programming, semidefinite programming, conic programming, cone programming, integer programming, quadratic programming, fractional programming, numerical analysis, simplex algorithm, iterative method, gradient descent, subgradient method, coordinate descent, conjugate gradient method, Newton's algorithm, sequential quadratic programming, interior point method, ellipsoid method, reduced gradient method, quasi-Newton method, simultaneous perturbation stochastic approximation, interpolation method, pattern search method, line search, non-differentiable optimization, genetic algorithm, evolutionary algorithm, dynamic relaxation, hill climbing, particle swarm optimization, gravitation search algorithm, simulated annealing, memetic algorithm, differential evolution, dynamic relaxation, stochastic tunneling, Tabu search, reactive search optimization, curve fitting, least square, simulation based optimization, variational calculus, and/or variant. The search for local extremum may be associated with an objective function, loss function, cost function, utility function, fitness function, energy function, and/or an energy function.

Regression may be performed using regression function to fit sampled data (e.g. CI, feature of CI, component of CI) or another function (e.g. autocorrelation function) in a regression window. In at least one iteration, a length of the regression window and/or a location of the regression window may change. The regression function may be linear function, quadratic function, cubic function, polynomial function, and/or another function.

The regression analysis may minimize at least one of: error, aggregate error, component error, error in projection domain, error in selected axes, error in selected orthogonal axes, absolute error, square error, absolute deviation, square deviation, higher order error (e.g. third order, fourth order), robust error (e.g. square error for smaller error magnitude and absolute error for larger error magnitude, or first kind of error for smaller error magnitude and second kind of error for larger error magnitude), another error, weighted sum (or weighted mean) of absolute/square error (e.g. for wireless transmitter with multiple antennas and wireless receiver with multiple antennas, each pair of transmitter antenna and receiver antenna form a link), mean absolute error, mean square error, mean absolute deviation, and/or mean square deviation. Error associated with different links may have different weights. One possibility is that some links and/or some components with larger noise or lower signal quality metric may have smaller or bigger weight.), weighted sum of square error, weighted sum of higher order error, weighted sum of robust error, weighted sum of the another error, absolute cost, square cost, higher order cost, robust cost, another cost, weighted sum of absolute cost, weighted sum of square cost, weighted sum of higher order cost, weighted sum of robust cost, and/or weighted sum of another cost.

The regression error determined may be an absolute error, square error, higher order error, robust error, yet another error, weighted sum of absolute error, weighted sum of square error, weighted sum of higher order error, weighted sum of robust error, and/or weighted sum of the yet another error.

The time offset associated with maximum regression error (or minimum regression error) of the regression function with respect to the particular function in the regression window may become the updated current time offset in the iteration.

A local extremum may be searched based on a quantity comprising a difference of two different errors (e.g. a difference between absolute error and square error). Each of the two different errors may comprise an absolute error, square error, higher order error, robust error, another error, weighted sum of absolute error, weighted sum of square error, weighted sum of higher order error, weighted sum of robust error, and/or weighted sum of the another error.

The quantity may be compared with a reference data or a reference distribution, such as an F-distribution, central F-distribution, another statistical distribution, threshold, threshold associated with probability/histogram, threshold associated with probability/histogram of finding false peak, threshold associated with the F-distribution, threshold associated the central F-distribution, and/or threshold associated with the another statistical distribution.

The regression window may be determined based on at least one of: the movement (e.g. change in position/location) of the object, quantity associated with the object, the at least one characteristics and/or STI of the object associated with the movement of the object, estimated location of the local extremum, noise characteristics, estimated noise characteristics, signal quality metric, F-distribution, central F-distribution, another statistical distribution, threshold, preset threshold, threshold associated with probability/histogram, threshold associated with desired probability, threshold associated with probability of finding false peak, threshold associated with the F-distribution, threshold associated the central F-distribution, threshold associated with the another statistical distribution, condition that quantity at the window center is largest within the regression window, condition that the quantity at the window center is largest within the regression window, condition that there is only one of the local extremum of the particular function for the particular value of the first time in the regression window, another regression window, and/or another condition.

The width of the regression window may be determined based on the particular local extremum to be searched. The local extremum may comprise first local maximum, second local maximum, higher order local maximum, first local maximum with positive time offset value, second local maximum with positive time offset value, higher local maximum with positive time offset value, first local maximum with negative time offset value, second local maximum with negative time offset value, higher local maximum with negative time offset value, first local minimum, second local minimum, higher local minimum, first local minimum with positive time offset value, second local minimum with positive time offset value, higher local minimum with positive time offset value, first local minimum with negative time offset value, second local minimum with negative time offset value, higher local minimum with negative time offset value, first local extremum, second local extremum, higher local extremum, first local extremum with positive time offset value, second local extremum with positive time offset value, higher local extremum with positive time offset value, first local extremum with negative time offset value, second local extremum with negative time offset value, and/or higher local extremum with negative time offset value.

A current parameter (e.g. time offset value) may be initialized based on a target value, target profile, trend, past trend, current trend, target speed, speed profile, target speed profile, past speed trend, the motion or movement (e.g. change in position/location) of the object, at least one characteristics and/or STI of the object associated with the movement of object, positional quantity of the object, initial speed of the object associated with the movement of the object, predefined value, initial width of the regression window, time duration, value based on carrier frequency of the signal, value based on subcarrier frequency of the signal, bandwidth of the signal, amount of antennas associated with the channel, noise characteristics, signal h metric, and/or an adaptive (and/or dynamically adjusted) value. The current time offset may be at the center, on the left side, on the right side, and/or at another fixed relative location, of the regression window.

In the presentation, information may be displayed with a map (or environmental model) of the venue. The information may comprise: location, zone, region, area, coverage area, corrected location, approximate location, location with respect to (w.r.t.) a map of the venue, location w.r.t. a segmentation of the venue, direction, path, path w.r.t. the map and/or the segmentation, trace (e.g. location within a time window such as the past 5 seconds, or past 10 seconds; the time window duration may be adjusted adaptively (and/or dynamically); the time window duration may be adaptively (and/or dynamically) adjusted w.r.t. speed, acceleration, etc.), history of a path, approximate regions/zones along a path, history/summary of past locations, history of past locations of interest, frequently-visited areas, customer traffic, crowd distribution, crowd behavior, crowd control information, speed, acceleration, motion statistics, breathing rate, heart rate, presence/absence of motion, presence/absence of people or pets or object, presence/absence of vital sign, gesture, gesture control (control of devices using gesture), location-based gesture control, information of a location-based operation, identity (ID) or identifier of the respect object (e.g. pet, person, self-guided machine/device, vehicle, drone, car, boat, bicycle, self-guided vehicle, machine with fan, air-conditioner, TV, machine with movable part), identification of a user (e.g. person), information of the user, location/speed/acceleration/direction/motion/gesture/gesture control/motion trace of the user, ID or identifier of the user, activity of the user, state of the user, sleeping/resting characteristics of the user, emotional state of the user, vital sign of the user, environment information of the venue, weather information of the venue, earthquake, explosion, storm, rain, fire, temperature, collision, impact, vibration, event, door-open event, door-close event, window-open event, window-close event, fall-down event, burning event, freezing event, water-related event, wind-related event, air-movement event, accident event, pseudo-periodic event (e.g. running on treadmill, jumping up and down, skipping rope, somersault, etc.), repeated event, crowd event, vehicle event, gesture of the user (e.g. hand gesture, arm gesture, foot gesture, leg gesture, body gesture, head gesture, face gesture, mouth gesture, eye gesture, etc.).

The location may be 2-dimensional (e.g. with 2D coordinates), 3-dimensional (e.g. with 3D coordinates). The location may be relative (e.g. w.r.t. a map or environmental model) or relational (e.g. halfway between point A and point B, around a corner, up the stairs, on top of table, at the ceiling, on the floor, on a sofa, close to point A, a distance R from point A, within a radius of R from point A, etc.). The location may be expressed in rectangular coordinate, polar coordinate, and/or another representation.

The information (e.g. location) may be marked with at least one symbol. The symbol may be time varying. The symbol may be flashing and/or pulsating with or without changing color/intensity. The size may change over time. The orientation of the symbol may change over time. The symbol may be a number that reflects an instantaneous quantity (e.g. vital sign/breathing rate/heart rate/gesture/state/status/action/motion of a user, temperature, network traffic, network connectivity, status of a device/machine, remaining power of a device, status of the device, etc.). The rate of change, the size, the orientation, the color, the intensity and/or the symbol may reflect the respective motion. The information may be presented visually and/or described verbally (e.g. using pre-recorded voice, or voice synthesis). The information may be described in text. The information may also be presented in a mechanical way (e.g. an animated gadget, a movement of a movable part).

The user-interface (UI) device may be a smart phone (e.g. iPhone, Android phone), tablet (e.g. iPad), laptop (e.g. notebook computer), personal computer (PC), device with graphical user interface (GUI), smart speaker, device with voice/audio/speaker capability, virtual reality (VR) device, augmented reality (AR) device, smart car, display in the car, voice assistant, voice assistant in a car, etc.

The map (or environmental model) may be 2-dimensional, 3-dimensional and/or higher-dimensional. (e.g. a time varying 2D/3D map/environmental model) Walls, windows, doors, entrances, exits, forbidden areas may be marked on the map or the model. The map may comprise floor plan of a facility. The map or model may have one or more layers (overlays). The map/model may be a maintenance map/model comprising water pipes, gas pipes, wiring, cabling, air ducts, crawl-space, ceiling layout, and/or underground layout. The venue may be segmented/subdivided/zoned/grouped into multiple zones/regions/geographic regions/sectors/sections/territories/districts/precincts/localities/neighborhoods/areas/stretches/expanse such as bedroom, living room, storage room, walkway, kitchen, dining room, foyer, garage, first floor, second floor, rest room, offices, conference room, reception area, various office areas, various warehouse regions, various facility areas, etc. The segments/regions/areas may be presented in a map/model. Different regions may be color-coded. Different regions may be presented with a characteristic (e.g. color, brightness, color intensity, texture, animation, flashing, flashing rate, etc.). Logical segmentation of the venue may be done using the at least one heterogeneous Type 2 device, or a server (e.g. hub device), or a cloud server, etc.

Here is an example of the disclosed system, apparatus, and method. Stephen and his family want to install the disclosed wireless motion detection system to detect motion in their 2000 sqft two-storey town house in Seattle, Washington Because his house has two storeys, Stephen decided to use one Type 2 device (named A) and two Type 1 devices (named B and C) in the ground floor. His ground floor has predominantly three rooms: kitchen, dining room and living room arranged in a straight line, with the dining room in the middle. The kitchen and the living rooms are on opposite end of the house. He put the Type 2 device (A) in the dining room, and put one Type 1 device (B) in the kitchen and the other Type 1 device (C) in the living room. With this placement of the devices, he is practically partitioning the ground floor into 3 zones (dining room, living room and kitchen) using the motion detection system. When motion is detected by the AB pair and the AC pair, the system would analyze the motion information and associate the motion with one of the 3 zones.

When Stephen and his family go out on weekends (e.g. to go for a camp during a long weekend), Stephen would use a mobile phone app (e.g. Android phone app or iPhone app) to turn on the motion detection system. When the system detects motion, a warning signal is sent to Stephen (e.g. an SMS text message, an email, a push message to the mobile phone app, etc.). If Stephen pays a monthly fee (e.g. $10/month), a service company (e.g. security company) will receive the warning signal through wired network (e.g. broadband) or wireless network (e.g. home WiFi, LTE, 3G, 2.5G, etc.) and perform a security procedure for Stephen (e.g. call him to verify any problem, send someone to check on the house, contact the police on behalf of Stephen, etc.). Stephen loves his aging mother and cares about her well-being when she is alone in the house. When the mother is alone in the house while the rest of the family is out (e.g. go to work, or shopping, or go on vacation), Stephen would turn on the motion detection system using his mobile app to ensure the mother is ok. He then uses the mobile app to monitor his mother's movement in the house. When Stephen uses the mobile app to see that the mother is moving around the house among the 3 regions, according to her daily routine, Stephen knows that his mother is doing ok. Stephen is thankful that the motion detection system can help him monitor his mother's well-being while he is away from the house.

On a typical day, the mother would wake up at around 7 AM. She would cook her breakfast in the kitchen for about 20 minutes. Then she would eat the breakfast in the dining room for about 30 minutes. Then she would do her daily exercise in the living room, before sitting down on the sofa in the living room to watch her favorite TV show. The motion detection system enables Stephen to see the timing of the movement in each of the 3 regions of the house. When the motion agrees with the daily routine, Stephen knows roughly that the mother should be doing fine. But when the motion pattern appears abnormal (e.g. there is no motion until 10 AM, or she stayed in the kitchen for too long, or she remains motionless for too long, etc.), Stephen suspects something is wrong and would call the mother to check on her. Stephen may even get someone (e.g. a family member, a neighbor, a paid personnel, a friend, a social worker, a service provider) to check on his mother.

At some time, Stephen feels like repositioning the Type 2 device. He simply unplugs the device from the original AC power plug and plug it into another AC power plug. He is happy that the wireless motion detection system is plug-and-play and the repositioning does not affect the operation of the system. Upon powering up, it works right away.

Sometime later, Stephen is convinced that our wireless motion detection system can really detect motion with very high accuracy and very low alarm, and he really can use the mobile app to monitor the motion in the ground floor. He decides to install a similar setup (i.e. one Type 2 device and two Type 1 devices) in the second floor to monitor the bedrooms in the second floor. Once again, he finds that the system set up is extremely easy as he simply needs to plug the Type 2 device and the Type 1 devices into the AC power plug in the second floor. No special installation is needed. And he can use the same mobile app to monitor motion in the ground floor and the second floor. Each Type 2 device in the ground floor/second floor can interact with all the Type 1 devices in both the ground floor and the second floor. Stephen is happy to see that, as he doubles his investment in the Type 1 and Type 2 devices, he has more than double the capability of the combined systems.

According to various embodiments, each CI (CI) may comprise at least one of: channel state information (CSI), frequency domain CSI, frequency representation of CSI, frequency domain CSI associated with at least one sub-band, time domain CSI, CSI in domain, channel response, estimated channel response, channel impulse response (CIR), channel frequency response (CFR), channel characteristics, channel filter response, CSI of the wireless multipath channel, information of the wireless multipath channel, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another CI. In one embodiment, the disclosed system has hardware components (e.g. wireless transmitter/receiver with antenna, analog circuitry, power supply, processor, memory) and corresponding software components. According to various embodiments of the present teaching, the disclosed system includes Bot (referred to as a Type 1 device) and Origin (referred to as a Type 2 device) for vital sign detection and monitoring. Each device comprises a transceiver, a processor and a memory.

The disclosed system can be applied in many cases. In one example, the Type 1 device (transmitter) may be a small WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. In one example, the Type 2 (receiver) may be a WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. The Type 1 device and Type 2 devices may be placed in/near a conference room to count people. The Type 1 device and Type 2 devices may be in a well-being monitoring system for older adults to monitor their daily activities and any sign of symptoms (e.g. dementia, Alzheimer's disease). The Type 1 device and Type 2 device may be used in baby monitors to monitor the vital signs (breathing) of a living baby. The Type 1 device and Type 2 devices may be placed in bedrooms to monitor quality of sleep and any sleep apnea. The Type 1 device and Type 2 devices may be placed in cars to monitor well-being of passengers and driver, detect any sleeping of driver and detect any babies left in a car. The Type 1 device and Type 2 devices may be used in logistics to prevent human trafficking by monitoring any human hidden in trucks and containers. The Type 1 device and Type 2 devices may be deployed by emergency service at disaster area to search for trapped victims in debris. The Type 1 device and Type 2 devices may be deployed in an area to detect breathing of any intruders. There are numerous applications of wireless breathing monitoring without wearables.

Hardware modules may be constructed to contain the Type 1 transceiver and/or the Type 2 transceiver. The hardware modules may be sold to/used by variable brands to design, build and sell final commercial products. Products using the disclosed system and/or method may be home/office security products, sleep monitoring products, WiFi products, mesh products, TV, STB, entertainment system, HiFi, speaker, home appliance, lamps, stoves, oven, microwave oven, table, chair, bed, shelves, tools, utensils, torches, vacuum cleaner, smoke detector, sofa, piano, fan, door, window, door/window handle, locks, smoke detectors, car accessories, computing devices, office devices, air conditioner, heater, pipes, connectors, surveillance camera, access point, computing devices, mobile devices, LTE devices, 3G/4G/5G/6G devices, UMTS devices, 3GPP devices, GSM devices, EDGE devices, TDMA devices, FDMA devices, CDMA devices, WCDMA devices, TD-SCDMA devices, gaming devices, eyeglasses, glass panels, VR goggles, necklace, watch, waist band, belt, wallet, pen, hat, wearables, implantable device, tags, parking tickets, smart phones, etc.

The summary may comprise: analytics, output response, selected time window, subsampling, transform, and/or projection. The presenting may comprise presenting at least one of: monthly/weekly/daily view, simplified/detailed view, cross-sectional view, small/large form-factor view, color-coded view, comparative view, summary view, animation, web view, voice announcement, and another presentation related to the periodic/repetition characteristics of the repeating motion.

A Type 1/Type 2 device may be an antenna, a device with antenna, a device with a housing (e.g. for radio, antenna, data/signal processing unit, wireless IC, circuits), device that has interface to attach/connect to/link antenna, device that is interfaced to/attached to/connected to/linked to another device/system/computer/phone/network/data aggregator, device with a user interface (UI)/graphical UI/display, device with wireless transceiver, device with wireless transmitter, device with wireless receiver, internet-of-thing (IoT) device, device with wireless network, device with both wired networking and wireless networking capability, device with wireless integrated circuit (IC), Wi-Fi device, device with Wi-Fi chip (e.g. 802.11a/b/g/n/ac/ax standard compliant), Wi-Fi access point (AP), Wi-Fi client, Wi-Fi router, Wi-Fi repeater, Wi-Fi hub, Wi-Fi mesh network router/hub/AP, wireless mesh network router, adhoc network device, wireless mesh network device, mobile device (e.g. 2G/2.5G/3G/3.5G/4G/LTF/5G/6G/G, UMTS, 3GPP, GSM, EDGE, TDMA, FDMA, CDMA, WCDMA, TD-SCDMA), cellular device, base station, mobile network base station, mobile network hub, mobile network compatible device, LTE device, device with LTE module, mobile module (e.g. circuit board with mobile-enabling chip (IC) such as Wi-Fi chip, LTE chip, BLE chip), Wi-Fi chip (IC), LTE chip, BLE chip, device with mobile module, smart phone, companion device (e.g. dongle, attachment, plugin) for smart phones, dedicated device, plug-in device, AC-powered device, battery-powered device, device with processor/memory/set of instructions, smart device/gadget/items: clock, stationary, pen, user-interface, paper, mat, camera, television (TV), set-top-box, microphone, speaker, refrigerator, oven, machine, phone, wallet, furniture, door, window, ceiling, floor, wall, table, chair, bed, night-stand, air-conditioner, heater, pipe, duct, cable, carpet, decoration, gadget, USB device, plug, dongle, lamp/light, tile, ornament, bottle, vehicle, car, AGV, drone, robot, laptop, tablet, computer, harddisk, network card, instrument, racket, ball, shoe, wearable, clothing, glasses, hat, necklace, food, pill, small device that moves in the body of creature (e.g. in blood vessels, in lymph fluid, digestive system), and/or another device. The Type 1 device and/or Type 2 device may be communicatively coupled with: the internet, another device with access to internet (e.g. smart phone), cloud server (e.g. hub device), edge server, local server, and/or storage. The Type 1 device and/or the Type 2 device may operate with local control, can be controlled by another device via a wired/wireless connection, can operate automatically, or can be controlled by a central system that is remote (e.g. away from home).

In one embodiment, a Type B device may be a transceiver that may perform as both Origin (a Type 2 device, a Rx device) and Bot (a Type 1 device, a Tx device), i.e., a Type B device may be both Type 1 (Tx) and Type 2 (Rx) devices (e.g. simultaneously or alternately), for example, mesh devices, a mesh router, etc. In one embodiment, a Type A device may be a transceiver that may only function as Bot (a Tx device), i.e., Type 1 device only or Tx only, e.g., simple IoT devices. It may have the capability of Origin (Type 2 device, Rx device), but somehow it is functioning only as Bot in the embodiment. All the Type A and Type B devices form a tree structure. The root may be a Type B device with network (e.g. internet) access. For example, it may be connected to broadband service through a wired connection (e.g. Ethernet, cable modem, ADSL/HDSL modem) connection or a wireless connection (e.g. LTE, 3G/4G/5G, WiFi, Bluetooth, microwave link, satellite link, etc.). In one embodiment, all the Type A devices are leaf node. Each Type B device may be the root node, non-leaf node, or leaf node.

Type 1 device (transmitter, or Tx) and Type 2 device (receiver, or Rx) may be on same device (e.g. RF chip/IC) or simply the same device. The devices may operate at high frequency band, such as 28 GHz, 60 GHz, 77 GHz, etc. The RF chip may have dedicated Tx antennas (e.g. 32 antennas) and dedicated Rx antennas (e.g. another 32 antennas).

One Tx antenna may transmit a wireless signal (e.g. a series of probe signal, perhaps at 100 Hz). Alternatively, all Tx antennas may be used to transmit the wireless signal with beamforming (in Tx), such that the wireless signal is focused in certain direction (e.g. for energy efficiency or boosting the signal to noise ratio in that direction, or low power operation when "scanning" that direction, or low power operation if object is known to be in that direction).

The wireless signal hits an object (e.g. a living human lying on a bed 4 feet away from the Tx/Rx antennas, with breathing and heart beat) in a venue (e.g. a room). The object motion (e.g. lung movement according to breathing rate, or blood-vessel movement according to heart beat) may impact/modulate the wireless signal. All Rx antennas may be used to receive the wireless signal.

Beamforming (in Rx and/or Tx) may be applied (digitally) to "scan" different directions. Many directions can be scanned or monitored simultaneously. With beamforming, "sectors" (e.g. directions, orientations, bearings, zones, regions, segments) may be defined related to the Type 2 device (e.g. relative to center location of antenna array). For each probe signal (e.g. a pulse, an ACK, a control packet, etc.), a channel information or CI (e.g. channel impulse response/CIR, CSI, CFR) is obtained/computed for each sector (e.g. from the RF chip). In breathing detection, one may collect CIR in a sliding window (e.g. 30 sec, and with 100 Hz sounding/probing rate, one may have 3000 CIR over 30 sec).

The CIR may have many taps (e.g. N1 components/taps). Each tap may be associated with a time lag, or a time-of-flight (tof, e.g. time to hit the human 4 feet away and back). When a person is breathing in a certain direction at a certain distance (e.g. 4 ft), one may search for the CIR in the "certain direction". Then one may search for the tap corresponding to the "certain distance". Then one may compute the breathing rate and heart rate from that tap of that CIR.

One may consider each tap in the sliding window (e.g. 30 second window of "component time series") as a time function (e.g. a "tap function", the "component time series"). One may examine each tap function in search of a strong periodic behavior (e.g. corresponds to breathing, perhaps in the range of 10 bpm to 40 bpm).

The Type 1 device and/or the Type 2 device may have external connections/links and/or internal connections/links. The external connections (e.g. connection 1110) may be associated with 2G/2.5G/3G/3.5G/4G/LTE/5G/6G/7G/NBIoT, UWB, WiMax, Zigbee, 802.16 etc. The internal connections (e.g., 1114A and 1114B, 1116, 1118, 1120) may be associated with WiFi, an IEEE 802.11 standard, 802.11a/b/g/n/ac/ad/af/ag/ah/ai/aj/aq/ax/ay, Bluetooth, Bluetooth 1.0/1.1/1.2/2.0/2.1/3.0/4.0/4.1/4.2/5, BLE, mesh network, an IEEE 802.16/1/1a/1b/2/2a/a/b/c/d/e/f/g/h/i/j/k/l/m/n/o/p/ standard.

The Type 1 device and/or Type 2 device may be powered by battery (e.g. AA battery, AAA battery, coin cell battery, button cell battery, miniature battery, bank of batteries, power bank, car battery, hybrid battery, vehicle battery, container battery, non-rechargeable battery, rechargeable battery, NiCd battery, NiMH battery, Lithium ion battery, Zinc carbon battery, Zinc chloride battery, lead acid battery, alkaline battery, battery with wireless charger, smart battery, solar battery, boat battery, plane battery, other battery, temporary energy storage device, capacitor, fly wheel).

Any device may be powered by DC or direct current (e.g. from battery as described above, power generator, power convertor, solar panel, rectifier, DC-DC converter, with various voltages such as 1.2V, 1.5V, 3V, 5V, 6V, 9V, 12V, 24V, 40V, 42V, 48V, 110V, 220V, 380V, etc.) and may thus have a DC connector or a connector with at least one pin for DC power.

Any device may be powered by AC or alternating current (e.g. wall socket in a home, transformer, invertor, shore-power, with various voltages such as 100V, 110V, 120V, 100-127V, 200V, 220V, 230V, 240V, 220-240V, 100-240V, 250V, 380V, 50 Hz, 60 Hz, etc.) and thus may have an AC connector or a connector with at least one pin for AC power. The Type 1 device and/or the Type 2 device may be positioned (e.g. installed, placed, moved to) in the venue or outside the venue.

For example, in a vehicle (e.g. a car, truck, lorry, bus, special vehicle, tractor, digger, excavator, teleporter, bulldozer, crane, forklift, electric trolley, AGV, emergency vehicle, freight, wagon, trailer, container, boat, ferry, ship, submersible, airplane, air-ship, lift, mono-rail, train, tram, rail-vehicle, railcar, etc.), the Type 1 device and/or Type 2 device may be an embedded device embedded in the vehicle, or an add-on device (e.g. aftermarket device) plugged into a port in the vehicle (e.g. OBD port/socket, USB port/socket, accessory port/socket, 12V auxiliary power outlet, and/or 12V cigarette lighter port/socket).

For example, one device (e.g. Type 2 device) may be plugged into 12V cigarette lighter/accessory port or OBD port or the USB port (e.g. of a car/truck/vehicle) while the other device (e.g. Type 1 device) may be plugged into 12V cigarette lighter/accessory port or the OBD port or the USB port. The OBD port and/or USB port can provide power, signaling and/or network (of the car/truck/vehicle). The two devices may jointly monitor the passengers including children/babies in the car. They may be used to count the passengers, recognize the driver, detect presence of passenger in a particular seat/position in the vehicle.

In another example, one device may be plugged into 12V cigarette lighter/accessory port or OBD port or the USB port of a car/truck/vehicle while the other device may be plugged into 12V cigarette lighter/accessory port or OBD port or the USB port of another car/truck/vehicle.

In another example, there may be many devices of the same type A (e.g. Type 1 or Type 2) in many heterogeneous vehicles/portable devices/smart gadgets (e.g. automated guided vehicle/AGV, shopping/luggage/moving cart, parking ticket, golf cart, bicycle, smart phone, tablet, camera, recording device, smart watch, roller skate, shoes, jackets, goggle, hat, eye-wear, wearable, Segway, scooter, luggage tag, cleaning machine, vacuum cleaner, pet tag/collar/wearable/implant), each device either plugged into 12V accessory port/OBD port/USB port of a vehicle or embedded in a vehicle. There may be one or more device of the other type B (e.g. B is Type 1 if A is Type 2, or B is Type 2 if A is Type 1) installed at locations such as gas stations, street lamp post, street corners, tunnels, multi-storey parking facility, scattered locations to cover a big area such as factory/stadium/train station/shopping mall/construction site. The Type A device may be located, tracked or monitored based on the TSCI.

The area/venue may have no local connectivity, e.g., broadband services, WiFi, etc. The Type 1 and/or Type 2 device may be portable. The Type 1 and/or Type 2 device may support plug and play.

Pairwise wireless links may be established between many pairs of devices, forming the tree structure. In each pair (and the associated link), a device (second device) may be a non-leaf (Type B). The other device (first device) may be a leaf (Type A or Type B) or non-leaf (Type B). In the link, the first device functions as a bot (Type 1 device or a Tx device) to send a wireless signal (e.g. probe signal) through the wireless multipath channel to the second device. The second device may function as an Origin (Type 2 device or Rx device) to receive the wireless signal, obtain the TSCI and compute a "linkwise analytics" based on the TSCI.

Because the presence of a human subject will affect the RF signal propagation, e.g., RF signals reflected from the human body will be modulated by the body movement such as the chest movement caused by respiration and heartbeat, vital information of the human subject can be unveiled by analyzing the channel propagation characteristics. Although RF signals can be used to estimate the Respiration Rate (RR) and the Heart Rate (HR), one cannot obtain the Heart Rate Variability (HRV) from RR and HR, without the precise timing of each heartbeat. An accurate HRV estimation is much more difficult than HR estimation. The HR estimating systems usually take multiple samples in the time domain to achieve higher HR estimation accuracy, which equals to averaging the heartbeats over a certain time window. However, they are not applicable for HRV estimation which needs the exact time of each heartbeat and entails the following challenges. First, RF signals reflected by human chests are modulated by both respiration and heartbeats in which the distance change caused by respiration is a magnitude greater than that caused by heartbeats. In signal process terminology, the Signal-to-Interference-plus-Noise Ratio (SINR) is very low to recover and separate the heartbeat wave from the compound signal. Second, the heart pumping motion has to reach the chest wall through bones and tissues first and then be detected by the RF signal. As a result, the bones and tissues of a human body act as a filter and thus dampen the signal. Therefore, the heartbeat wave captured by RF signals lacks sharp peaks as those in ECG signals, making it harder to identify IBIs. Furthermore, to provide a robust system for HRV estimation, it is necessary to determine the number of targets and their locations before estimating HRV for each human subject, which is non-trivial as well.

The present teaching discloses a multi-person HRV estimation system (referred to as "mmHRV" hereinafter) using a Commodity Off-The-Shelf (COTS) millimeter-Wave (mmWave) radio. In some embodiments, a target detector is devised to identify the number of users and their locations without any prior calibration. Due to the fast attenuation of the mmWave RF signal, the strength of the signal decreases as it traverses a longer distance. To detect human subjects at various distances, the mmHRV can employ a two-dimension constant false alarm detector in the range-azimuth plane to estimate the noise level, and thus provide an adaptive threshold for target detection. The phase information is further used to filter out the static objects (e.g., walls, furniture). There may be more than one reflecting point for a single human subject. As a result, to determine the number of targets, mmHRV can further employ a non-parametric clustering to identify the range-azimuth bins corresponding to each human subject.

In some embodiments, after target detection, to estimate the HRV, the heartbeat wave needs to be extracted from the composite received signal whose phase includes the whole chest motion including both the respiration and heartbeat movements. In some embodiments, the respiration movement ranges from 4 to 12 mm with a frequency of 6 to 30 Breaths Per Minute (BPM) while the heartbeat movement ranges from 0.2 to 0.5 mm with a frequency of 50 to 120 BPM, both of which are quasi-periodic signals. Leveraging this property, mmHRV can utilize a heartbeat wave extractor, which optimizes the decomposition of the composite signal to several band-limited signal components. Among the decomposed signal components, the heartbeat wave will be the one whose amplitude and frequency satisfy the requirement of a typical heartbeat signal. Compared with approaches about successively decomposing the composite signal, mmHRV can avoid the error propagation problem by concurrently decomposing the signal components. In addition, the mmHRV system can work in a multi-user case by target detection, to monitor HRV and/or other statistics of heartbeat signals of multiple persons at the same time.

The peaks of the estimated heartbeat wave are then recognized to identify the exact time of each heartbeat.

Consequently, the IBIs can be further derived and used for calculating the commonly used HRV metrics such as the Root Mean Square of Successive Differences (RMSSD), the standard deviation of all the IBIs (SDRR), and the percentage of successive IBIs that differ by more than 50 ms (pNN50).

FIG. 1A illustrates an exemplary setup for a wireless vital monitoring system, e.g. the mmHRV system, according to some embodiments of the present disclosure. As shown in FIG. 1A, the mmHRV system includes a device 100 with a transmitter (Tx) antenna array 101 and a receiver (Rx) antenna array 102. In some embodiments, the device 100 operates at high frequency band, such as 28 GHz, 60 GHz, 77 GHz, with a bandwidth of 3 to 5 GHz. To obtain channel information, the Tx 101 can transmit, using one or more antennas, a wireless signal, which is received by different Rx antennas 102 after reflected by the objects and human beings in a venue shown in FIG. 1A.

As shown in FIG. 1A, there may be multiple objects, including static object 108 and human subjects 105, 106, 107, in the venue where the device 100 is located. The mmHRV system can monitor HRV for multiple persons 105, 106, 107 in the venue at the same time, with or without other static objects 108 in the venue, based on channel information obtained from the reflected signal by the Rx 102. Different objects may be located at different directions from the device 100, without impacting the effective operation of the mmHRV system. For example, human subject 107, human subject 105, and chair 108 are located at different azimuth angles from the device 100. Different objects may also be located at different distances from the device 100, without impacting the effective operation of the mmHRV system. For example, human subject 105 and human subject 106 are located at different distance ranges (but at the same azimuth angle) from the device 100. Different human subjects may face different directions in the venue, without impacting the effective operation of the mmHRV system. For example, human subjects 105, 106, 107 are facing different directions as shown in FIG. 1A.

In some embodiments, the Tx 101 is a Bot as described above; and the Rx 102 is an Origin as described above. While the Tx 101 and the Rx 102 are physically coupled to each other in FIG. 1A, they may be separated in different devices in other embodiments. In some embodiments, the device 100 serves like a radar.

In some embodiments, to evaluate the performance of mmHRV system, 11 participants aging from 20 to 60 are asked to perform extensive experiments under different settings, including different distances, orientation and incidental angles. The Non-Light-of-Sight (NLOS) scenario and multi-person scenario are also investigated. In some embodiments, experimental results show that the mmHRV achieves accurate estimations with a medium error of about 28 ms for IBI estimations (w.r.t. 96.16% accuracy). The Root-Mean-Square-Error (RMSE) of the NLOS and the multi-user case are still within 32 ms and 69 ms respectively. The HRV metrics are also evaluated, which show a better performance compared with the state-of-art works. The mmHRV can achieve 3.89 ms average error of mean IBI, 6.43 ms average error of RMSSD, 6.44 ms average error of SDRR, and 2.52% average error of the pNN50 when users sit 1 meter away from the device.

Figure 1B:
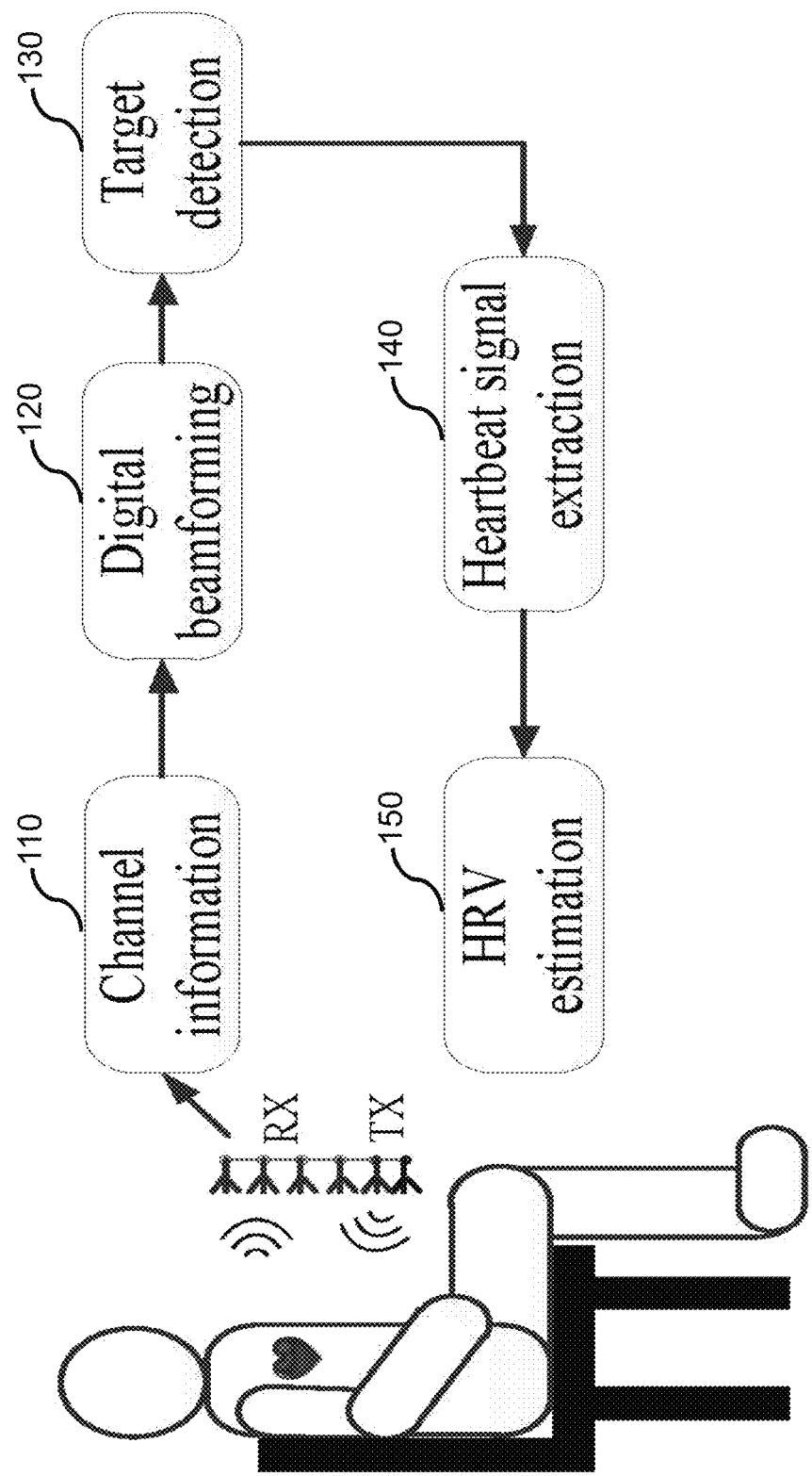
FIG. 1B illustrates an exemplary workflow for wirelessly monitoring heart rate variability, according to some embodiments of the present disclosure.

The mmHRV system is a wireless system that can accurately detect the heartbeat signal of human subjects and estimate their HRV by purely using the RF signals reflected off the users' bodies. FIG. 1B illustrates an exemplary processing workflow of the mmHRV system, according to some embodiments of the present disclosure. In some embodiments, the mmHRV system utilizes a Frequency-Modulated Continuous Wave (FMCW) radar to transmit the RF signal and capture the reflections of human subjects and static objects.

As shown in FIG. 1B, channel information is obtained at operation 110 based on the captured reflections by the Rx. In order to detect human subjects at different locations, a beamforming is performed at operation 120, e.g. by a Bartlett beamformer, to get the channel information at different azimuth-range bins. Then, target detection is performed at operation 130, e.g. by a target detector to adaptively estimate the noise level at various distances and azimuth angles and thus detect the presence of reflecting objects. The variance of phase is further utilized to distinguish human subjects and static objects. To identify the number of target and their locations, a non-parametric clustering algorithm may be employed.

At operation 140, to extract the heartbeat signal from the phase information that is modulated by both respiration and heartbeat, the mmHRV may devise a heartbeat signal extractor, which can decompose the phase signal into several narrow-band signals concurrently and give an estimate of heartbeat wave. The HRV of the detected human subject can be further analyzed at operation 150 based on the Inter-Beat Intervals (IBIs) derived from the estimated heartbeat signals.

Figure 2:
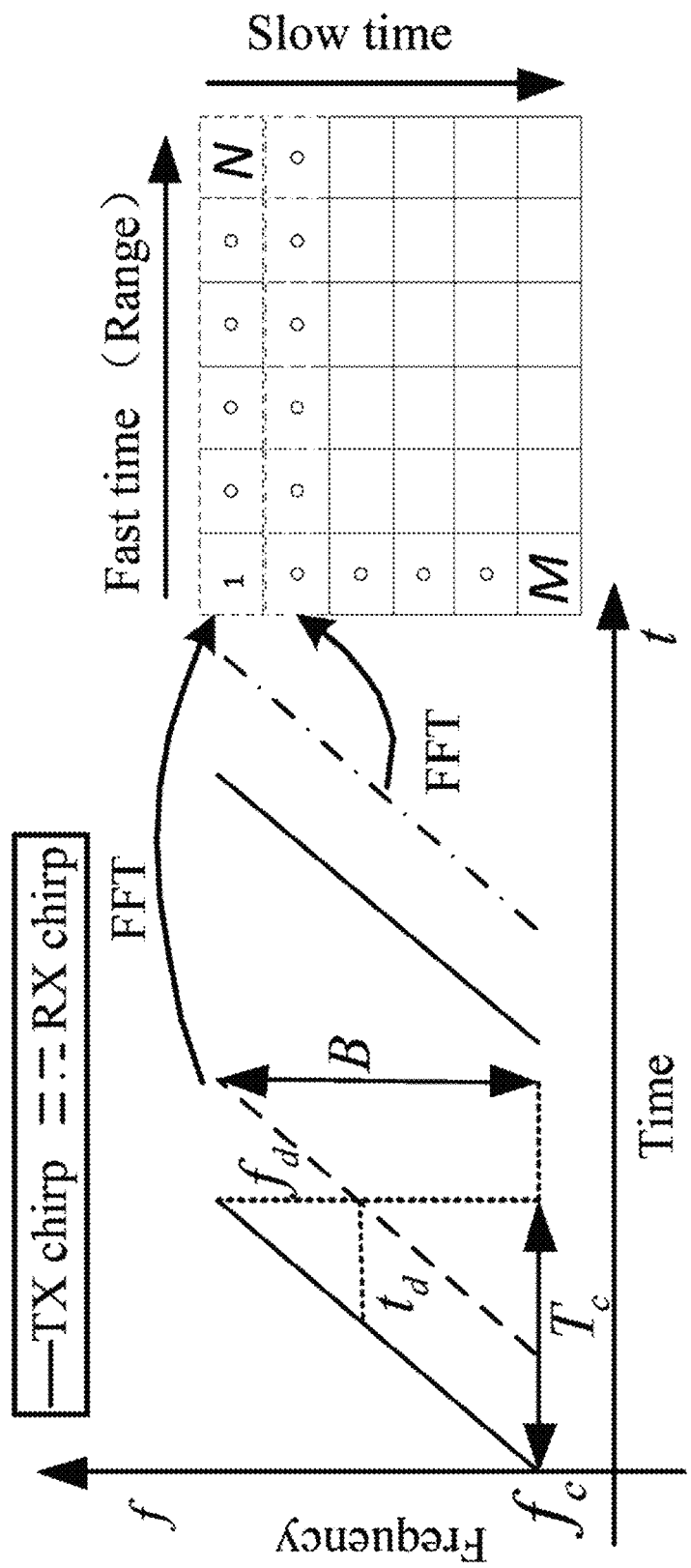
FIG. 2 illustrates exemplary basic concepts of a frequency-modulated continuous wave (FMCW) radar system, according to some embodiments of the present disclosure.

Signal Model: In some embodiments, a chirp signal is transmitted by the FMCW radar, where the instantaneous transmitting frequency is a periodic linearly-increasing signal as shown in FIG. 2, and it can be expressed as $$f_t = f_c + \frac{B}{T_c} t, \tag{1}$$

where $f_c$ is the chirp starting frequency, $T_c$ is the chirp duration and B is the bandwidth. According to Frequency Modulation (FM), the transmitted signal $X_T(t)$ can be expressed as $$x_T(t) = A_T \exp\{-j[2\pi \int_0^t f_t(\tau) d\tau]\} \tag{2}$$
$$= A_T \exp\{-j[2\pi f_c t + \pi \frac{B}{T_c} t^2]\},$$

where $A_T$ is the transmitting power. When the electromagnetic (EM) wave is reflected by human chest at distance d(t), the reflected signal $x_R(t)$ can be expressed as $$x_R(t) = A_R \exp\{-j[2\pi f_c(t - t_d) + \pi \frac{B}{T_c} (t - t_d)^2]\}, \tag{3}$$

where $A_R$ is the amplitude of the receiving signal. $t_d$ stands for the round-trip delay and can be denoted as $$t_d = \frac{2d(t)}{c}, \tag{c}$$

where c is the speed of light.

Mixing the received signal with a replica of the transmitted signal and following a low-pass filter, the channel information h(t) can be expressed as $$h(t) = A\exp\{-j(2\pi\frac{Bt_d}{T_c}t + 2\pi f_c t_d - \pi\frac{B}{T_c}t_d^2)\}. \quad (4)$$

Note that the term $$\pi\frac{B}{T_c}t_d^2$$

is negligible, especially in short-range scenarios. Therefore, the h(t) can be written as $$h(t) = A\exp\{-j(2\pi\frac{Bt_d}{T_c}t + 2\pi f_c t_d)\}, \quad (5)$$

which is a sinusoidal signal whose frequency $$f_b \triangleq \frac{Bt_d}{T_c} = \frac{2Bd(t)}{cT_c}$$

depends on the target's distance. For each chirp, the baseband signal h(t) is digitized by Analog-to-Digital Converter (ADC), producing N samples per chip, referred to as fast time. The time corresponding to the transmission of chirps is referred to as slow time, as shown in FIG. 2. Therefore, the digitized channel information for the $n^{th}$ ADC sample and $m^{th}$ chirp can be expressed as $$h(n, m) = A\exp\{-j(2\pi f_b nT_f + \frac{4\pi d(nT_f + mT_s)}{\lambda_c})\}, \quad (6)$$

where $T_f$ and $T_s$ are the time interval in fast time and slow time respectively. $\lambda c$ denotes the wavelength of the chirp.

Figure 3:
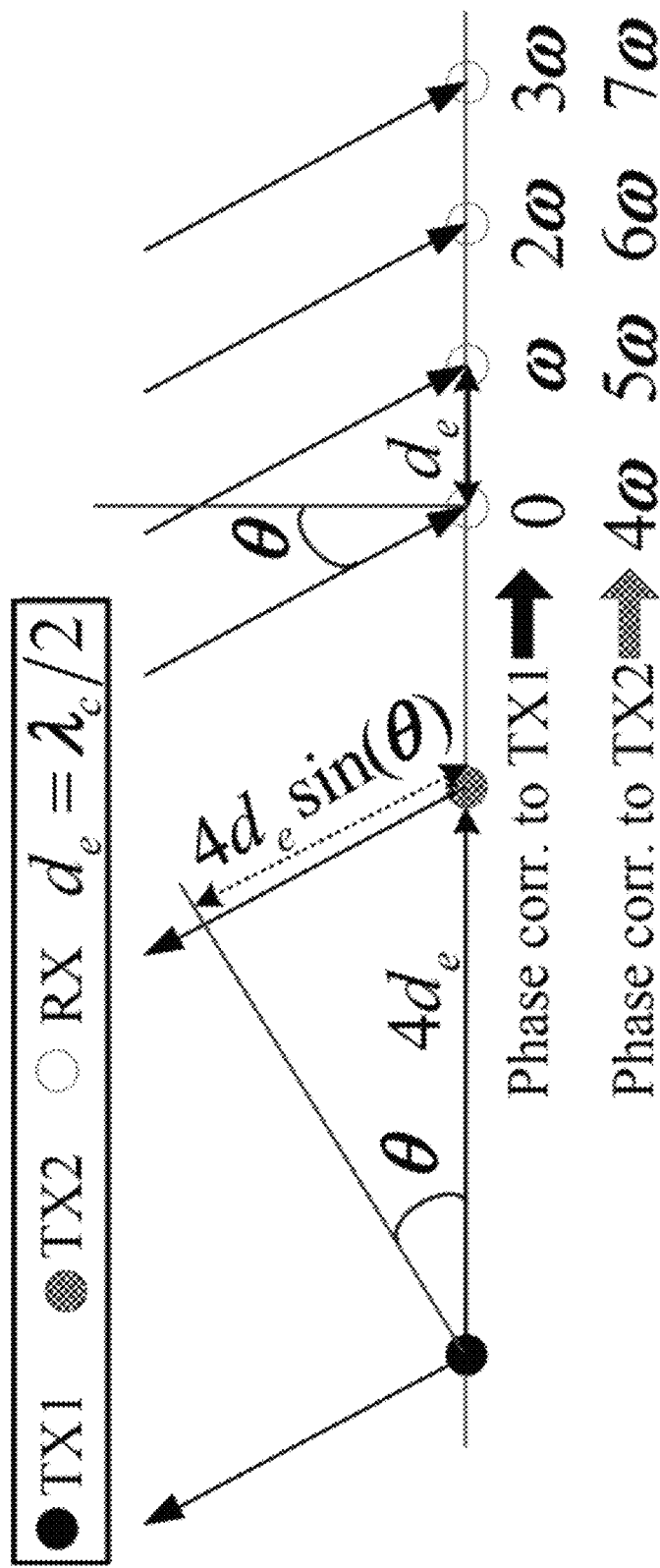
FIG. 3 illustrates exemplary antenna deployment of a wireless vital monitoring system, according to some embodiments of the present disclosure.

In some embodiments of mmHRV, one may take advantage of the multiple antennas of the chipset, and use 2 Tx antennas and 4 Rx antennas, as shown in FIG. 3. To increase the azimuth resolution, the chirps are transmitted in the time-division multiplexing (TDM) mode by transmitting sequentially through two Tx antennas. This is equivalent to the 8-element virtual array as shown in FIG. 3. Therefore, for channel l, the channel information can be rewritten as $$h(l, n, m) = A\exp\{-j(2\pi f_b nT_f + \frac{4\pi d(nT_f + mT_s)}{\lambda_c} + 2\pi\frac{d_l \sin\theta}{\lambda_c})\}, \quad (7)$$

where $d_l$ is the relative distance introduced by virtual antenna l. $\theta$ is the azimuth angle of the target as shown in FIG. 3.

Figure 5A:
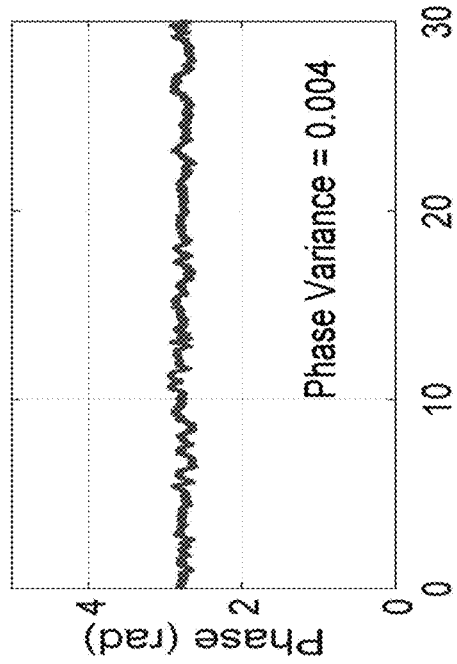
FIGS. 5A-5D illustrate exemplary performances of a human subject detector, according to some embodiments of the present disclosure.

The phase of the channel information changes periodically in slow time due to the periodic motions of respiration and heartbeat. FIG. 5A shows a typical phase signal containing vital signs collected by the system.

For practical application, target detection needs to be performed before vital sign detection. The target detection is hard to achieve, especially in the indoor scenario, where there are various objects (e.g., wall, desk, metal objects, etc.) with strong reflections of EM waves.

Range-FFT and Digital Beamforming: In some embodiments, the channel information for the case when there is a static object is:

$$h(l, n, m) = A\exp\{-j(2\pi f_b nT_f + \frac{4\pi d_0}{\lambda_c} + 2\pi\frac{d_l \sin\theta}{\lambda_c})\}, \quad (8)$$

where $d_0$ is the distance between the object and the device, which stays constant in slow time.

The channel information corresponding to the reflecting object is a periodic signal in fast time, and the periodicity is related to the distance as shown in Eqn. (6) and Eqn. (8). To determine the range information of reflecting objects, Fast Fourier Transform (FFT) may be performed over the fast time for each chirp, i.e., range-FFT, and the channel information can be written as $h_r(l,m)$, where r is the range tap index. The range taps corresponding to the reflecting objects would observe larger energy compared with that without reflecting objects.

To further determine the azimuth angles of the reflecting objects, digital beamforming is performed over all antenna elements for each range tap, and the channel information corresponding to range r and azimuth angle θ can be expressed as $$h_{r,\theta}(m) = s^H(\theta)h_{r,l}(m) + \varepsilon(m), \quad (9)$$

where $s^H(\theta)$ is the steering vector towards angle θ. In some embodiments of mmHRV, a Bartlett beamformer is adopted, where the coefficient of the l-th antenna is $$s_l(\theta) = \exp(-j2\pi\frac{d_l \sin\theta}{\lambda_c}). \quad (10)$$

ε(m) is the additive white Gaussian noise assumed to be independent and identically distributed (I.I.D) for different range-azimuth bins. $h_{r,l}(m) = [h_{r,1}(m), h_{r,2}(m), \ldots, hr_{r,L}(m)]$ is the channel information vector at range tap r overall all antenna elements. Therefore, for each sample m in slow time, one will have a channel information matrix h(r,θ), which contains channel information at different location bins with range r and azimuth angle θ. FIG. 4B shows the amplitude of the channel information at the range-azimuth plane.

Reflecting Object Detector: In some embodiments, to locate human subjects, one first needs to identify the range-angle bins with reflecting objects. The channel information for the bins without any reflecting object only contains noise, and thus, the energy of channel information for the bins with reflecting objects is larger than those without any reflecting objects, as shown in Eqn. (6) and Eqn. (8) respectively. However, it is difficult to find a universal predefined threshold for target detection. According to the propagation laws of EM wave, for the same reflecting objects, a shorter distance corresponding to a larger reflecting energy. In some embodiments of mmHRV, one may utilize the Constant False Alarm Rate (CFAR) detector, which can estimate the noise level by convolving the CFAR window (shown in FIG. 4A) with the channel information at the range-azimuth plane (shown in FIG. 4B), and the location bins with reflecting objects are those whose energy is above the noise level, as shown in FIG. 4C. FIG. 4D shows the example of CFAR detection in the range domain, where the threshold is shown in the dashed line.

Human Subjects Detector: In some embodiments, although reflecting object detector can filter out the empty taps, it cannot distinguish human subjects from static reflecting objects. Different from static objects, the distance between human subjects and the device will change over slow time due to motions (e.g., respiration and heartbeat), and thus result in a phase change as shown in FIG. 5A. Therefore, to further filter out the static reflecting objects, one may leverage the phase information of the candidate bins selected by the reflecting object detector.

Figure 5B:
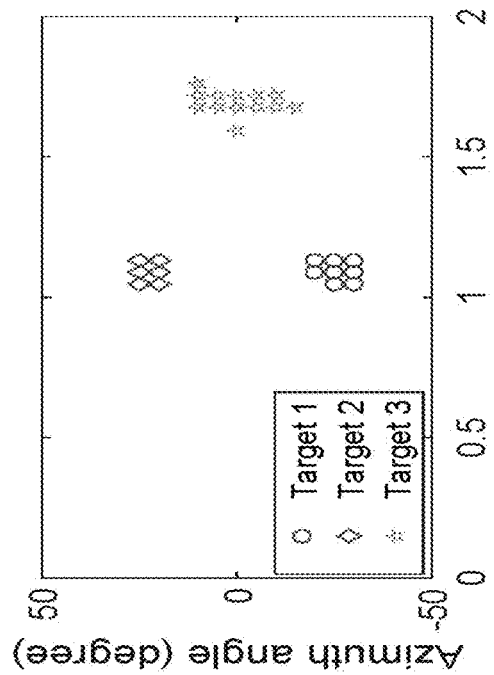
Figure 5C:
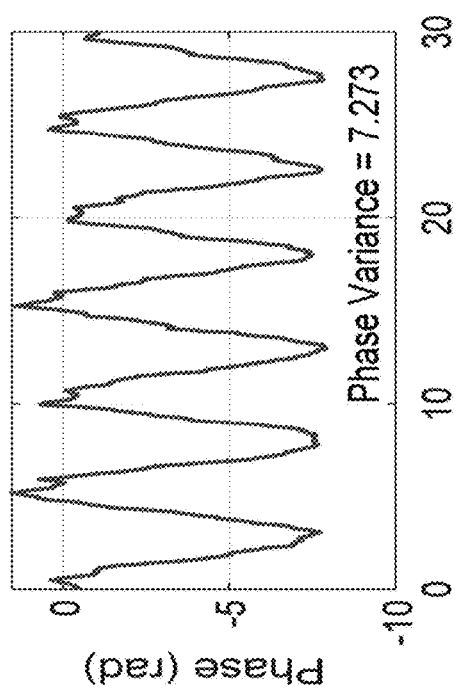
Figure 5D:
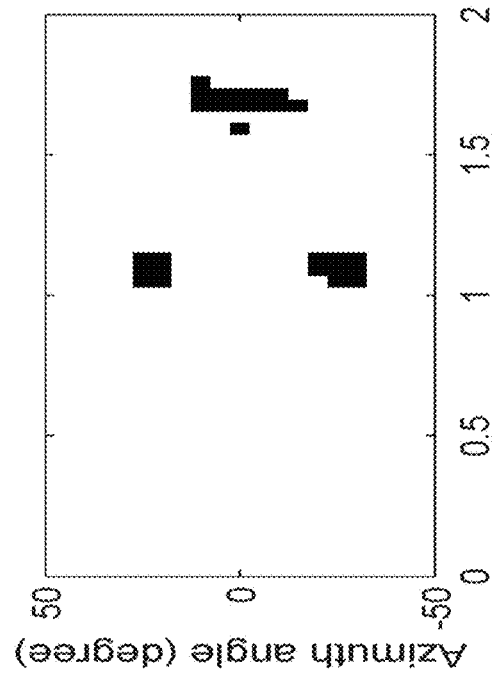

FIGS. 5A-5D illustrate an example of the human subject detector. The ground truth is that there are 3 human subjects, one of which sits at 1.5 m away from the device, with azimuth angle 0°, and the other two sit at 1 m away from the device with azimuth angle 30° and −30° respectively. FIG. 5A is phase information corresponding to a human subject; FIG. 5B is phase information corresponding to a static reflecting object; FIG. 5C is the result of the human subject detector, where the black spots correspond to human subjects; and FIG. 5D shows the clustering result for each target.

When the EM wave is reflected by a human subject, the phase will change over slow time due to the modulation of human motions. Therefore, there is a large phase variance for the bins corresponding to human subjects. However, for bins corresponding to the static objects (e.g. desk, wall, etc.), the phase variance will be much smaller, as shown in FIG. 5A and FIG. 5B. So in some embodiments of mmHRV, to filter out the static objects, one may check the variance of the phase information over slow time, and the bins corresponding to a human subject are those whose phase variance above a certain threshold.

There will be more than one bin corresponding to a human subject considering the volume of a human subject, as shown in FIG. 5C. To identity the target number, the mmHRV utilizes a non-parametric clustering method, Density-Based Spatial Clustering of Applications with Noise (DBSCAN) algorithm, to cluster the candidate bins without prior knowledge of cluster number in some embodiments.

The clustering result is shown in FIG. 5D. The representative of each cluster may be the bin with the best periodicity. For example, the bin with the highest peak for the first peak of the auto-correlation is selected, which corresponds to the bin with the highest SNR of the vital signs.

Heartbeat extraction and HRV estimation: in some embodiments, estimating HRV requires accurate estimation of Inter-Beat Intervals (IBIs). Therefore, the mmHRV may extract the displacement change caused by heartbeats (a.k.a., heartbeat wave) from the compound displacement change of chest wall and detect moments in which heartbeats occur.

Heartbeat Extraction Algorithm: the phase information reflects the distance change caused by vital signs. For simplicity, one can directly use the analog form of signals, and the distance change of the human chest can be written as $$y(t)=s_m(t)+s_r(t)+s_h(t)+n(t), \quad (11)$$

where $s_m(t)$ denotes the distance change caused by body motion. $s_r(t)$ and $s_h(t)$ denote the distance change caused by respiration and heartbeat, respectively. $n(t)$ is the random phase offset introduced by noise, which is independent with the phase change caused by vital signs.

Both $s_r(t)$ and $s_h(t)$ are quasi-periodic signals, where the period can slightly change over time. Besides, one can assume the body motion introduces few oscillations, i.e., a base-band signal. Thus, the signals related with the human subject are sparse in the spectral domain and one can reconstruct these signals with a few band-limited signals. For example, each component $u_k(t)$ is assumed to be compact around a center pulsation $\omega_k$, which is to be determined along with the decomposition. Moreover, the decomposition should achieve the spectrum sparsity and data fidelity at the same time, which is modeled as $$\min_{u_k \in \mathcal{U}, \omega_k \in \Omega} \alpha \sum_{k=1}^{K} \left\| \partial t[(\delta(t) + \frac{j}{\pi t}) * u_k(t)] \exp(-j\omega_k t) \right\|_2^2 + \left\| y(t) - \sum_{k=1}^{K} u_k(t) \right\|_2^2, \quad (12)$$

where the first term evaluates the bandwidth of the analytic signal associated with each component, and the second term evaluates the data fidelity. K is the total number of decomposition components, where $\mathcal{U} = \{u_1(t), \ldots, u_K(t)\}$ and $\Omega = \{\omega_1, \ldots, \omega_K\}$ are the set for all components and their center frequencies, respectively. $\alpha$ is a parameter for balancing the bandwidth constraint and data fidelity.

Once the hyper-parameters are known, the optimization problem in Eqn. (12) can be solved by alternatively or iteratively updating $u_k(t)$ and $\omega_k$ until convergence. To update $u_k$, the subproblem can be written as $$u_k(t) = \underset{u_k(t)}{\operatorname{argmin}} \left\| \partial t[(\delta(t) + \frac{j}{\pi t}) * u_k(t)] \exp(-j\omega_k t) \right\|_2^2 + \left\| y(t) - \sum_{i=1}^{K} u_i(t) \right\|_2^2. \quad (13)$$

By using the Parseval theorem, the problem can be rewritten as $$u_k(\omega) = \underset{u_k(\omega)}{\operatorname{argmin}} \alpha \| j\omega[(1 + \operatorname{sgn}(\omega + \omega_k))u_k(\omega)] \|_2^2 + \left\| y(\omega) - \sum_{i=1}^{K} u_i(\omega) \right\|_2^2, \quad (14)$$

where $u_k(\omega)$ and $y(\omega)$ are the Fourier transfer of $u_k(t)$ and $y(t)$ respectively. After taking integrals over frequency and performing a change of variable, one can get the updating formula, where $$u_k(\omega) = \frac{y(\omega) - \sum_{i, i \neq k} u_i(\omega)}{1 + 2\alpha(\omega - \omega_k)^2}. \quad (15)$$

The center frequencies $\omega_k$ only appear in the bandwidth constraint and thus the subproblem can be written as $$\omega_k = \underset{\omega_k}{\operatorname{argmin}} \left\| \partial t[(\delta(t) + \frac{j}{\pi t}) * u_k(t)] \exp(-j\omega_k t) \right\|_2^2. \quad (16)$$

As before, one can find the optimum in Fourier domain, and have $$\omega_k = \underset{\omega_k}{\operatorname{argmin}} \int_0^\infty (\omega - \omega_k)^2 |u_k(\omega)|^2 d\omega. \quad (17)$$

The minimizer of the above quadratic problem is $$\omega_k = \frac{\int_0^\infty \omega |u_k(\omega)|^2 d\omega}{\int_0^\infty |u_k(\omega)|^2 d\omega}. \tag{18}$$

Figure 6A:
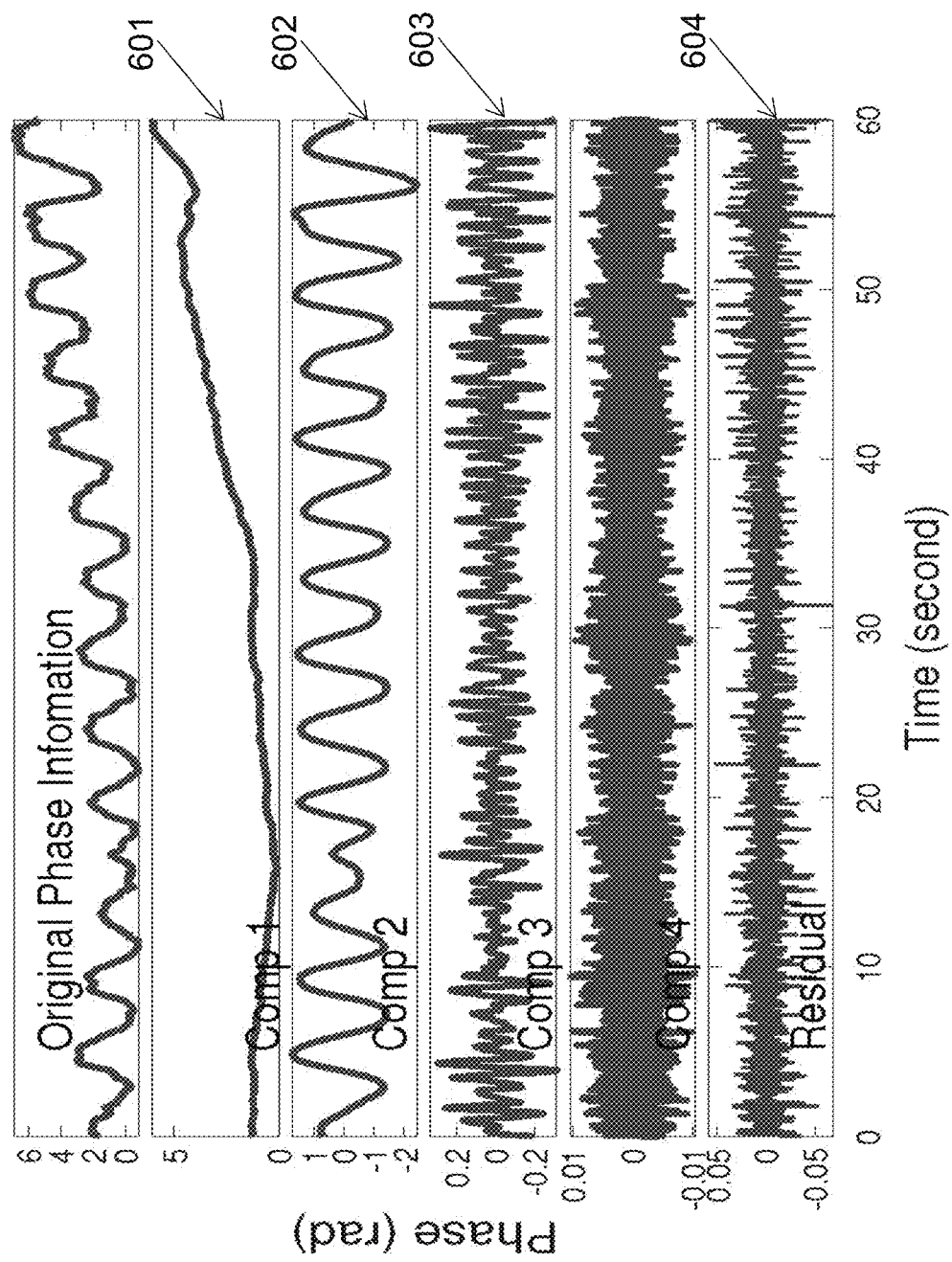
FIGS. 6A-6B illustrate exemplary performances of a heartbeat extractor, according to some embodiments of the present disclosure.
Figure 6B:
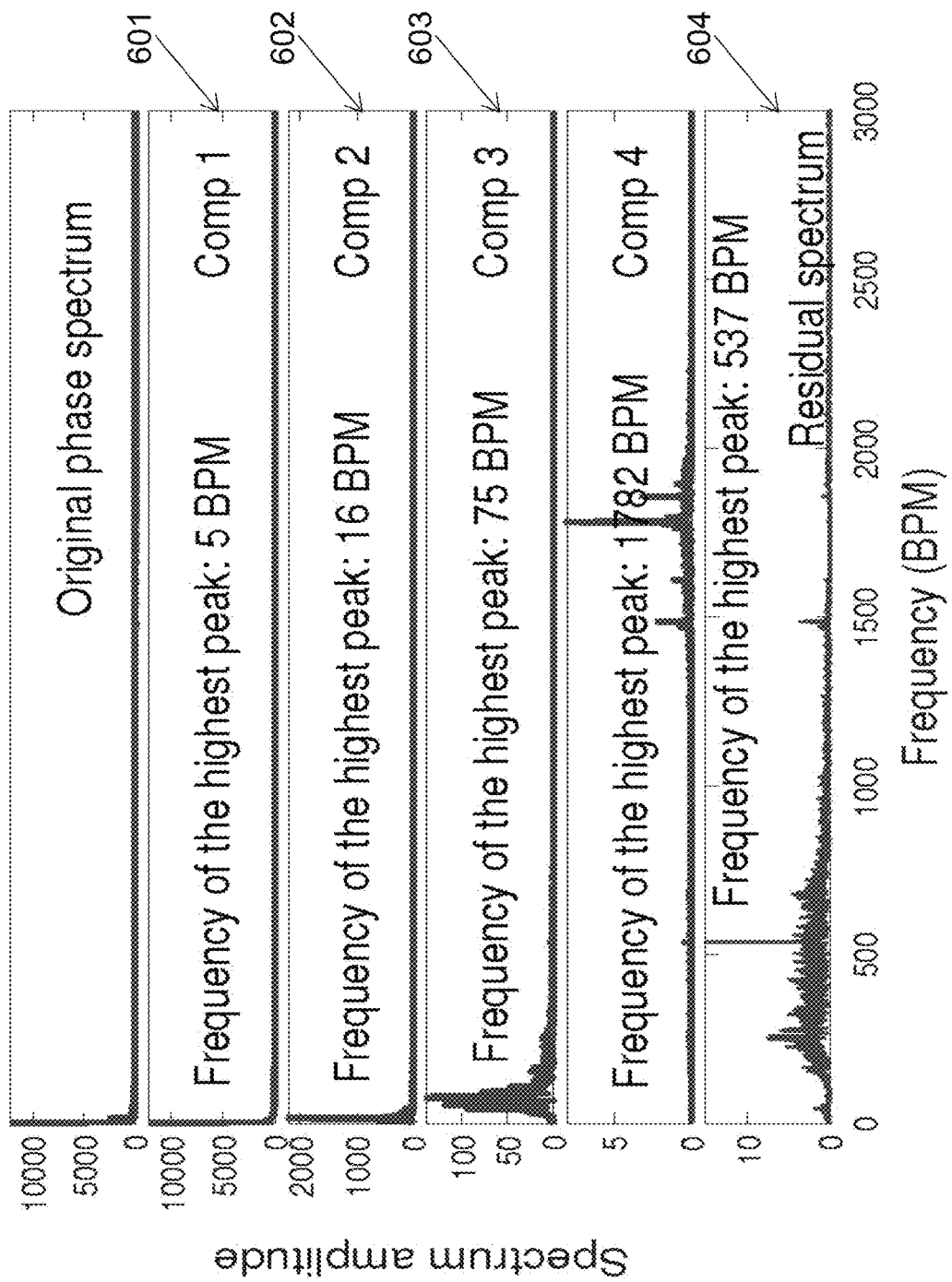

FIGS. 6A-6B illustrate the decomposition of a typical one-minute phase signal from the experiment, where the original phase information has been decomposed into 4 components. FIG. 6A is the decomposition result in the time domain; FIG. 6B is the corresponding spectrum of each component. In some embodiments, the first component 601 reflects the body motion of the human subject; the second component 602 is the respiration motion; and the third component 603 is the heartbeat wave. Since the noise has different vibration characteristics as vital signals, it falls into a different mode as well as in the residual 604 of the decomposition of the signal, as shown in FIGS. 6A-6B.

The decomposition problem can be solved once the hyper-parameters are properly defined. However, it is hard to predefine these hyper-parameters in real applications for heartbeat wave extraction. First, the human motion does not always exist and the human respiration sometimes will have a strong second harmonic component, making it even harder to determine the component number. Furthermore, the hyper-parameter $\alpha$ also influences the decomposition performance. Before discussing how to choose the hyper-parameter, their influence on the decomposition result is disclosed as follows.

For the case that $\alpha$ is too small, i.e., the bandwidth constraint is too loose, when K is too small, the mixing problem will happen so that two signals may merge to a single decomposed component. When K is too large, some of the decomposed components may include noise. For the case that $\alpha$ is too large, i.e., the bandwidth constraint is too tight, when K is too small, some target signals may be discarded in noise. When K is too large, some important parts of the signal may be separated into two or more decomposed components.

In some embodiments of mmHRV, to accurately decompose the signal and get the component of interest, i.e., the heartbeat wave, one may adaptively change the component number K and $\alpha$ for different datasets. Here, a heuristic method is disclosed to change K and a as the iteration proceeds to get proper decomposition result. Since the distance change caused by heartbeat is much smaller than the distance change caused by respiration and human motion, once the component corresponding to the heartbeat is decomposed, the component corresponding to respiration and motion should be decomposed as well, considering the data fidelity constraint in the objective function. Therefore, the algorithm will terminate once one gets the component corresponding to the heartbeat.

HRV Estimation: In some embodiments, once the heartbeat wave is extracted, the exact time corresponding to each heartbeat can be identified by the peaks of the heartbeat wave. To further increase the accuracy, normalization may be performed before peak extraction.

Figure 7A:
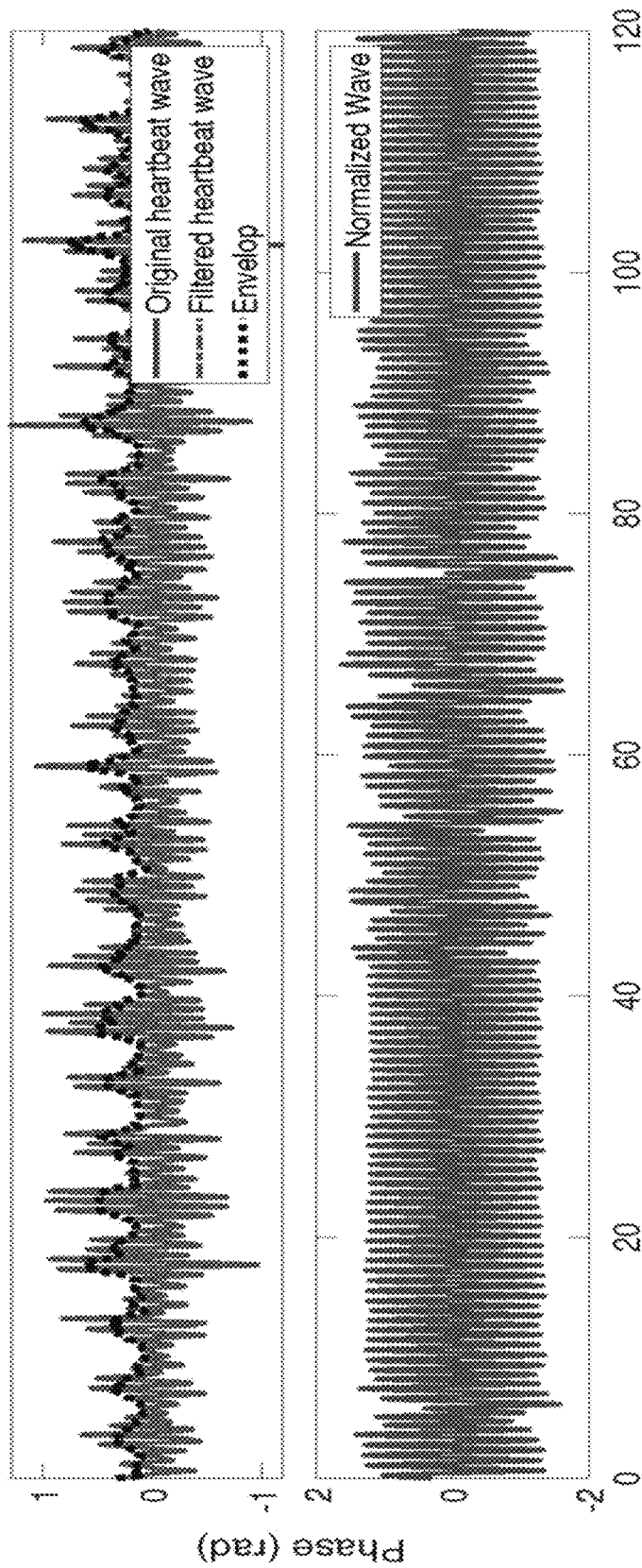
FIGS. 7A-7C illustrate an exemplary inter-beat intervals (IBI) estimation, according to some embodiments of the present disclosure.
Figure 7B:
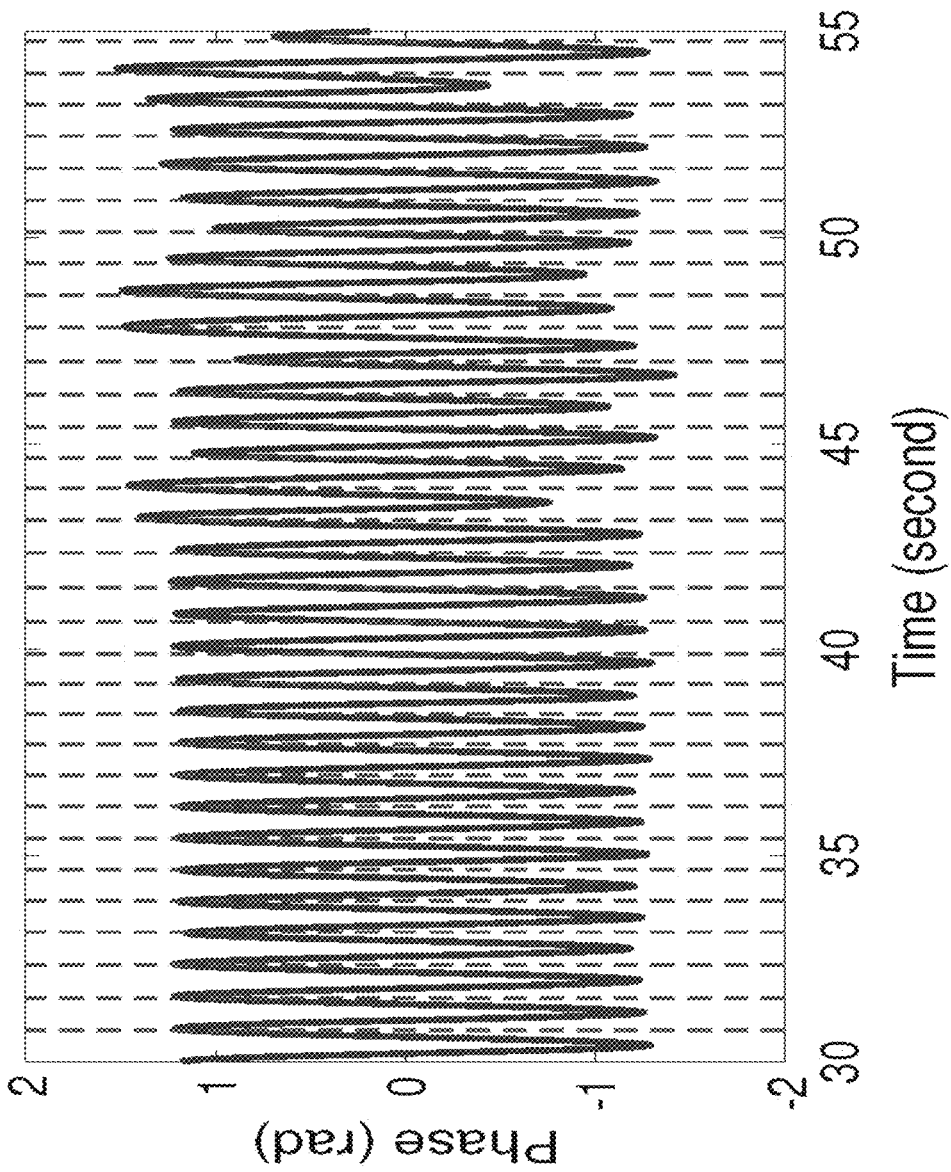
Figure 7C:
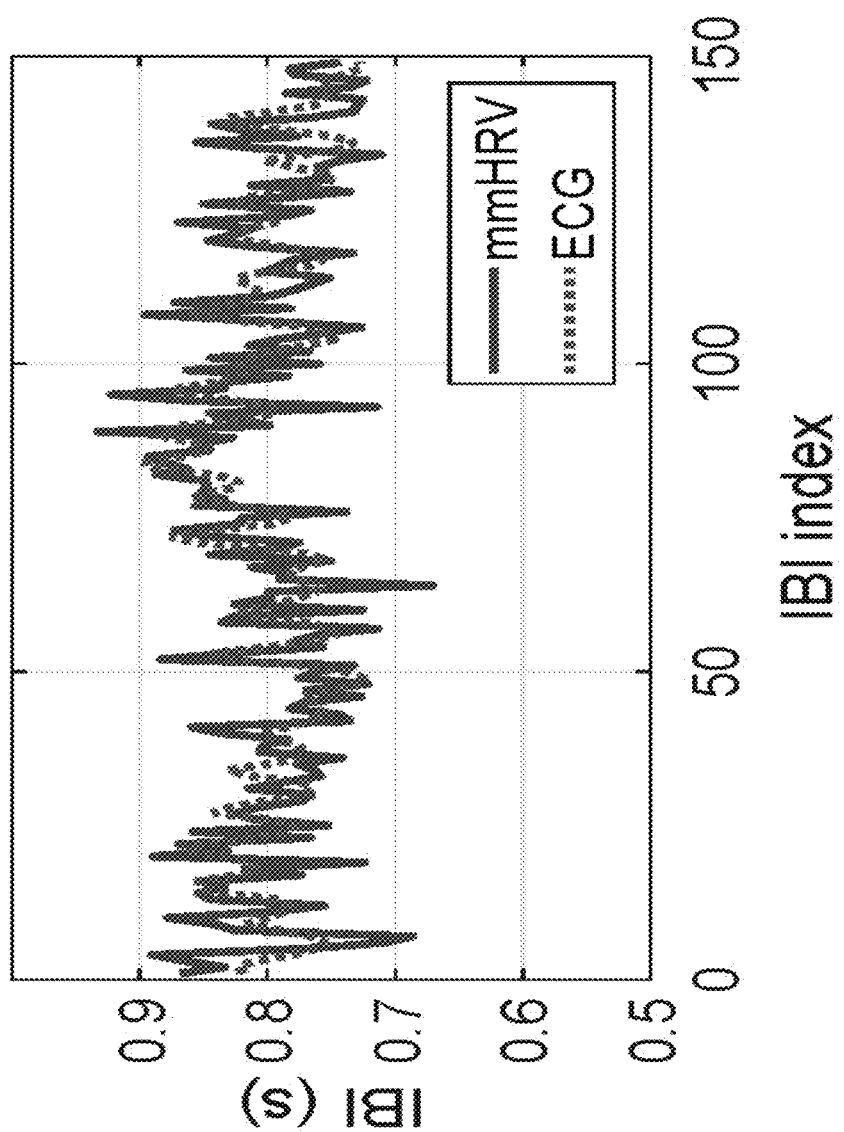

In some embodiments, the envelope of the heartbeat wave is estimated by taking moving average to the absolute value of the heartbeat component, shown as the dashed line in FIG. 7A. One may further perform a moving average filter to the original heartbeat wave to reduce the noise. The normalized wave is the ratio between the filtered heartbeat wave and the estimated envelope. IBIs can thus be derived by calculating the time duration between two adjacent heartbeats. FIG. 7B shows a segment of heartbeat wave and its ECG ground-truth, where the dashed lines show the exact time of each heartbeat from a commercial ECG sensor. The peaks of normalized heartbeat wave match with the ground-truth, where FIG. 7C shows the estimated IBIs and the ECG ground-truth.

The HRV features can be further obtained from the IBI sequence. In some embodiments of mmHRV, one may use the following three metrics to evaluate the HRV. One is the Root Mean Square of Successive Differences (RMSSD), which measures the successive IBI changes, and can be calculated by $$RMSSD = \sqrt{\frac{1}{N_{IBI}-1} \sum_{i=2}^{N_{IBI}} (IBI(i) - IBI(i-1))^2}, \tag{19}$$

where $N_{IBI}$ is the total number of IBIs of the measurement. The standard deviation of all the IBIs (SDRR) measures the variation of the IBIs, which can be calculated as $$SDRR = \sqrt{\frac{1}{N_{IBI}} \sum_{i=1}^{N_{IBI}} (IBI(i) - \overline{IBI})^2}, \tag{20}$$

where $\overline{IBI}$ is the empirical mean of the IBIs of each measurement. The metric pNN50 measures the percentage of successive IBI that differ by more than 50 milliseconds (ms), which can be calculated b $$pNN50 = \frac{\sum_{i=2}^{N_{IBI}} 1\{(IBI(i) - IBI(i-1)) > 50 \text{ ms}\}}{N_{IBI}}, \tag{21}$$

where $1\{\bullet\}$ is the indicator function.

Experiment Evaluation: In some embodiments, one may prototype the mmHRV system by leveraging a commodity mmWave FMCW radar in a typical office of size 3.5 m×3.2 m. By configuring the 2 Tx antennas and 4 Rx antennas into TDM-MIMO mode, the system can achieve a theoretical azimuth resolution of 15°. The Field of View (FoV) is 100° in the horizontal plane with a radius of about 4m, which is sufficient to cover typical rooms. To get the true heartbeat signal, an ECG sensor is used to collect the ground-truth simultaneously with the mmHRV during the experiment. In total, 11 participants (6 males and 5 females) aging from 20 to 60 are invited to conduct experiments in both LOS and NLOS scenario. The experiments are conducted with a variety of settings including different distances, incidental angles, orientations and blockages between the human subject and the radar.

Figure 8B:
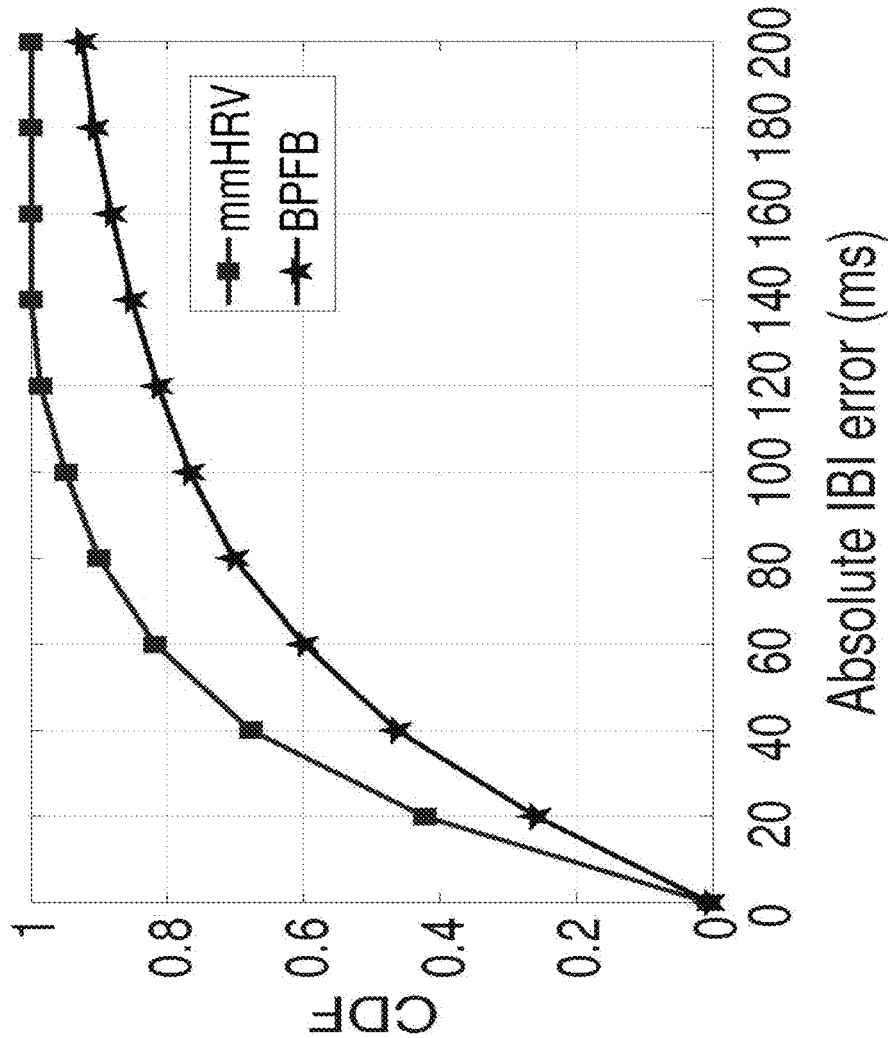
FIGS. 8A-8B illustrate examples of IBI estimation error, according to some embodiments of the present disclosure.
Figure 8A:
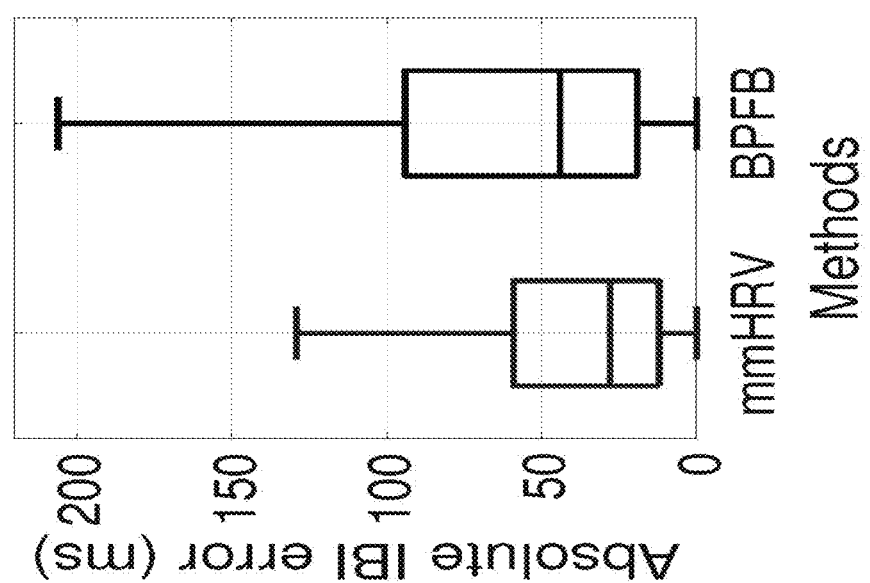

To further evaluate the performance of the disclosed system, the mmHRV system may be compared with the HRV estimation technique using Band-Pass-Filter-Bank (BPFB). FIG. 8 shows the overall IBI estimation accuracy of the mmHRV and BPFB methods. The experiment includes 11 participants while 15 different experiment settings (e.g., different distances, incidental angle, orientation and blockages) are conducted for each participant. As shown in FIG. 8, BPFB yields about 44 ms medium error while the 90-percentile error is about 200 ms. The mmHRV achieves a medium error of about 28 ms, with the 80 ms of the 90-percentile error, which outperforms the BPFB about 60%. To thoroughly evaluate the HRV estimation accuracy, Table I below shows the estimated HRV features in terms of mean IBI, RMSSD, SDRR and pNN50 of 11 participants, where the distance between user and device is about 1 m. It is shown that mmHRV can achieve 3.89 ms average error of mean IBI, 6.43 ms average error of RMSSD, 6.44 ms average error of SDRR and 2.52% average error of the pNN50. Correspondingly, the average estimation error of BPFB is 15.33 ms of mean IBI, 41.94 ms of RMSSD, 32.59 ms of SDRR and 12.17% of the pNN50 estimations.

software. As used herein, "software" means any type of instructions, whether referred to as software, firmware, middleware, microcode, etc. which can configure a machine or device to perform one or more desired functions or processes. Instructions can include code (e.g., in source code format, binary code format, executable code format, or any other suitable format of code). The instructions, when executed by the one or more processors, cause the processing system to perform the various functions described herein.

TABLE I

| Metrics | | Methods | User ID | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| Mean IBI | Value (ms) | ECG | 899 | 790 | 723.2 | 855 | 655 | 823 | 645 | 890 | 564.9 | 728 | 764 |
| | | mmHRV | 906 | 790 | 725.6 | 749 | 652 | 828 | 644 | 888 | 574.2 | 723 | 763 |
| | | BPFB | 882 | 784 | 781.5 | 842 | 677 | 822 | 652 | 878 | 579.1 | 719 | 774 |
| | Error (ms) | mmHRV | 6.95 | 0.45 | 2.47 | 5.92 | 2.17 | 5.4 | 0.99 | 1.97 | 9.33 | 5.38 | 1.2 |
| | | BPFB | 17.9 | 5.7 | 58.36 | 12.4 | 22 | 1.25 | 6.31 | 11.6 | 14.21 | 9.16 | 9.66 |
| RMSSD | Value (ms) | ECG | 38.6 | 10.9 | 37.56 | 31.5 | 34.1 | 35.1 | 16.9 | 27.5 | 5.26 | 23.3 | 31.2 |
| | | mmHRV | 33.5 | 16.5 | 39.08 | 35.3 | 20.3 | 39.7 | 18.1 | 26.1 | 27.8 | 30.5 | 34.9 |
| | | BPFB | 59.3 | 54.3 | 53.83 | 52.9 | 78.6 | 65.63 | 95.09 | 45.56 | 140.36 | 59.61 | 47.92 |
| | Error (ms) | mmHRV | 5.08 | 5.68 | 1.52 | 3.77 | 13.8 | 4.62 | 1.26 | 1.46 | 22.53 | 7.25 | 3.76 |
| | | BPFB | 20.8 | 43.4 | 16.27 | 21.5 | 44.5 | 30.5 | 78.2 | 18 | 135.1 | 36.3 | 16.8 |
| SDRR | Value (ms) | ECG | 56.3 | 22.9 | 50.54 | 35.4 | 33.6 | 48.6 | 23.2 | 32.7 | 12.25 | 35.8 | 50.9 |
| | | mmHRV | 43.2 | 27.3 | 53.3 | 45.9 | 33.5 | 48.5 | 25.5 | 37.4 | 38.66 | 37.2 | 45.5 |
| | | BPFB | 71 | 47.3 | 110.3 | 58.9 | 69.7 | 55.1 | 67.6 | 50.4 | 118.4 | 47.9 | 63.9 |
| | Error (ms) | mmHRV | 13.1 | 4.34 | 2.76 | 10.5 | 0.07 | 0.02 | 2.24 | 4.78 | 26.42 | 1.31 | 5.36 |
| | | BPFB | 14.7 | 24.4 | 59.74 | 23.6 | 36.1 | 6.55 | 44.4 | 17.8 | 106.2 | 12.1 | 13.1 |
| pnn50 | Value (%) | ECG | 11.5 | 0 | 9.15 | 4.32 | 1.14 | 6.29 | 0.55 | 3.76 | 0 | 0.61 | 4.49 |
| | | mmHRV | 8.46 | 1.33 | 7.93 | 5.76 | 2.2 | 6.99 | 2.17 | 2.26 | 4.83 | 6.71 | 6.41 |
| | | BPFB | 19.4 | 18.5 | 14.57 | 20 | 14.2 | 22.9 | 18.1 | 12.6 | 10.24 | 12.8 | 12.4 |
| | Error (ms) | mmHRV | 3.08 | 1.33 | 1.22 | 1.44 | 1.05 | 0.7 | 1.62 | 1.5 | 4.83 | 6.09 | 1.92 |
| | | BPFB | 7.86 | 18.5 | 5.42 | 15.7 | 13.1 | 16.6 | 17.6 | 8.83 | 10.24 | 12.2 | 7.93 |

Figure 9:
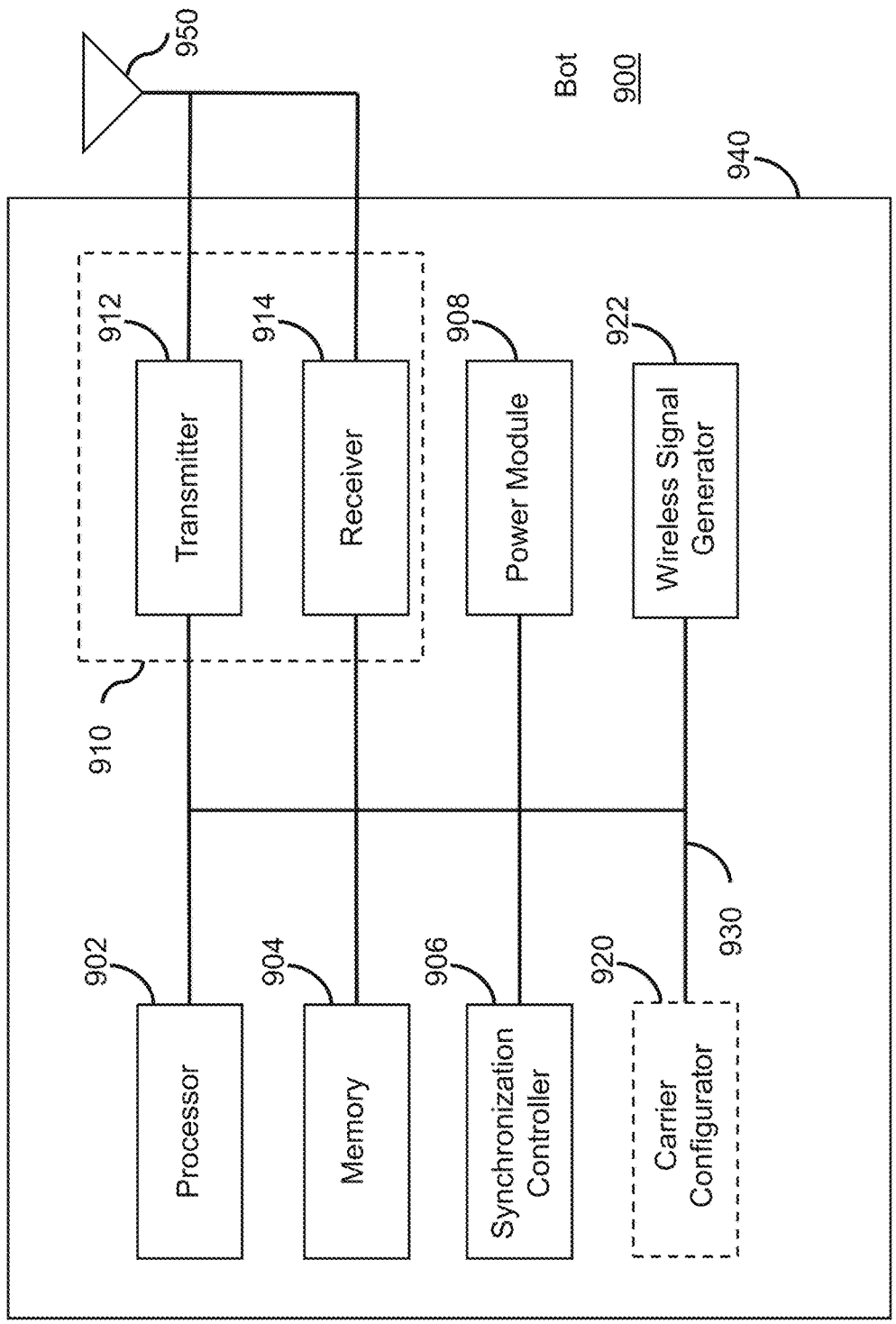
FIG. 9 illustrates an exemplary block diagram of a first wireless device of a wireless vital monitoring system, according to some embodiments of the present disclosure.

FIG. 9 illustrates an exemplary block diagram of a first wireless device, e.g. a Bot 900, of a wireless vital monitoring system, according to one embodiment of the present teaching. The Bot 900 is an example of a device that can be configured to implement the various methods described herein. As shown in FIG. 9, the Bot 900 includes a housing 940 containing a processor 902, a memory 904, a transceiver 910 comprising a transmitter 912 and receiver 914, a synchronization controller 906, a power module 908, an optional carrier configurator 920 and a wireless signal generator 922.

In this embodiment, the processor 902 controls the general operation of the Bot 900 and can include one or more processing circuits or modules such as a central processing unit (CPU) and/or any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable circuits, devices and/or structures that can perform calculations or other manipulations of data.

The memory 904, which can include both read-only memory (ROM) and random access memory (RAM), can provide instructions and data to the processor 902. A portion of the memory 904 can also include non-volatile random access memory (NVRAM). The processor 902 typically performs logical and arithmetic operations based on program instructions stored within the memory 904. The instructions (a.k.a., software) stored in the memory 904 can be executed by the processor 902 to perform the methods described herein. The processor 902 and the memory 904 together form a processing system that stores and executes The transceiver 910, which includes the transmitter 912 and receiver 914, allows the Bot 900 to transmit and receive data to and from a remote device (e.g., an Origin or another Bot). An antenna 950 is typically attached to the housing 940 and electrically coupled to the transceiver 910. In various embodiments, the Bot 900 includes (not shown) multiple transmitters, multiple receivers, and multiple transceivers. In one embodiment, the antenna 950 is replaced with a multi-antenna array 950 that can form a plurality of beams each of which points in a distinct direction. The transmitter 912 can be configured to wirelessly transmit signals having different types or functions, such signals being generated by the processor 902. Similarly, the receiver 914 is configured to receive wireless signals having different types or functions, and the processor 902 is configured to process signals of a plurality of different types.

The Bot 900 in this example may serve as Bot 101 in FIG. 1A for wireless vital monitoring in a venue. For example, the wireless signal generator 922 may generate and transmit, via the transmitter 912, a wireless signal through a wireless channel in the venue. The wireless signal carries information of the channel. Because the wireless signal is reflected by human being(s) having heartbeat motions in the venue, the channel information includes information, e.g. heart rate variability information, of the heartbeat motions. As such, the heart rate variability of the human being(s) in the venue can be monitored based on the wireless signal. The generation of the wireless signal at the wireless signal generator 922 may be based on a request for wireless vital monitoring from another device, e.g. an Origin, or based on a system pre-configuration. That is, the Bot 900 may or may not know that the wireless signal transmitted will be used for wireless vital monitoring.

The synchronization controller 906 in this example may be configured to control the operations of the Bot 900 to be synchronized or un-synchronized with another device, e.g. an Origin or another Bot. In one embodiment, the synchronization controller 906 may control the Bot 900 to be synchronized with an Origin that receives the wireless signal transmitted by the Bot 900. In another embodiment, the synchronization controller 906 may control the Bot 900 to transmit the wireless signal asynchronously with other Bots. In another embodiment, each of the Bot 900 and other Bots may transmit the wireless signals individually and asynchronously.

The carrier configurator 920 is an optional component in Bot 900 to configure transmission resources, e.g. time and carrier, for transmitting the wireless signal generated by the wireless signal generator 922. In one embodiment, each CI of the time series of CI has one or more components each corresponding to a carrier or sub-carrier of the transmission of the wireless signal. The wireless vital monitoring may be based on any one or any combination of the components.

The power module 908 can include a power source such as one or more batteries, and a power regulator, to provide regulated power to each of the above-described modules in FIG. 9. In some embodiments, if the Bot 900 is coupled to a dedicated external power source (e.g., a wall electrical outlet), the power module 908 can include a transformer and a power regulator.

The various modules discussed above are coupled together by a bus system 930. The bus system 930 can include a data bus and, for example, a power bus, a control signal bus, and/or a status signal bus in addition to the data bus. It is understood that the modules of the Bot 900 can be operatively coupled to one another using any suitable techniques and mediums.

Although a number of separate modules or components are illustrated in FIG. 9, persons of ordinary skill in the art will understand that one or more of the modules can be combined or commonly implemented. For example, the processor 902 can implement not only the functionality described above with respect to the processor 902, but also implement the functionality described above with respect to the wireless signal generator 922. Conversely, each of the modules illustrated in FIG. 9 can be implemented using a plurality of separate components or elements.

Figure 10:
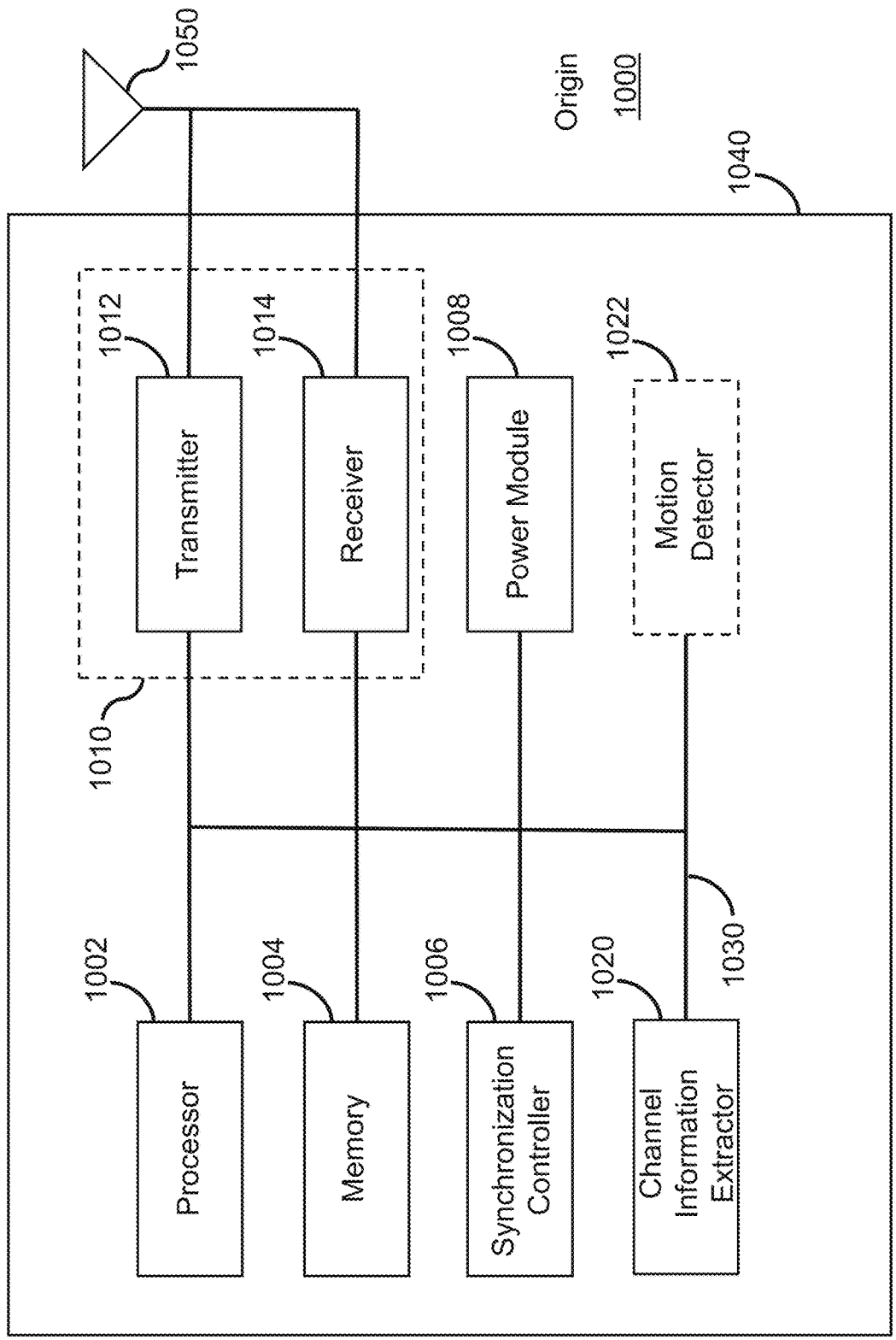
FIG. 10 illustrates an exemplary block diagram of a second wireless device of a wireless vital monitoring system, according to some embodiments of the present disclosure.

FIG. 10 illustrates an exemplary block diagram of a second wireless device, e.g. an Origin 1000, of a wireless vital monitoring system, according to one embodiment of the present teaching. The Origin 1000 is an example of a device that can be configured to implement the various methods described herein. The Origin 1000 in this example may serve as Origin 102 in FIG. 1A for wireless vital monitoring in a venue. As shown in FIG. 10, the Origin 1000 includes a housing 1040 containing a processor 1002, a memory 1004, a transceiver 1010 comprising a transmitter 1012 and a receiver 1014, a power module 1008, a synchronization controller 1006, a channel information extractor 1020, and an optional motion detector 1022.

In this embodiment, the processor 1002, the memory 1004, the transceiver 1010 and the power module 1008 work similarly to the processor 902, the memory 904, the transceiver 910 and the power module 908 in the Bot 900. An antenna 1050 or a multi-antenna array 1050 is typically attached to the housing 1040 and electrically coupled to the transceiver 1010.

The Origin 1000 may be a second wireless device that has a different type from that of the first wireless device (e.g. the Bot 900). In particular, the channel information extractor 1020 in the Origin 1000 is configured for receiving the wireless signal through the wireless channel, and obtaining a time series of channel information (CI) of the wireless channel based on the wireless signal. The channel information extractor 1020 may send the extracted CI to the optional motion detector 1022 or to a motion detector outside the Origin 1000 for wireless vital monitoring in the venue.

The motion detector 1022 is an optional component in the Origin 1000. In one embodiment, it is within the Origin 1000 as shown in FIG. 10. In another embodiment, it is outside the Origin 1000 and in another device, which may be a Bot, another Origin, a cloud server, a fog server, a local server, and an edge server. The optional motion detector 1022 may be configured for detecting heartbeats and monitoring heart rate variability in the venue based on heartbeat motion information of the persons in the venue. The motion information is computed based on the time series of CI by the motion detector 1022 or another motion detector outside the Origin 1000.

The synchronization controller 1006 in this example may be configured to control the operations of the Origin 1000 to be synchronized or un-synchronized with another device, e.g. a Bot, another Origin, or an independent motion detector. In one embodiment, the synchronization controller 1006 may control the Origin 1000 to be synchronized with a Bot that transmits a wireless signal. In another embodiment, the synchronization controller 1006 may control the Origin 1000 to receive the wireless signal asynchronously with other Origins. In another embodiment, each of the Origin 1000 and other Origins may receive the wireless signals individually and asynchronously. In one embodiment, the optional motion detector 1022 or a motion detector outside the Origin 1000 is configured for asynchronously computing respective heterogeneous motion information based on the respective time series of CI.

The various modules discussed above are coupled together by a bus system 1030. The bus system 1030 can include a data bus and, for example, a power bus, a control signal bus, and/or a status signal bus in addition to the data bus. It is understood that the modules of the Origin 1000 can be operatively coupled to one another using any suitable techniques and mediums.

Although a number of separate modules or components are illustrated in FIG. 10, persons of ordinary skill in the art will understand that one or more of the modules can be combined or commonly implemented. For example, the processor 1002 can implement not only the functionality described above with respect to the processor 1002, but also implement the functionality described above with respect to the channel information extractor 1020. Conversely, each of the modules illustrated in FIG. 10 can be implemented using a plurality of separate components or elements.

Figure 11:
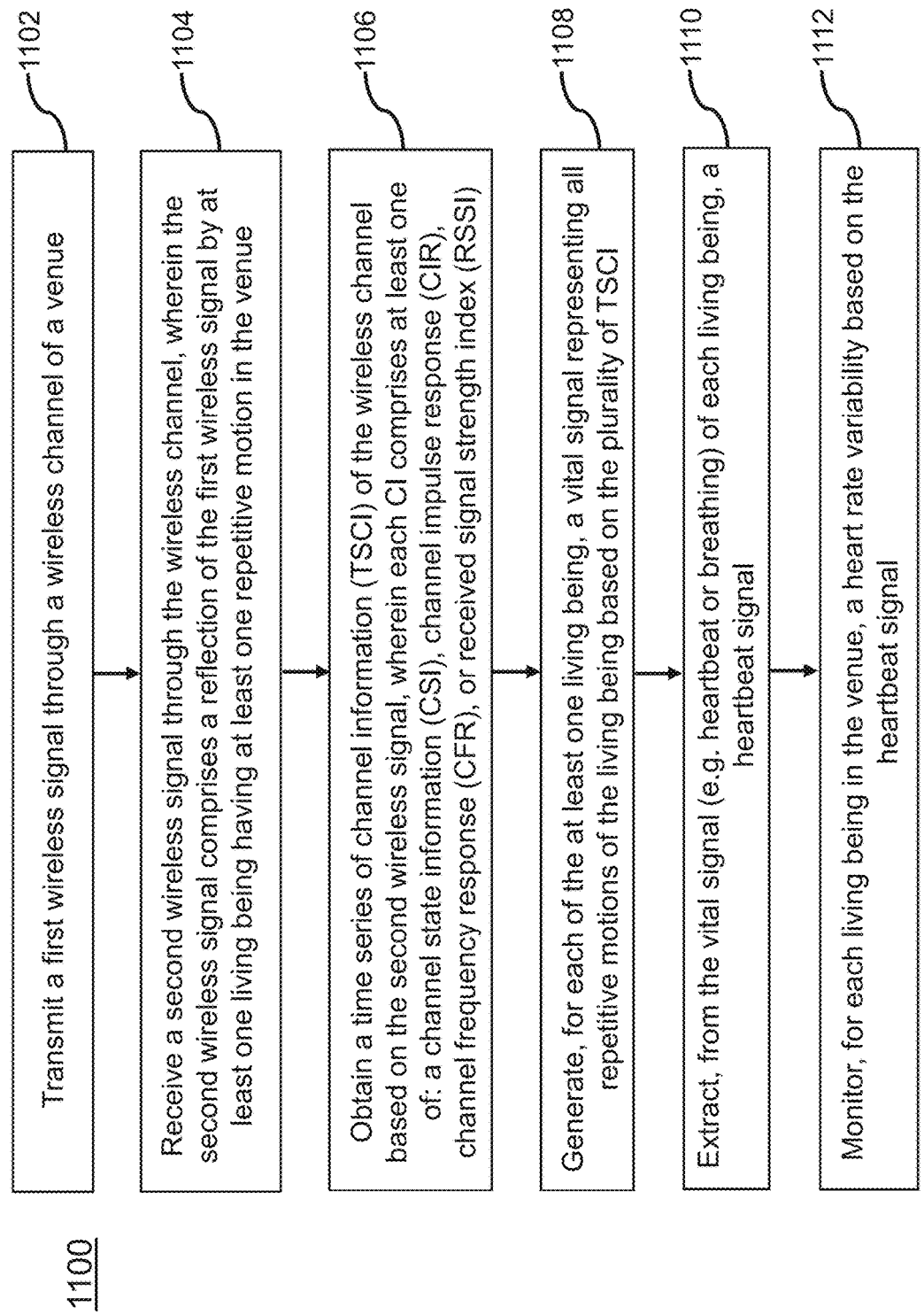
FIG. 11 illustrates a flow chart of an exemplary method for wireless vital monitoring, according to some embodiments of the present disclosure.

FIG. 11 illustrates a flow chart of an exemplary method 1100 for wireless vital monitoring, according to some embodiments of the present disclosure. At operation 1102, a first wireless signal is transmitted through a wireless channel of a venue. At operation 1104, a second wireless signal is received through the wireless channel, wherein the second wireless signal comprises a reflection of the first wireless signal by at least one living being having at least one repetitive motion in the venue. At operation 1106, a time series of channel information (CI) of the wireless channel is obtained based on the second wireless signal, wherein each CI comprises at least one of: a channel state information (CSI), channel impulse response (CIR), channel frequency response (CFR), or received signal strength index (RSSI). At operation 1108, for each of the at least one living being, a vital signal representing all repetitive motions of the living being is generated based on the plurality of TSCI. The vital signal may represent vital signs like heartbeat or breathing. At operation 1110, a heartbeat signal is extracted from the vital signal of each living being. At operation 1112, for each living being in the venue, a heart rate variability is monitored based on the heartbeat signal. The order of the operations in FIG. 11 may be changed according to various embodiments of the present teaching.

In some embodiments, a wireless vital monitoring method includes steps s1 to s8 as described below.

At step s1: capture CSI using multiple transmit (Tx) antenna and multiple receive (Rx) antenna.

At step s2: apply beamforming to get directional CSI (e.g. CIR). This may associate direction and distance with CSI. At step s3: determine direction-of-interest (DoI) by detecting object presence in each direction, which includes steps s3a and s3b performed for each direction.

At step s3a: compute magnitude of CSI (e.g. |h(theta, distance)| of CIR) for each time instance, then time-average it over a time window. At step s3b: determine object is present in the direction (and thus the direction is DoI) if the time-averaged magnitude response is greater than a threshold T1, wherein the threshold T1 may be a 2-dimensional CFAR filtering of |h| in theta and distance direction.

At step s4: for each DoI (i.e. the direction where object presence is detected), perform motion detection by classifying object into: (a) static object (e.g. furniture), (b) stationary human (with breathing and heartbeat), and (c) random body motion, which includes steps s4a to s4e.

At step s4a: compute variance (V) of phase of CSI (e.g. phase of h(theta, distance)), over time in a time window. In some embodiments, a larger phase variance means the target is a living being with heartbeat. At step s4b: classify motion as "static object" if V is less than a threshold T2. At step s4c: if V>T2, compute auto-correlation function (ACF) and find a significant feature point (e.g. first peak) P1. At step s4d: classify motion as "stationary human" if V>T2 and P1>T3. At step s4e: classify motion as "random body motion" if V>T2 and P1<T3. In some embodiments, a larger P1 means a more periodic feature.

At step s5: determine the number of stationary human subjects and their corresponding vital motions, which includes steps s5a to s5b.

At step s5a: cluster the set of point-of-interest (PoI) (i.e., the (theta, distance) corresponding to stationary human in step s4), wherein the PoIs are clustered without prior knowledge of the cluster number, i.e., non-parametric clustering. The PoIs can be classified based on density-based method (e.g., DBSCAN) or can be classified based on distance (e.g., if the distance between two PoIs>common size of a human body, then they belong to different clusters).

At step s5b: generate the vital motions corresponding to each human subject. When more than one PoI corresponds to a human subject, the corresponding motion can be combined, e.g., by weighted averaging the phase measurement of PoIs, or a dominant PoI may be identified and the vital motion is associated with the dominant tap.

At step s6: for each human subject, extract a heartbeat signal by decomposing the vital signal with a few band-limited signals by either jointly optimizing the decomposition as in step s6a or a successive decomposition as in step s6b.

At step s6a: jointly optimize the decomposition of the raw signal modeled using steps s6a1, s6a2 and s6a3.

At step s6a1: given a default setting of component number K and the parameter α for balancing the bandwidth constraint and data fidelity, alternatively optimize the components and their center frequencies.

At step s6a2: check whether there is a component corresponding to heartbeat by some features, wherein the component corresponds to heartbeat wave if the amplitude of the signal is located in range [T4, T5], and its center frequency is located in range [T6, T7]. In some embodiments, one may also extract breathing/respiration signals at step s6a2.

At step s6a3: if there is a decomposed component corresponding to heartbeat, normalize the heartbeat signal in step s7; otherwise, update the values of component number K and tradeoff factor α and repeat steps s6a1 to s6a3.

At step s6b: successively decompose the raw signal to get the heartbeat wave using steps s6b1, s6b2, and s6b3.

At step s6b1: process the raw signal by removing/suppressing influence of the dominant (larger magnitude) periodic signal (e.g. filter the raw signal, or estimate the dominant periodic signal and subtract it from the raw signal), wherein the dominant periodic signal may be estimated by an operation on the raw signal (e.g. smoothing, low pass filtering, spline interpolation, B-spline, cubic spline interpolation, polynomial fitting, polynomial fitting with order adaptively selected based on the distance/tap, etc.).

At step s6b2: compute characteristics of the next dominant periodic signal based on the processed raw signal. The characteristics may be computed based on frequency transform, trigonometric transform, fast Fourier transform (FFT), wavelet transform, ACF, etc. The characteristics may also be computed by constrained optimization (e.g. minimization of an energy function subjected to a smoothness constraint). The energy function may be energy of frequency (e.g. energy of FFT of dominant-component-removed signal, where the signal may be the fused/clustered signal).

At step s6b3: check whether the component corresponds to heartbeat by some features, wherein the component corresponds to heartbeat wave if the amplitude of the signal is located in range [T4, T5], and its center frequency is located in range [T6, T7]. If it corresponds to the heartbeat, normalize the heartbeat signal in step s7; otherwise, remove the component and then repeat steps s6b2 and s6b3.

In some embodiments, other mode decomposition method can be applied for step s6, where mode can be viewed as a frequency component, a signal, etc. by e.g. ensemble empirical mode decomposition. In some embodiments, instead of using phase information as the input to extract heartbeat, one may also rely on CIR amplitude to extract heartbeat signal/wave.

At step s7: normalize the estimated heartbeat wave by dividing the estimated wave with an envelope of the signal, wherein the envelope can be estimated by an operation on the raw signal (e.g. smoothing, low pass filtering, spline interpolation, B-spline, cubic spline interpolation, polynomial fitting and moving average).

At step s8: identify an exact time of each heartbeat and then calculate the inter-beat intervals to estimate heart rate variability (HRV) and/or other statistics of inter-beat intervals, wherein the exact time of each heartbeat can be identified by several ways, e.g., by identifying the peaks of the heartbeat waves, identifying the zero-crossing points, or finding some feature points after taking continuous wavelet transform.

The following numbered clauses provide implementation examples for wireless vital monitoring.

Clause 1. A system for wireless monitoring, comprising: a transmitter configured for transmitting, using N1 transmit antennas, a first wireless signal through a wireless channel of a venue; a receiver configured for receiving, using N2 receive antennas, a second wireless signal through the wireless channel, wherein N1 and N2 are positive integers, wherein the second wireless signal comprises a reflection of the first wireless signal by at least one living being having at least one repetitive motion in the venue; and a processor configured for: obtaining a plurality of time series of channel information (TSCI) of the wireless channel based on the second wireless signal, wherein each of the plurality of TSCI is associated with a respective transmit antenna of the transmitter and a respective receive antenna of the receiver, generating, for each living being of the at least one living being, a vital signal representing all repetitive motions of the living being based on the plurality of TSCI, extracting, from the vital signal of each living being, a heartbeat signal, and monitoring, for each living being in the venue, a heart rate variability based on the heartbeat signal.

Clause 2. The system of clause 1, wherein: the at least one living being comprises: a human being or an animal; the first wireless signal is carried on a millimeter wave; each object in the venue has a location determined based on a plurality of spatial bins in the venue; each of the plurality of spatial bins is determined by: a direction and a distance range originating from the receiver; and each direction is associated with at least one of: an angle, an azimuth angle, or an elevation angle.

Clause 3. The system of clause 2, wherein generating the vital signal for each living being comprises: computing a beamforming based on the plurality of TSCI; and computing a set of time series of directional channel information (CI) each associated with a direction based on the beamforming.

Clause 4. The system of clause 3, wherein generating the vital signal for each living being further comprises: for each directional CI associated with a respective direction, computing, for each time instance, a CI amplitude based on the directional CI for the respective direction and a distance range to obtain CI amplitudes over time, computing a time average of the CI amplitudes based on a time window, and detecting object presence at the distance range in the respective direction when the time average is greater than a first threshold; and determining a set of direction-of-interest's (DoIs) each comprising a direction in which object presence is detected.

Clause 5. The system of clause 4, wherein the first threshold is determined adaptively to filter the CI amplitudes at the distance range in the respective direction based on a two-dimensional constant false alarm rate (CFAR).

Clause 6. The system of clause 4, wherein generating the vital signal for each living being further comprises: for each DoI in the set of DoIs and for each distance range, computing a phase variance of a directional CI associated with the DoI over time in a time window, classifying a detected object at the distance range and the DoI as a static object without repetitive motion, when the phase variance is less than a second threshold, and classifying a detected object at the distance range and the DoI as a living being with repetitive motion, when the phase variance is greater than or equal to the second threshold.

Clause 7. The system of clause 6, wherein generating the vital signal for each living being further comprises: determining a plurality of target spatial bins for each detected living being, wherein each of the plurality of target spatial bins is determined by a target DoI and a target distance range; and for each target spatial bin, computing an auto-correlation function based on the directional CI associated with the target spatial bin, determining a first peak of the auto-correlation function, classifying a motion of the detected living being at the target spatial bin as a repetitive motion when the first peak is greater than a third threshold, and classifying a motion of the detected living being at the target spatial bin as a random body motion when the first peak is less than or equal to the third threshold.

Clause 8. The system of clause 7, wherein generating the vital signal for each living being further comprises: computing a set of point-of-interest's (PoIs), wherein each PoI in the set of PoIs is associated with a detected living being at the PoI and is a target spatial bin in the venue associated with a repetitive motion of the detected living being at the PoI; clustering the set of PoIs to generate at least one PoI cluster with a total cluster number, wherein: the set of PoIs are clustered without prior knowledge of the total cluster number after clustering, and the set of PoIs are clustered based on at least one of: a density related to the set of PoIs, a distance between any two PoIs of the set of PoIs, or a threshold related to a size of a living being; and determining a quantity of target living beings in the venue based on the total cluster number.

Clause 9. The system of clause 8, wherein generating the vital signal for each living being further comprises: for each of the at least one PoI cluster, combining PoIs in the PoI cluster to generate a combined PoI based on at least one of: a weighted average of CI phases measured at the PoIs, or a dominant PoI having a highest peak among the first peaks of the auto-correlation functions associated with the PoIs, and generating a vital signal for a target living being corresponding to the PoI cluster based on a CI phase signal corresponding to the combined PoI, wherein the CI phase signal is associated with all repetitive motions of the target living being.

Clause 10. The system of clause 9, wherein extracting a heartbeat signal from the vital signal comprises: decomposing, for each living being, the CI phase signal associated with the living being to generate the heartbeat signal based on at least one of: a joint optimization of a decomposition of the CI phase signal, or a successive decomposition of the CI phase signal.

Clause 11. The system of clause 10, wherein the joint optimization comprises: determining a number K that represents a quantity of possible signal components of the CI phase signal, wherein K is larger than or equal to a quantity of living beings in the venue; determining a tradeoff factor for balancing bandwidth constraint and data fidelity; iteratively optimizing, based on the tradeoff factor, K signal components of the CI phase signal and center frequencies of the K signal components, based on an objective function that maximizes spectrum sparsity and data fidelity of the CI phase signal at the same time, until a convergence of the objective function; and concurrently generating K decomposed components of the CI phase signal based on the iteratively optimizing.

Clause 12. The system of clause 11, wherein the joint optimization further comprises: determining whether the K decomposed components comprise a heartbeat component, which has an amplitude located within a first value range and has a center frequency located within a second value range, wherein each of the first value range and the second value range is predetermined based on heartbeat statistics.

Clause 13. The system of clause 12, wherein the joint optimization further comprises: when there is a heartbeat component in the K decomposed components, estimating an envelope of the heartbeat component based on at least one of: smoothing, low pass filtering, spline interpolation, B-spline, cubic spline interpolation, polynomial fitting, or moving average, and normalizing the heartbeat component by dividing the heartbeat component with the envelope of the heartbeat component to generate a normalized heartbeat signal for the living being.

Clause 14. The system of clause 12, wherein the joint optimization further comprises: when there is no heartbeat component in the K decomposed components, updating the number K to generate an updated number K' to represent an updated quantity of possible signal components of the CI phase signal, updating the tradeoff factor to generate an updated tradeoff factor for balancing bandwidth constraint and data fidelity, and iteratively optimizing, based on the updated tradeoff factor, K' signal components of the CI phase signal and center frequencies of the K' signal components, based on the objective function that maximizes spectrum sparsity and data fidelity of the CI phase signal at the same time, until a convergence of the objective function, to concurrently generate K' decomposed components of the CI phase signal.

Clause 15. The system of clause 10, wherein the successive decomposition comprises: estimating a dominant component of the CI phase signal, based on at least one of: smoothing, low pass filtering, spline interpolation, or polynomial fitting; removing the dominant component from the CI phase signal to generate a processed CI phase signal; computing a characteristic of a second dominant component of the CI phase signal based on the processed CI phase signal utilizing at least one of: a frequency transform, a trigonometric transform, a fast Fourier transform (FFT), or a wavelet transform; and determining, based on the characteristic, whether the second dominant component is a heartbeat component, which has an amplitude located within a first value range and has a center frequency located within a second value range, wherein each of the first value range and the second value range is related to heartbeat. The characteristic may also be computed by a minimization of an energy function subject to a smoothness constraint.

Clause 16. The system of clause 15, wherein the successive decomposition further comprises: when the second dominant component is a heartbeat component, estimating an envelope of the heartbeat component based on at least one of: smoothing, low pass filtering, spline interpolation, B-spline, cubic spline interpolation, polynomial fitting, or moving average, and normalizing the heartbeat component by dividing the heartbeat component with the envelope of the heartbeat component to generate a normalized heartbeat signal for the living being.

Clause 17. The system of clause 15, wherein the successive decomposition further comprises: when the second dominant component is not a heartbeat component, removing the second dominant component from the CI phase signal to generate an additional processed CI phase signal, computing an additional characteristic of a next dominant component of the CI phase signal based on the additional processed CI phase signal, and determining based on the additional characteristic, whether the next dominant component is a heartbeat component, which has an amplitude located within the first value range and has a center frequency located within the second value range. The additional characteristic may be computed either by a frequency transform or by a minimization of an energy function subject to a smoothness constraint.

Clause 18. The system of clause 10, wherein monitoring the heart rate variability further comprises: for each living being, determining a heartbeat time for the living being at each time instance to compute heartbeat times, based on at least one of: identifying peaks of the heartbeat signal, identifying zero-crossing points of the heartbeat signal, or performing continuous wavelet transform on the heartbeat signal; calculating a plurality of inter-beat intervals based on the heartbeat times; and estimating the heart rate variability for the living being based on statistics of the inter-beat intervals.

Clause 19. The system of clause 2, wherein extracting a heartbeat signal from the vital signal comprises generating, for each living being, the heartbeat signal based on at least one of: a decomposition of the vital signal based on frequency components of the vital signal; or a decomposition of a CI amplitude signal associated with the living being.

Clause 20. The system of clause 1, wherein the transmitter and the receiver are physically coupled to each other.

Clause 21. A wireless device of a wireless monitoring system, comprising: a processor; a memory communicatively coupled to the processor; and a receiver communicatively coupled to the processor, wherein: an additional wireless device of the wireless monitoring system is configured for transmitting a first wireless signal through a wireless channel of a venue, the receiver is configured for receiving a second wireless signal through the wireless channel, the second wireless signal comprises a reflection of the first wireless signal by at least one living being having at least one repetitive motion in the venue, and the processor is configured for: obtaining a time series of channel information (TSCI) of the wireless channel based on the second wireless signal, generating, for each living being of the at least one living being, a vital signal representing all repetitive motions of the living being based on the TSCI, extracting, from the vital signal of each living being, a heartbeat signal, and monitoring, for each living being in the venue, a heart rate variability based on the heartbeat signal.

Clause 22. The wireless device of clause 21, wherein: the at least one living being comprises: a human being or an animal; the first wireless signal is carried on a millimeter wave; each object in the venue has a location determined based on a plurality of spatial bins in the venue; each of the plurality of spatial bins is determined by: a direction and a distance range originating from the receiver; and each direction is associated with at least one of: an angle, an azimuth angle, or an elevation angle.

Clause 23. The wireless device of clause 22, wherein generating the vital signal for each living being comprises: computing a beamforming based on the TSCI; computing a set of time series of directional channel information (CI) each associated with a direction based on the beamforming; for each directional CI associated with a respective direction, computing, for each time instance, a CI amplitude based on the directional CI for the respective direction and a distance range to obtain CI amplitudes over time, computing a time average of the CI amplitudes based on a time window, and detecting object presence at the distance range in the respective direction when the time average is greater than a first threshold, wherein the first threshold is determined adaptively to filter the CI amplitudes at the distance range in the respective direction based on a two-dimensional constant false alarm rate (CFAR); and determining a set of direction-of-interest's (DoIs) each comprising a direction in which object presence is detected.

Clause 24. The wireless device of clause 23, wherein generating the vital signal for each living being further comprises: for each DoI in the set of DoIs and for each distance range, computing a phase variance of a directional CI associated with the DoI over time in a time window, classifying a detected object at the distance range and the DoI as a static object without repetitive motion, when the phase variance is less than a second threshold, and classifying a detected object at the distance range and the DoI as a living being with repetitive motion, when the phase variance is greater than or equal to the second threshold; determining a plurality of target spatial bins for each detected living being, wherein each of the plurality of target spatial bins is determined by a target DoI and a target distance range; and for each target spatial bin, computing an auto-correlation function based on the directional CI associated with the target spatial bin, determining a first peak of the auto-correlation function, classifying a motion of the detected living being at the target spatial bin as a repetitive motion when the first peak is greater than a third threshold, and classifying a motion of the detected living being at the target spatial bin as a random body motion when the first peak is less than or equal to the third threshold.

Clause 25. The wireless device of clause 24, wherein generating the vital signal for each living being further comprises: computing a set of point-of-interest's (PoIs), wherein each PoI in the set of PoIs is associated with a detected living being at the PoI and is a target spatial bin in the venue associated with a repetitive motion of the detected living being at the PoI; clustering the set of PoIs to generate at least one PoI cluster with a total cluster number; determining a quantity of target living beings in the venue based on the total cluster number; and for each of the at least one PoI cluster, combining PoIs in the PoI cluster to generate a combined PoI based on at least one of: a weighted average of CI phases measured at the PoIs, or a dominant PoI having a highest peak among the first peaks of the auto-correlation functions associated with the PoIs, and generating a vital signal for a target living being corresponding to the PoI cluster based on a CI phase signal corresponding to the combined PoI, wherein the CI phase signal is associated with all repetitive motions of the target living being.

Clause 26. The wireless device of clause 21, wherein extracting a heartbeat signal from the vital signal comprises: decomposing, for each living being, a CI phase signal associated with the living being to generate the heartbeat signal based on a joint optimization of a decomposition of the CI phase signal, wherein the joint optimization comprises: determining a number K that represents a quantity of possible signal components of the CI phase signal, wherein K is larger than or equal to a quantity of living beings in the venue, determining a tradeoff factor for balancing bandwidth constraint and data fidelity, iteratively optimizing, based on the tradeoff factor, K signal components of the CI phase signal and center frequencies of the K signal components, based on an objective function that maximizes spectrum sparsity and data fidelity of the CI phase signal at the same time, until a convergence of the objective function, and concurrently generating K decomposed components of the CI phase signal based on the iteratively optimizing.

Clause 27. The wireless device of clause 26, wherein the joint optimization further comprises: determining whether the K decomposed components comprise a heartbeat component, which has an amplitude located within a first value range and has a center frequency located within a second value range, wherein each of the first value range and the second value range is predetermined based on heartbeat statistics.

Clause 28. The wireless device of clause 27, wherein the joint optimization further comprises: when there is a heartbeat component in the K decomposed components, estimating an envelope of the heartbeat component based on at least one of: smoothing, low pass filtering, spline interpolation, B-spline, cubic spline interpolation, polynomial fitting, or moving average, and normalizing the heartbeat component by dividing the heartbeat component with the envelope of the heartbeat component to generate a normalized heartbeat signal for the living being.

Clause 29. The wireless device of clause 27, wherein the joint optimization further comprises: when there is no heartbeat component in the K decomposed components, updating the number K to generate an updated number K' to represent an updated quantity of possible signal components of the CI phase signal, updating the tradeoff factor to generate an updated tradeoff factor for balancing bandwidth constraint and data fidelity, and iteratively optimizing, based on the updated tradeoff factor, K' signal components of the CI phase signal and center frequencies of the K' signal components, based on the objective function that maximizes spectrum sparsity and data fidelity of the CI phase signal at the same time, until a convergence of the objective function, to concurrently generate K' decomposed components of the CI phase signal.

Clause 30. A method of a wireless monitoring system, comprising: transmitting a first wireless signal through a wireless channel of a venue; receiving a second wireless signal through the wireless channel, wherein the second wireless signal comprises a reflection of the first wireless signal by a plurality of human beings in the venue; obtaining a time series of channel information (TSCI) of the wireless channel based on the second wireless signal, wherein each CI comprises at least one of: a channel state information (CSI), channel impulse response (CIR), channel frequency response (CFR), or received signal strength index (RSSI); generating, for each of the plurality of human beings, a vital signal representing all repetitive motions of the human being based on the TSCI; extracting, from the vital signal of each human being, a heartbeat signal; and simultaneously monitoring, for each of the plurality of human beings, a heart rate variability based on the heartbeat signal.

Automobiles have become a daily necessity in current fast-paced world due to its mobility, convenience and comfortableness. Statistics show that the number of worldwide automobiles on-the-road has reached 1.2 billion by 2015. However, in the meanwhile, road traffic crashes result in about 1.35 million deaths around the world each year and leave between 20 and 50 million people with non-fatal injuries, according to World Health Organization. To reduce the number of road accidents and enhance the driving safety, automobile manufacturers and researchers have been working on more and more Advanced Driver Assistance Systems (ADAS). Among many popular topics in autonomous driving, driver's vital sign monitoring is one of the essential components. Continuously monitoring driver's status makes it possible to allow the ADAS to take control of the automobiles in case of emergency, such as when the driver encounters a sudden heart attack, stroke or fatigue, which can be predicted or indicated by using the driver's Heart Rate Variability (HRV), i.e., the variation of the Inter-Beat Intervals (IBI). HRV, in combination with Heart Rate (HR) and Respiration Rate (RR), has been well established as a good indicator of cardiac arrhythmia, alcohol usage, mental stress and drowsiness, and thus predicts the human alertness well.

Traditional driver vital signs monitoring solutions mainly include two categories: sensor-based methods and vision-based methods. The sensor based methods require a driver to wear physiological sensors such as photoplethysmography (PPG), electrocardiogram (ECG) and electroencephalography (EEG) to monitor vital signs. However, it is cumbersome and uncomfortable to wear these dedicated sensors in daily commute. Moreover, wearing sensors may distract driver's attention, degrading the safety and user experience. As a less intrusive solution, vision-based methods utilize image sequences to detect the vital signs including RR, HR and HRV. However, the main drawbacks such as its poor performance in low-light scenarios and the privacy concerns hinder the wide deployment of the vision-based systems.

With the development of wireless sensing, Radio Frequency (RF) based methods have become one of the most promising candidates. Intuitively, the presence of a human subject will affect the RF propagation, i.e., RF signals reflected off human subjects will be modulated by the body movement including chest movement due to respiration and heartbeat. As a result, RF-based systems can estimate vital signs without any physical contact, while preserving the user privacy and operating robustly regardless of the light conditions. Many work have validated the feasibility of RR, HR and HRV monitoring using RF signal. However, most of these solutions focus on indoor scenarios with stationary human subjects, which cannot deal with the noisy in-car environment with engine vibrations, road vibrations, and human body motion. Therefore, accurate RF-based driver vital sign monitoring needs to be further investigated.

Technically, it is non-trivial to enable RF-based driver vital signs monitoring. First, during driving, the driver exhibits frequent and unpredictable motion (e.g., control the steering wheel, head movement to keep track of the car, and body roaming due to acceleration or brake, etc.), which frequently cause dominant motion larger than respiration and heartbeat, and can easily corrupt the periodic variations induced by vital signals. Therefore, it is hard to distill the minute motion caused by vital signals through the raw RF signal.

To overcome the problem, the present teaching discloses a two-step motion compensation algorithm, according to some embodiments. The reflection profile of the driver stays similar considering the resolution of the system and the size of target. Given such an observation, in the first step, the location change of the driver is compensated based on the cross correlation between consecutive Channel Impulse Response (CIR). After that, the reflections corresponding to the same part of the human body will be aligned in the same range-azimuth bin over time. To further remove the fine motion artifacts and recover the periodicity of vital signals revealed in the phase measurement, in the second step, the motion trend is further estimated by smoothing spline and then eliminated. Second, even after eliminating most of the effect of body motion, it is still challenging to extract individual heartbeats from the compound vital signals. This is because that the distance change caused by heartbeat is an order of magnitude smaller than that caused by respiration, and the heartbeat signal is easily to be submerged. Moreover, these subtle cardiogenic body movements lack sharp peak feature as in ECG signals, making it harder to accurately pinpoint the exact timing of heartbeats for HRV estimation.

Figure 12:
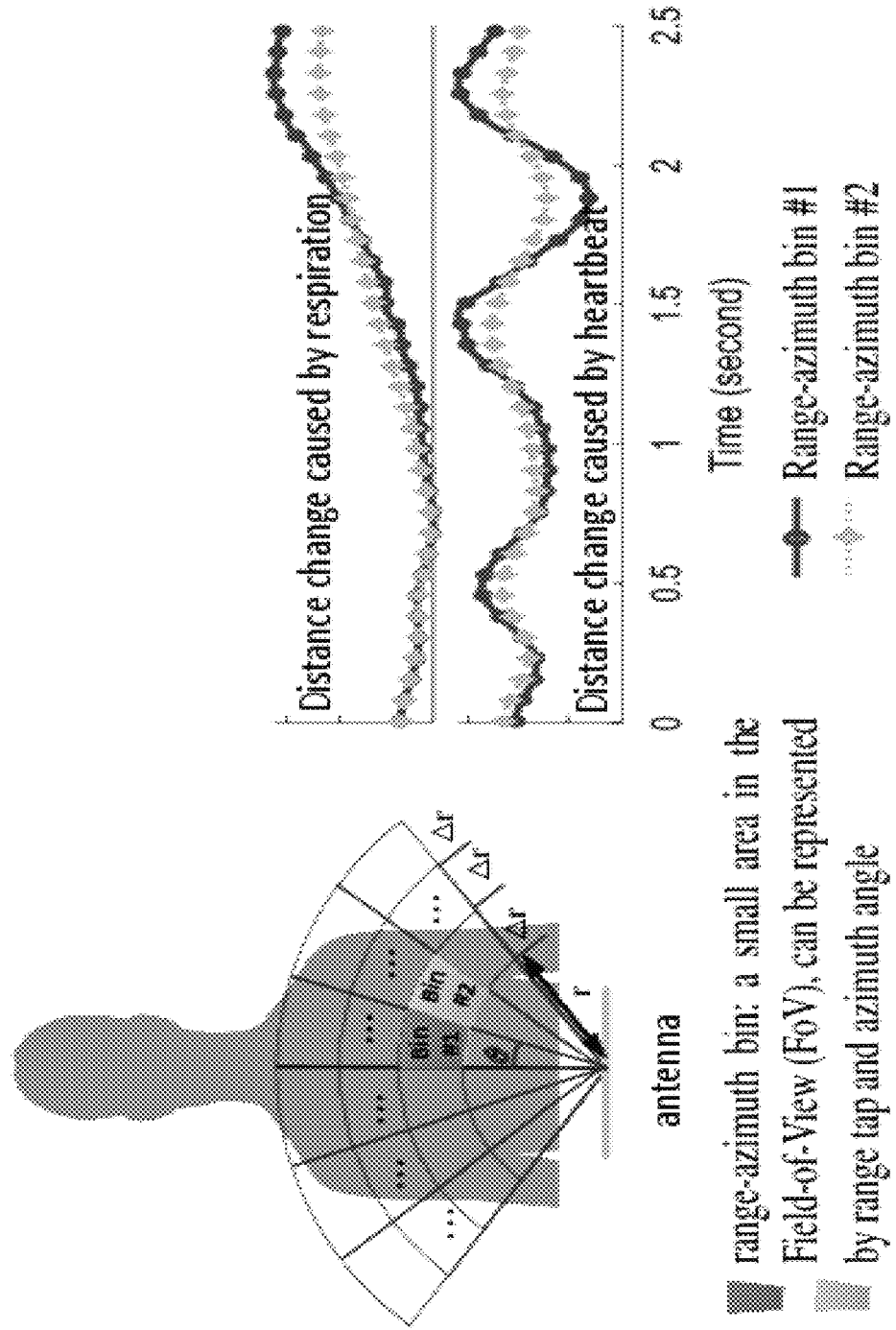
FIG. 12 illustrates exemplary vital signals in different range-azimuth bins, according to some embodiments of the present disclosure.

To tackle these challenges and reconstruct respiration as well as heartbeat signals from the RF reflections, the present teaching discloses a joint decomposition method by exploring following properties of the vital signals. (1) Both respiration and heartbeat signals are quasi-periodic signals, where the normal frequency of respiration and heartbeat are 6-30 Respiration Per Minute (RPM) and 50-120 Beat Per Minute (BPM), respectively. (2) The reflections from the human chest would occupy different range taps and azimuth angles (known as range-azimuth bins as shown in FIG. 12) considering the range-azimuth resolution of the device and the size of human body. Hence, the vital information contained in multiple range-azimuth bins can be jointly optimized to improve the estimation accuracy. (3) The frequency of vital signals reflected by different parts of human chest (corresponding to different range-azimuth bins) stay the same because the reflections come from the same human subject. However, the distance change caused by respiration and heartbeat can be distinct in different parts of human body due to the physiological structure as shown in FIG. 12. Therefore, for all the range-azimuth bins containing vital signals, one would observe periodic signals with the same frequency but different amplitude in the phase measurement.

Leveraging the aforementioned properties, the disclosed system can jointly optimize the decomposition of the vital signals in different range-azimuth bins as an ensemble of band-limited signals. The respiration and heartbeat signals can be further reconstructed by using the empirical mean of the corresponding component over all range-azimuth bins for RR, HR and IBI estimations.

In some embodiments, the disclosed system may be prototyped using a single Commodity Off-The-Shelf (COTS) millimeter-wave (mmWave) radio, with extensive on-road tests conducted to evaluate its performance. In some embodiments, 4 volunteers (2 males and 2 females) help on the data collection, and the testing route is a cycle of 50.7 miles including local routes and highway with different road conditions. The impact of different factors, including the pavement condition, the device location and user heterogeneity are investigated. Experimental results show that the disclosed system can achieve accurate estimations with the median errors of RR, HR and IBI estimation being 0.16 RPM, 0.82 BPM and 46 ms, respectively. The disclosed system is the first RF-based driver vital sign monitoring system that can achieve accurate HRV estimation with motion artifacts. The disclosed system can estimate the driver's vital signs including RR, HR, and more importantly HRV regardless of motion artifacts, which is not achievable in existing works.

Figure 13:
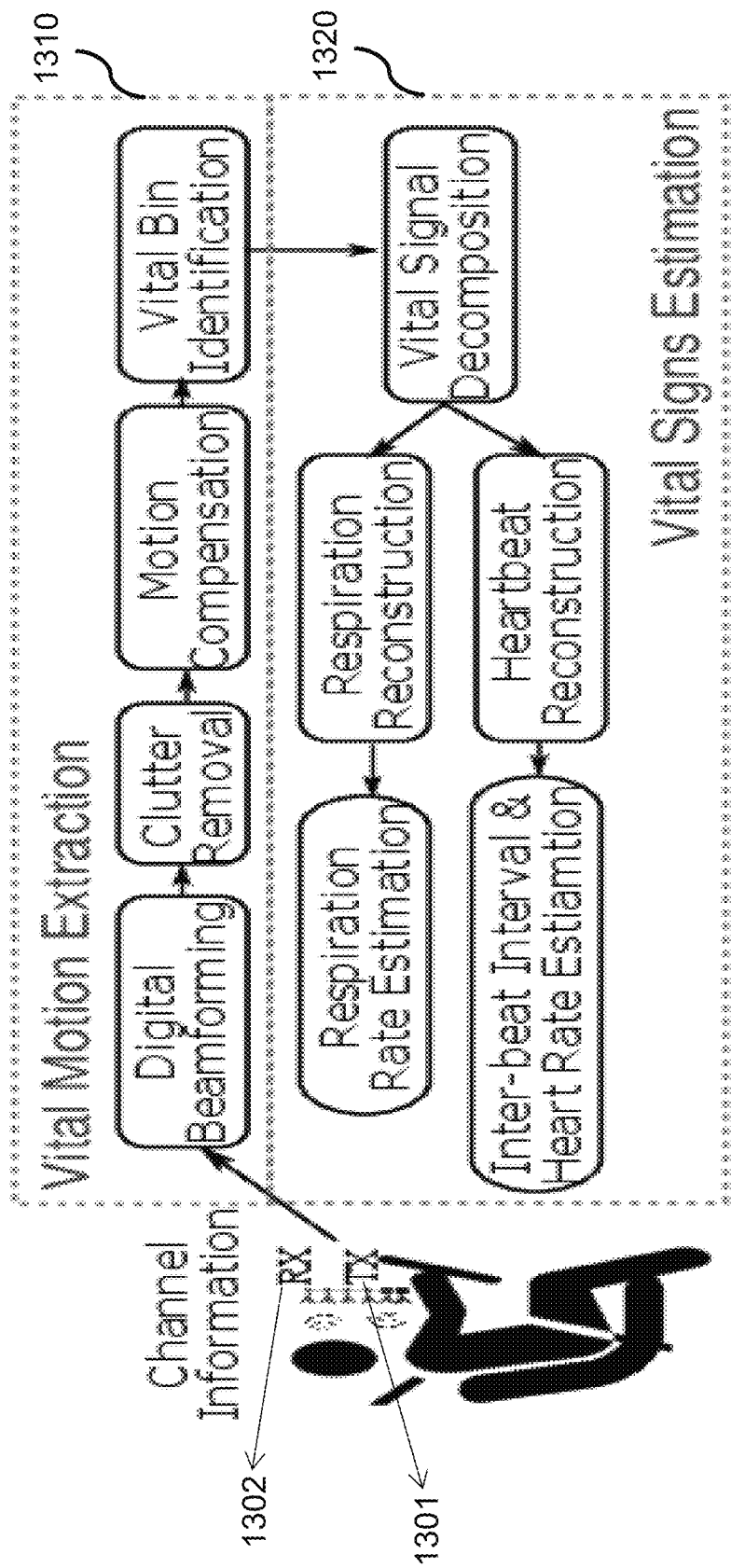
FIG. 13 illustrates an exemplary processing flow of a vital sign monitoring system, according to some embodiments of the present disclosure.

In some embodiments, the disclosed system aims at non-contact driver's vital sign monitoring in practical driving scenarios with inevitable random motions by using a single commodity Frequency-Modulated Continuous Wave (FMCW) radar. According to some embodiments, the pipeline of the system is shown in FIG. 13, which includes two main modules: a vital motion extraction module 1310 and a vital signs estimation module 1320.

A transmitter (Tx) 1301 and a receiver (Rx) 1302 may be used to obtain channel information of a wireless channel based on a wireless signal. The wireless signal may be transmitted by the Tx 1301 and received by the Rx 1302 after reflected by objects and/or human beings through the wireless channel. The wireless signal may be at high frequency band, such as 28 GHz, 60 GHz, 77 GHz. In some embodiments, the Tx 1301 is a Bot as described above and has a structure as shown in FIG. 9; and the Rx 1302 is an Origin as described above and has a structure as shown in FIG. 10.

In the first stage, the vital motion extraction module 1310 extracts the bins containing vital signals from the channel information. A beamforming may be performed on the channel information to get the Channel Impulse Response (CIR) at different range-azimuth bins. Then, the clutter removal is performed to subtract the background reflections. However, vital signals cannot be directly extracted even after background subtraction because the driver's location w.r.t. radar can change over time (e.g., body roaming due to acceleration or brake) during driving. As a result, the vital signals will spread over multiple range bins. Therefore, a motion compensation algorithm is devised to eliminate the effect of large body movement. The location change of the driver is first roughly compensated between consecutive CIRs based on correlation of the CIR amplitude. Then, the subtle motion within the range bin are estimated and eliminated from the CIR phase utilizing smoothing spline. After motion compensation, the range-azimuth bins containing vital signals (a.k.a. vital bins) will show periodic pattern, and the CIR of these bins will be exported for further vital signs estimation.

In the second stage, the vital signs estimation module 1320 estimates drivers' RR, HR and HRV using the vital signals exported by the vital motion extraction module 1310. To enable HRV analysis, heartbeat wave needs to be reconstructed to get the exact time of each heartbeat. However, it is non-trivial to extract the heartbeat signal from the compound vital signals including both respiration and heartbeat movements. To accurately recover the respiration as well as heartbeat signal, the disclosed system can optimize the decomposition of vital signals in all vital bins with multiple band-limited signals concurrently. The extracted respiration and heartbeat signals in all the vital bins are further combined to give an estimate of the respiration and heartbeat wave for RR, HR and IBI estimation.

Figure 14:
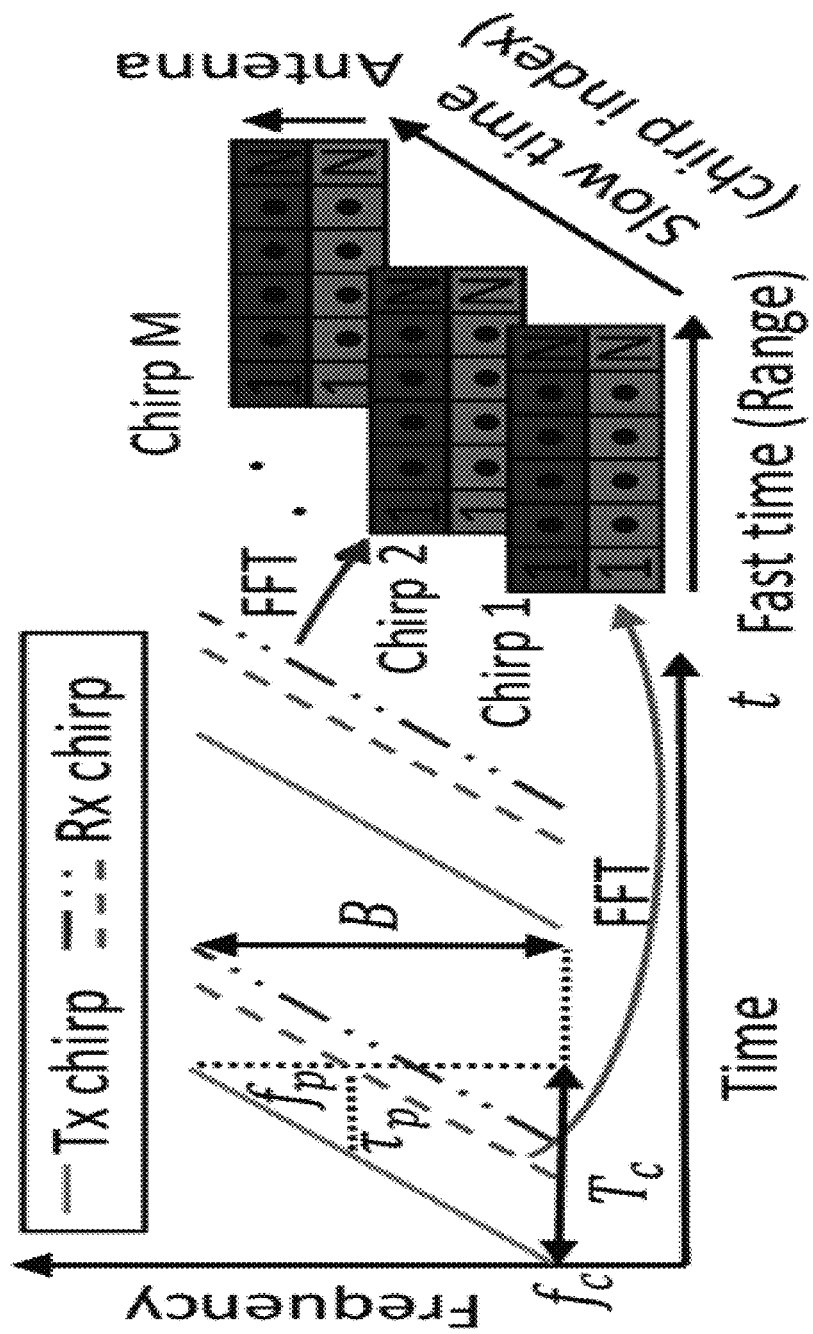
FIG. 14 illustrates exemplary signal transmissions of a vital sign monitoring system using a Frequency-Modulated Continuous Wave (FMCW) radar, according to some embodiments of the present disclosure.

In some embodiments, the disclosed system is built upon an FMCW radar, which transmits a signal with periodic linearly-increasing frequency ramps, as shown in FIG. 14. A chirp in FIG. 14 is a single transmission and the transmitted signal of the m-th chirp can be expressed as $$x_T^m(\tau) = A_T \exp\{-j[2\pi f_c \tau + \pi \frac{B}{T_c} \tau^2]\}, \quad (22)$$

where $f_c$ is the chirp starting frequency, $T_c$ is the chirp duration, B is the bandwidth and $A_T$ is the transmitting power. The reflected signal $x_R^m(r)$ can be expressed as $$x_R^m(\tau) = \sum_{p=1}^{P} A_R \exp\{-j[2\pi f_c(\tau - \tau_p) + \pi \frac{B}{T_c}(\tau - \tau_p)^2]\}, \quad (23)$$

where $A_R$ is the amplitude of the receiving signal, $\tau_p$ stands for the round-trip delay of p-th reflecting path and can be denoted as $$\tau_p = \frac{2d_p}{c},$$

where $d_p$ is the distance between the reflecting object and the device, c is the speed of light, and P denotes the total number of reflecting points in the environment.

Mixing the received signal with a replica of the transmitted signal and following a low-pass filter, the channel information at time instance m can be expressed as $$h^m(\tau) = \sum_{p=1}^{P} A\exp\{-j(2\pi \frac{B\tau_p}{T_c}\tau + 2\pi f_c \tau_p - \pi \frac{B}{T_c}\tau_p^2)\}, \quad (24)$$

where A denotes the channel gain, $\tau_p$ is in nanosecond for the short-range applications, and the term $$\pi \frac{B}{T_c}\tau_p^2$$

is negligible. Therefore, the $h^m(\tau)$ can be written as $$h^m(\tau) = \sum_{p=1}^{P} A\exp\{-j(2\pi \frac{B\tau_p}{T_c}\tau + 2\pi f_c \tau_p)\}, \quad (25)$$

which is a summation of P sinusoidal signals, whose frequency $$f_p \triangleq \frac{B\tau_p}{T_c} = \frac{2Bd_p}{cT_c}$$

depends on the target's distance. In addition, by leveraging multiple antennas of the chipset to increase angle resolution, the channel information can be further denoted as $$h^m(\tau, l) = \sum_{p=1}^{P} A\exp\{-2\pi j(f_p \tau + f_c \tau_p + \frac{d_l \sin\theta}{\lambda_c})\}, \quad (26)$$

where $\lambda_c$ denotes the wavelength of the chirp, $d_l$ is the relative distance introduced by the l-th antenna, $\theta$ is the azimuth angle of the target. This channel information can be converted to CIR by Fast Fourier Transform (FFT) of $h^m(r,l)$, a.k.a Range-FFT, which can be denoted as $$h_{r,l}(m) = \sum_{n=1}^{N} h^m(n, l)\exp\{-j2\pi \frac{rn}{N}\}, \quad (27)$$

where $h_{r,l}(m)$ denotes the CIR of l-th antenna element and r-th range tap r at time instance m, n denotes the sample index after digitizing the $h^m(r,l)$ over fast-time $\tau$, and N is the total number of samples per chirp.

In a real-world setting, extracting vital motions from the RF signal is not trivial. Due to the presence of various clutters in car (e.g., chairs, metal objects, ceilings, etc.), it is hard to filter the RF reflections off human body. Moreover, since body motion will be involved during driving, the periodicity of the reflected signal caused by vital motions can be corrupted, complicating the detection of vital signals.

In some embodiments, to determine the range and the direction of the reflecting objects, the disclosed system employs digital beamforming over all antennas for each range tap. For example, the Bartlett beamformer may be used, where the coefficient of the l-th antenna towards azimuth angel $\theta$ is $$s_l(\theta) = \exp\left(-2\pi j \frac{d_l \sin\theta}{\lambda_c}\right). \quad (28)$$

The beamformed CIR corresponding to range r and azimuth angle $\theta$ can be expressed as $$h(r,\theta,m) = s^H(\theta) h_{r,l}(m) + \epsilon(m), \quad (29)$$

where $s(\theta) = [s_1(\theta), s2(\theta), \ldots, s_L(\theta)]^T$ is the steering vector towards angle $\theta$. $h_{r,l}(m) = [h_{r,1}(m), h_{r,2}(m), \ldots, h_{r,L}(m)]^T$ is the channel information vector at range tap r. $\epsilon(m)$ is the additive white Gaussian noise assumed to be Independent and Identically Distributed (I.I.D) for different range-azimuth bins.

Figure 15B:
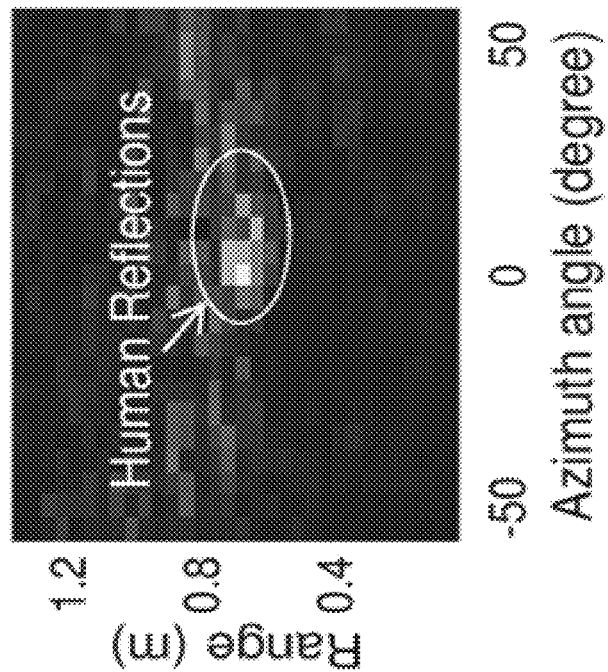
FIG. 15B illustrates an exemplary CIR amplitude after clutter removal, where the reflections corresponding to the driver can be easily identified, according to some embodiments of the present disclosure.
Figure 15A:
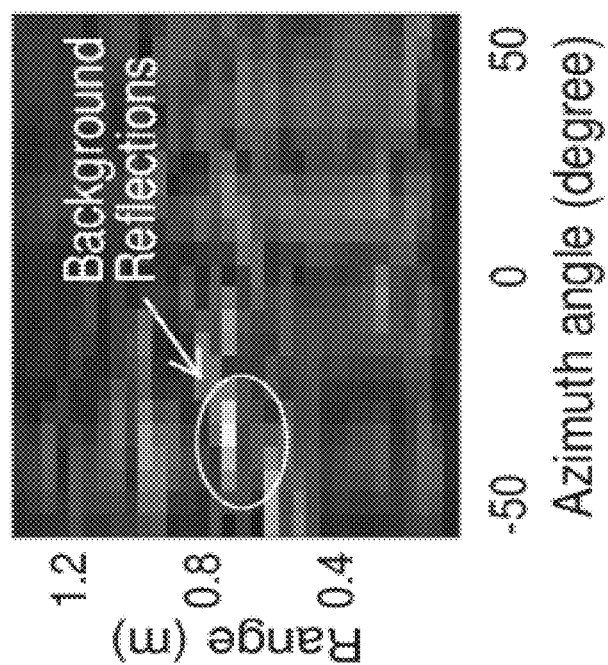
FIG. 15A illustrates an exemplary CIR amplitude before clutter removal, where the reflections from the driver are submerged in the background reflections, according to some embodiments of the present disclosure.

In some embodiments, to locate the range-azimuth bins corresponding to the driver and reduce the impact of reflections from static objects in the vehicle, the disclosed system deploys a clutter removal algorithm to subtract the CIR from the background. The reflections from the static object is reasonably assumed to be invariant within a certain period of time, while the reflections from the driver change over time due to human motion (including body motion and motion caused by vital signals). The background profile can be estimated by taking average of the CIR over slow-time, and the calibrated CIR can be denoted as $$\hat{h}(r, \theta, m) = h(r, \theta, m) - \frac{1}{M}\sum_{i=1}^{M} h(r, \theta, m-i), \tag{30}$$

where M is the number of samples used for clutter removal. FIGS. 15A and 15B show the effect of the background cancellation, where the raw CIR before clutter removal is shown in FIG. 15A, and the corresponding calibrated CIR after clutter removal is shown in FIG. 15B. As shown in FIGS. 15A and 15B, clutter removal reduces the background noise significantly.

In some embodiments, after extracting the dynamic CIR corresponding to the driver, the system can get the range-azimuth bins contributed by the vital signals (a.k.a. vital bins). The vital bins can be easily identified by checking the periodicity of the phase signal if the human subject stays stationary. However, the assumption of the stationary human subject barely holds in the driving scenario. To recover the periodic vital signals from the CIR involving human motion, the disclosed system uses a two-step motion compensation algorithm.

Figure 16:
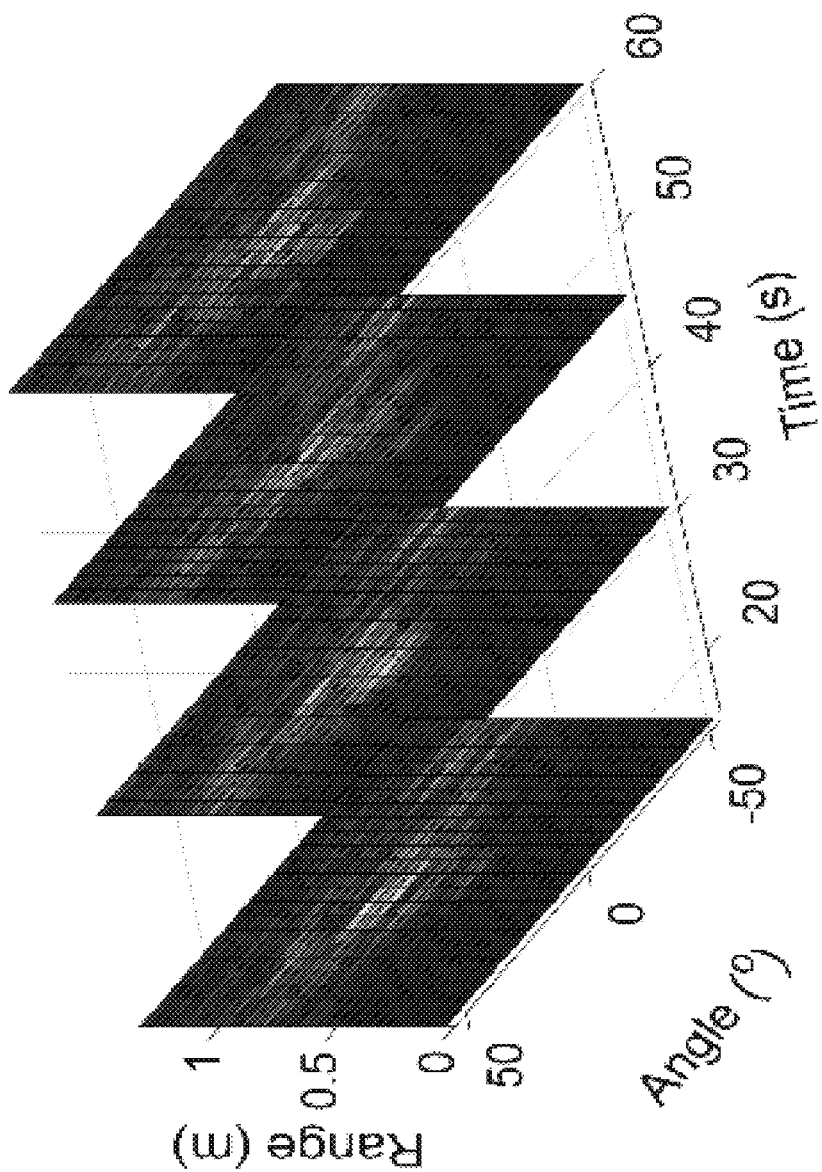
FIG. 16 illustrates an example of consecutive frame after clutter removal, according to some embodiments of the present disclosure.

When there is a large body motion, the location of range-azimuth bins corresponding to human subject will change, as shown in FIG. 16, where the human subject sits at around 0.5m away from device at azimuth angle 0°. The human subject sways the body back-and-forth, resulting in the change of reflecting locations. The amplitude of CIR measurement is shown every 15 s, for example. The profile of human reflections stays similar, as shown in FIG. 16. Therefore, to remove body movement, the 2-dimensional cross correlation between consecutive CIRs is calculated. Then the CIR at each time instance is circularly shifted to the point corresponding to the maximum cross correlation.

Figure 17:
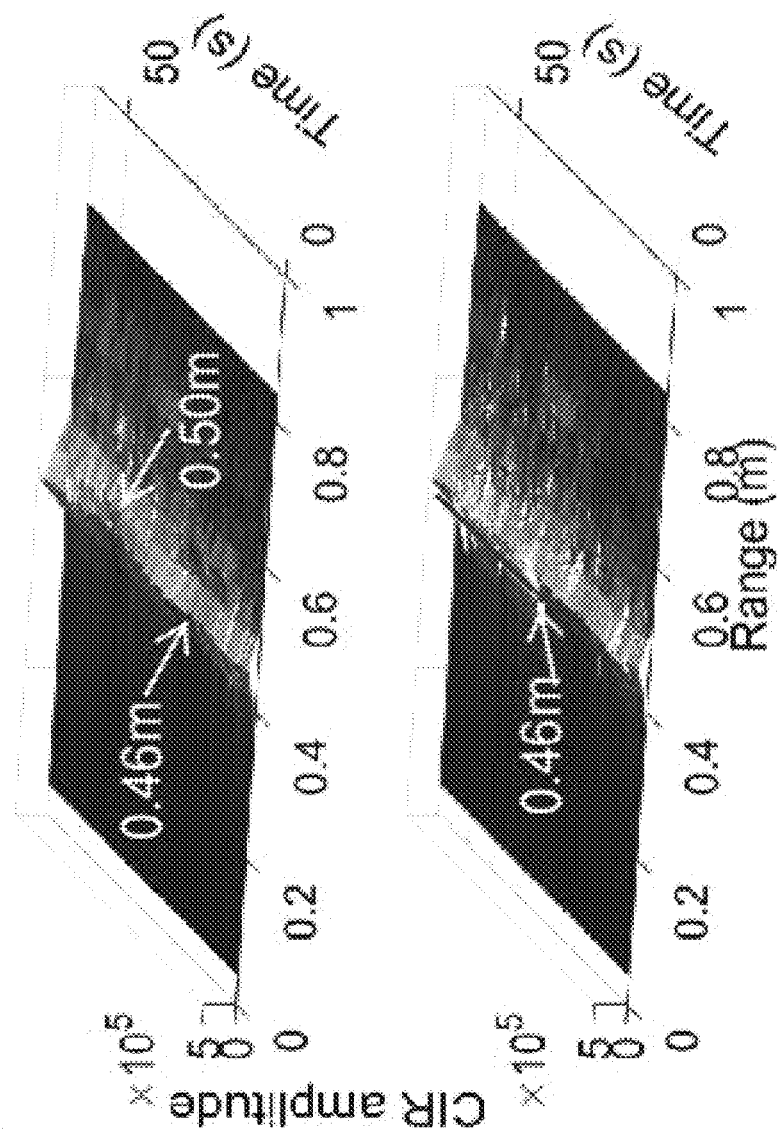
FIG. 17 illustrates an example of large body movement compensation, according to some embodiments of the present disclosure.
Figures 18A, 18B:
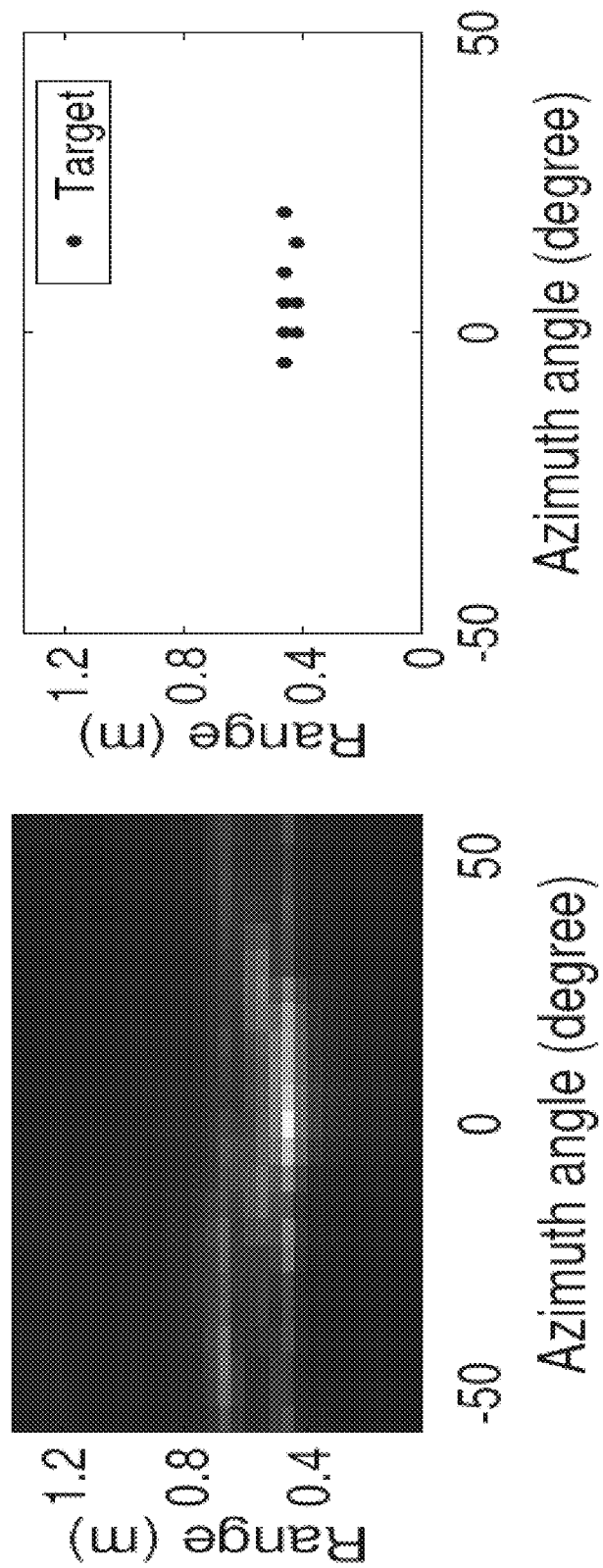
FIG. 18A illustrates an average of the CIR amplitude over 1-min window after large body motion compensation during an exemplary target detection, according to some embodiments of the present disclosure.
FIG. 18B illustrates bins corresponding to the driver by using CFAR detector during an exemplary target detection, according to some embodiments of the present disclosure.

FIG. 17 shows the amplitude of 1-minute CIR before and after body movement compensation. For visualization, the CIR is plotted at azimuth angle 0° over range [0,0.9]m. The upper figure shows 1 minute CIR amplitude at azimuth angle 0° over range [0,0.9]m, where the distance between human subject and device changes over time. The lower figure shows the corresponding CIR amplitude after large body movement compensation, where the range tap of the human subject stays the same. It is shown that after the large body movement compensation, the bins correspond to human subject have been aligned. The 2-D Constant False Alarm Rate (CFAR) detector will be further applied over the CIR after aligning the human subject, and the candidate bins with human subject can be selected as shown in FIGS. 18A and 18B.

Figure 19B:
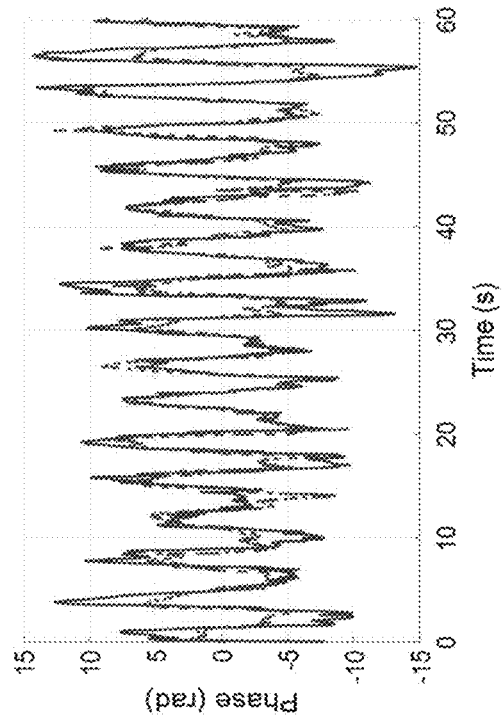
FIG. 19B illustrates phase measurement after an example of fine movement cancellation, according to some embodiments of the present disclosure.
Figure 19A:
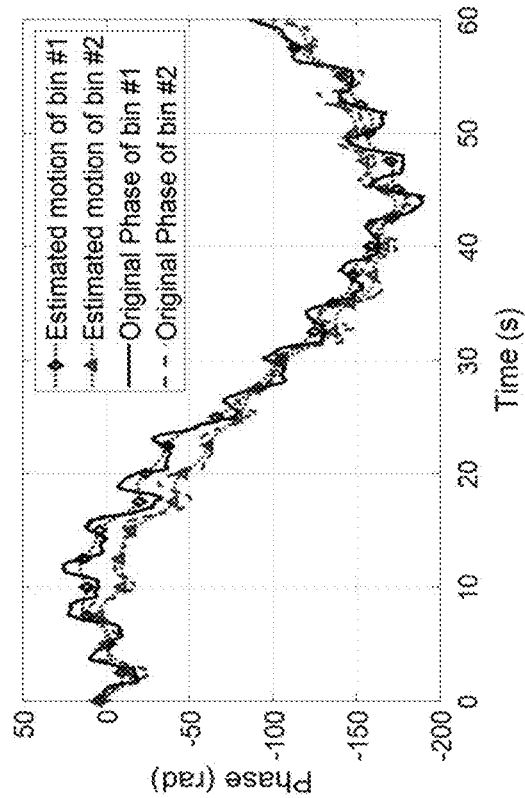
FIG. 19A illustrates an example of fine movement cancellation, where original unwrapped phase measurement from two different vital bins (in solid lines) and the corresponding estimated motion (in dashed lines), according to some embodiments of the present disclosure.

Although the candidate range-azimuth bins corresponding to human subject have been aligned and selected in the first step, it is still hard to locate those bins reflected by chest with periodic vital signals. The reason is that the first step can only remove the motion artifacts that are larger than the range-azimuth resolution, however, it cannot deal with the fine movements within the range-azimuth resolution. FIG. 19A shows an example of the unwrapped phase measurement of the candidate range-azimuth bins after large body movement compensation in solid lines, where the slow trend is caused by the fine movements. To recover the periodicity of vital signals, the system may further eliminate the impact of these fine movements.

In some embodiments, let $y_{r,\theta}=[y_{r,\theta}(1), y_{r,\theta}(2), \ldots, y_{r,\theta}(M)]$ to be the unwrapped phase sequence corresponding to the range r and the azimuth angle $\theta$ at the observation window, where M is the total number of samples. $[t_1, t_2, \ldots, t_M]$ denotes the time corresponding to each observation. The operation of the fine movement elimination is performed within the same range-azimuth bin over slow time.

In some embodiments, to remove the motion artifacts that have larger distance change and lower frequency compared to the vital motions, the estimation of the phase change caused by motion artifacts can be obtained by $$\min_{\hat{f}} \sum_{m=1}^{M} \{y(m) - \hat{f}(t_m)\}^2 + \lambda \int \hat{f}''(t)^2 dt, \tag{31}$$

where $\lambda \geq 0$ is a smoothing parameter. The second term evaluates the smoothness of a function. $\hat{f}$ is the estimate of the phase change caused by motion, defined as $$\hat{f}(t) = \sum_{m=1}^{M} \hat{f}(t_m) f_m(t), \tag{32}$$

where $f_m(t)$ are a set of spline basis function. In some embodiments, B-spline is used as the spline basis. Let $\hat{P}=[\hat{f}(t_1), \ldots, \hat{f}(t_M)]^T$, and the roughness penalty has the form $$\int \hat{f}''(t)^2 dt = \hat{P}^T A \hat{P}, \tag{33}$$

where the elements of A are $\int f_i''(t) f_j''(t) dt$. Therefore, one can rewrite Eqn. (31) as $$\min_{\hat{P}} \{y - \hat{P}\}^T \{y - \hat{P}\} + \lambda \hat{P}^T A \hat{P}, \tag{34}$$

where the minimizer of Eqn. (34) is obtained as $$\hat{P}^* = (I+\lambda A)^{-1} y. \tag{35}$$

Figure 19C:
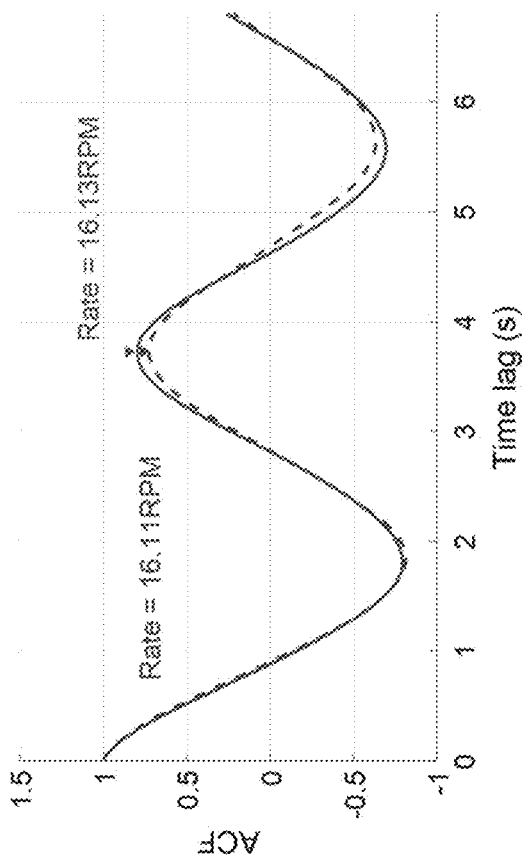
FIG. 19C illustrates the ACF of the calibrated phase measurement during the example of fine movement cancellation, according to some embodiments of the present disclosure.

The estimation of motion can be obtained by $$\hat{f}(t) = \hat{P}^{*T} f(t), \tag{36}$$

where f(t) is the vector form of the spline basis function. The estimated motion artifacts can then be removed to get the clean phase revealing the vital information. FIGS. 19A to 19C illustrate the effect of fine movement cancellation, where the dashed lines in FIG. 19A show the estimated phase measurement caused by body movement. FIG. 19B shows the phase measurement after the motion artifacts are removed, where the periodicity caused by vital signals appears. The above fine movement elimination is performed over all candidate bins selected by CFAR detector and the cleaned phase of each candidate bin is saved for further analysis.

In some embodiments, after motion compensation, the phase information corresponding to the human chest show periodicity due to the modulation of both respiration and heartbeat, as shown in FIG. 19B. To filter out the bins reflected by other parts of human body (i.e., bins dominated by motion), the system can check the periodicity of the phase signals over slow time by examining their Auto-Correlation Function (ACF). The reason is that when the phase measurement contains vital signals, a peak can be observed at τ* in its corresponding ACF, which reveals the time duration of a breathing cycle. FIG. 19C shows an example of the ACF of the phase measurement corresponding to human chest, where the time duration of a breathing cycle is about 3.7s, correspond to 16.1 RPM. The system can check the periodicity over all candidate bins corresponding to the human subject, and those bins whose peak located within the range of normal human RR are identified as vital bins for further analysis.

In some embodiments, the vital bins identified by the previous module can only reflect the compound distance change caused by respiration and heartbeat. To further estimate the vital signs including RR, HR, and HRV, the system can reconstruct the distance change caused by respiration and heartbeat respectively. For simplicity, in the following analysis, the analog form of the signal model is directly used.

In some embodiments, let $y(t)=[y_1(t), y_2(t), \ldots, y_B(t)]^T$ denote the vector of the phase signals of all the B vital bins. As the phase signal after movement elimination is a mixture of vital signals, one can obtain $$y(t)=s_r(t)+s_h(t)+n(t). \quad (37)$$

where $s_r(t)$ and $s_h(t)$ denote the vector of respiration and heartbeat signal respectively, n(t) is the random phase offset introduced by noise, which is independent with the phase change caused by vital signs. To decompose the phase and get the estimate of vital signs, one can leverage the following properties. First, both respiration and heartbeat are quasi-periodic signals, whose periodicity changes slightly over time. Second, the periodicity of signals corresponding to respiration and heartbeat should stay the same in different vital bins since these signals are modulated by the same person. Third, the distance change caused by respiration and heartbeat can be different in different parts of human body due to the physiological structure (i.e., the distance change in different vital bins can be distinct).

The phase signal, therefore, can be decomposed as an ensemble of band-limited signals, denoted as $\{u_k(t)\}_{k=1}^K$, where for each component $u_k(t)=[u_{\{k,1\}}(t), u_{\{k,2\}}(t), \ldots, u_{\{k,B\}}(t)]^T$, the decomposed signals w.r.t. all vital bins should be compact around the same center frequency $\omega_k$ (corresponding to the property a and b). Moreover, the distance change in different vital bins should be optimized separately (corresponding to property c). The decomposition may be modeled as $$\min_{u_{k,b} \in \mathcal{U}, \omega_k \in \Omega} \alpha \sum_{k=1}^K \sum_{b=1}^B \left\| \partial t \left[ \left( \delta(t) + \frac{j}{\pi t} \right) * u_{k,b}(t) \right] \exp(-j\omega_k t) \right\|_2^2 + \quad (38)$$

$$\sum_{b=1}^B \left\| y_b(t) - \sum_{k=1}^K u_{k,b}(t) \right\|_2^2,$$

where $\mathcal{U}\{u_{1,1}, u_{1,2}, \ldots, u_{1,B}, \ldots, u_{K,B}\}$ and $\Omega = \{\omega_1, \ldots, \omega_K\}$ denote the set for all components and their center frequencies, respectively. The first term in Eqn. (38) represents the bandwidth constraint, which is measured by the sum of the $L_2$ norm of the gradient of the analytic signal corresponding to each component. The second term is the fidelity constraint, which is evaluated by the quadratic penalty w.r.t. reconstruction. α is a parameter for balancing the bandwidth constraint and data fidelity. The optimization problem in Eqn. (38) can be solved by alternatively updating $\mathcal{U}$ and $\Omega$ until convergence.

The system may then calculate a minimization w.r.t. $u_{k,b}$. In some embodiments, to update the k-th component for vital bin b, the subproblem can be written as $$u_{k,b}(t) = \arg \min_{u_{k,b}(t)} \alpha \left\| \partial t \left[ \left( \delta(t) + \frac{j}{\pi t} \right) * u_{k,b}(t) \right] \exp(-j\omega_k t) \right\|_2^2 + \quad (39)$$

$$\left\| y_b(t) - \sum_{i=1}^K u_{i,b}(t) \right\|_2^2.$$

By using the Parseval theorem, the problem is equivalent to $$\mathcal{U}_{k,b}(\omega) = \arg \min_{u_{k,b}(\omega)} \alpha \left\| j\omega[(1 + \text{sgn}(\omega + \omega_k))\mathcal{U}_{k,b}(\omega + \omega_k)] \right\|_2^2 + \quad (40)$$

$$\left\| \mathcal{Y}_b(\omega) - \sum_{i=1}^K \mathcal{U}_{i,b}(\omega) \right\|_2^2,$$

where $\mathcal{U}_{k,b}(\omega)$ and $\mathcal{Y}_b(\omega)$ are the Fourier transfer of $u_{k,b}(t)$ and $y_b(t)$ respectively. After performing change of variables $\omega \leftarrow \omega - \omega_k$ in the first term, and using the Hermition symmetry of the real signals in the spectrum for the second term, the above problem can be rewritten as $$\mathcal{U}_{k,b}(\omega) = \quad (41)$$

$$\arg \min_{u_{k,b}(\omega)} \int_0^\infty 4\alpha(\omega - \omega_k)^2 |\mathcal{U}_{k,b}(\omega)|^2 + 2 \left| \mathcal{Y}_b(\omega) - \sum_{i=1}^K \mathcal{U}_{i,b}(\omega) \right|^2 d\omega.$$

The updated solution can be expressed as $$\mathcal{U}_{k,b}(\omega) = \frac{\mathcal{Y}_b(\omega) - \sum_{i,i \neq k} \mathcal{U}_{i,b}(\omega)}{1 + 2\alpha(\omega - \omega_k)^2}. \quad (42)$$

The system may then calculate a minimization w.r.t. $\omega_k$. The center frequencies $\omega_k$ only appear in the bandwidth constraint and thus the updating function can be written as $$\omega_k = \arg\min_{\omega_k} \sum_{b=1}^B \left\| \partial t \left[ \left( \delta(t) + \frac{j}{\pi t} \right) * u_{k,b}(t) \right] \exp(-j\omega_k t) \right\|_2^2. \quad (43)$$

As discussed above, one can find the optimum in Fourier domain, and have $$\omega_k = \arg\min_{\omega_k} \sum_{b=1}^B \int_0^\infty (\omega - \omega_k)^2 |\mathcal{U}_{k,b}(\omega)|^2 d\omega. \quad (44)$$

The minimizer of the above problem is $$\omega_k = \frac{\sum_b \int_0^\infty \omega |\mathcal{U}_{k,b}(\omega)|^2 d\omega}{\sum_b \int_0^\infty |\mathcal{U}_{k,b}(\omega)|^2 d\omega}. \quad (45)$$

Figure 20A:
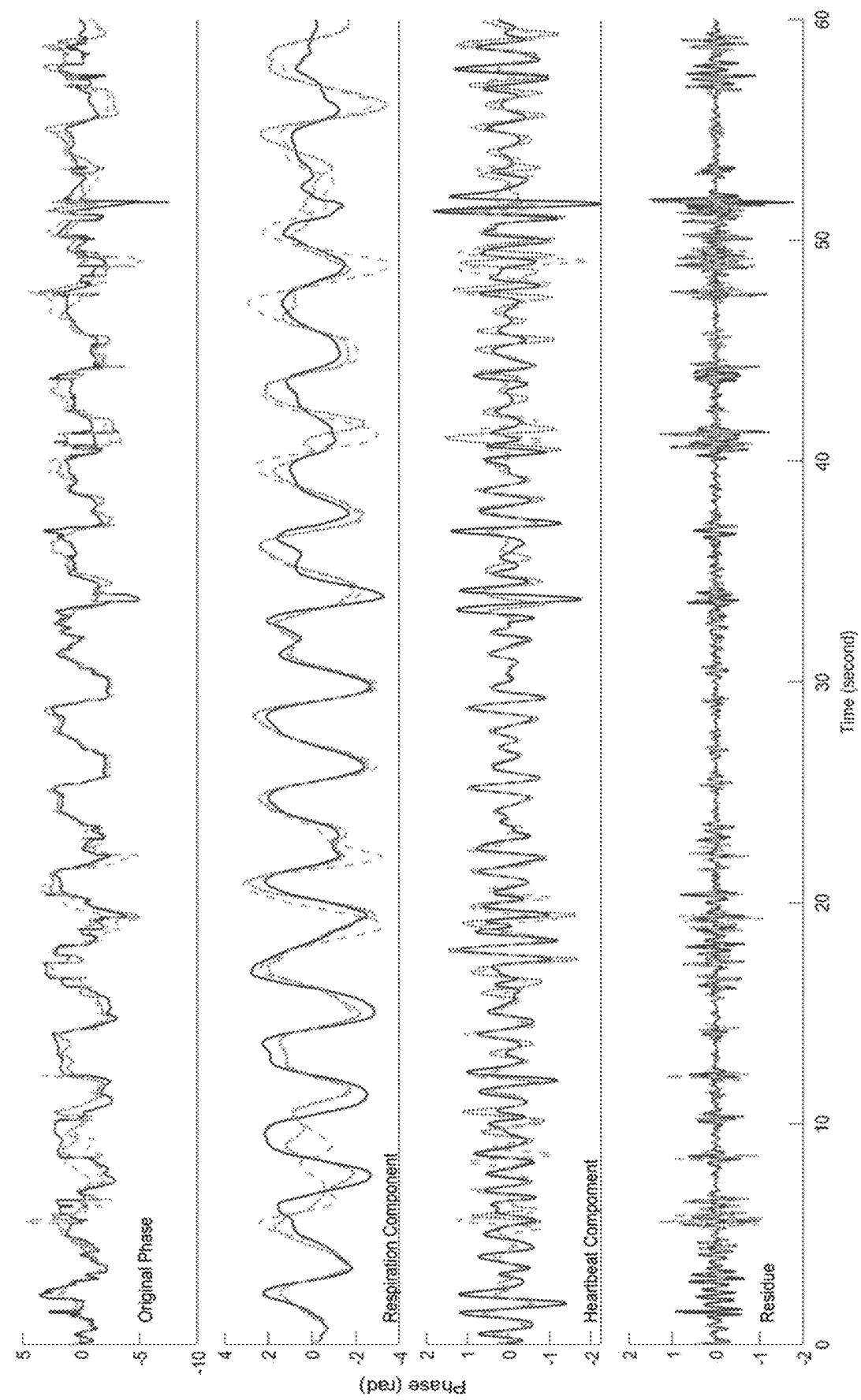
FIG. 20A illustrates a decomposition result in the time domain of an example of phase decomposition of 3 vital bins, according to some embodiments of the present disclosure.
Figure 20B:
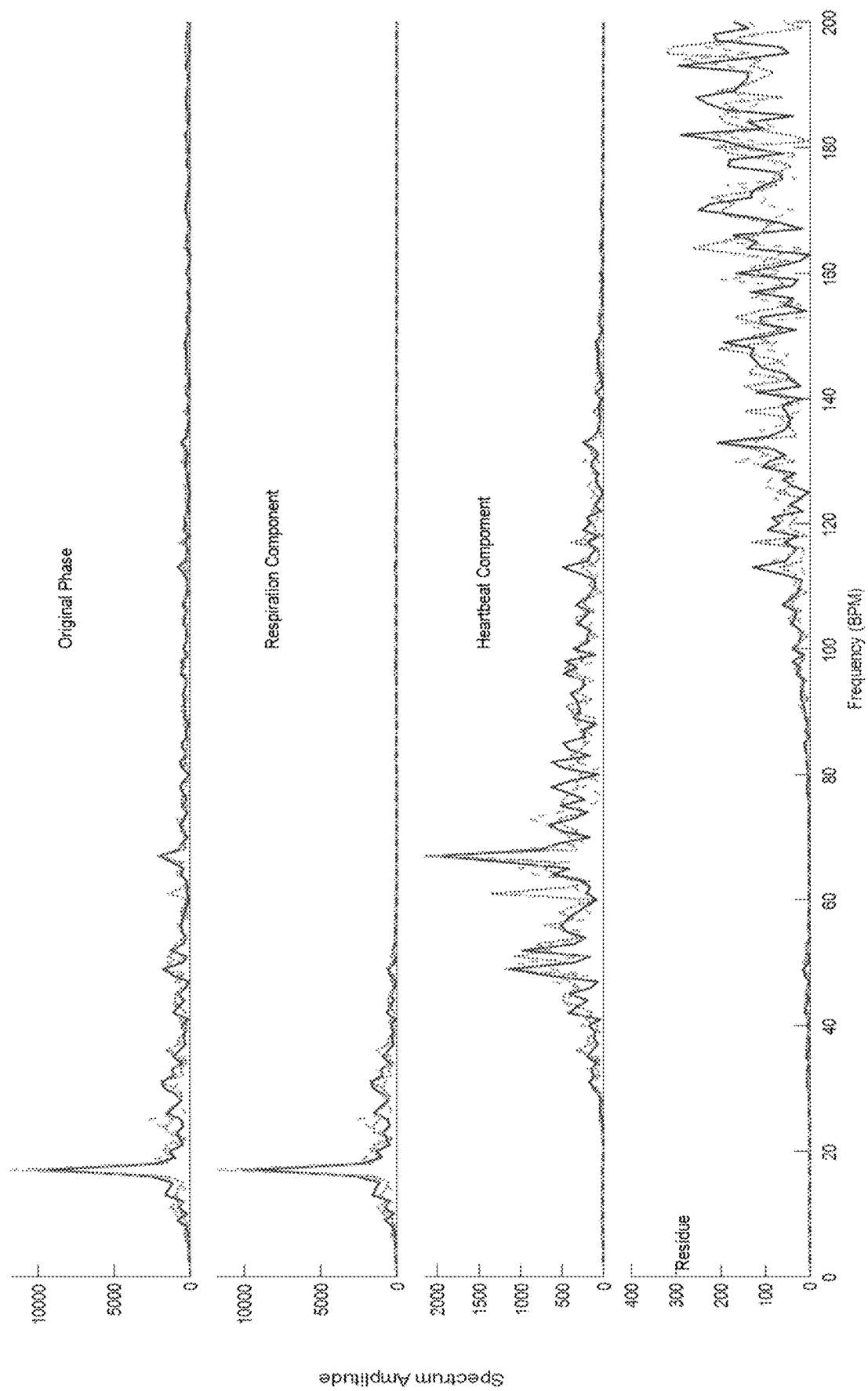
FIG. 20B illustrates corresponding spectrum of each decomposed component of an example of phase decomposition of 3 vital bins, according to some embodiments of the present disclosure.

FIGS. 20A and 20B show an example of vital signals decomposition, where the time and frequency domain of the original phase as well as the decomposition components are shown in FIG. 20A and FIG. 20B, respectively. The first sub-figure in FIG. 20A shows the phase measurement after motion cancellation. The respiration and heartbeat component are shown in the second and third sub-figures of FIG. 20A, respectively. The fourth sub-figure of FIG. 20A shows the decomposition residue. The information of 3 different vital bins is shown. Although the distance change of different vital bins are distinct, as shown in FIG. 20A, the periodicity of the signal of each component stays the same, as shown in FIG. 20B. In other words, components corresponding to vital signals are perfectly aligned over all vital bins, e.g., the first component represents the distinct displacement cause by respiration over different vital bins, and the second component represents the distinct displacement caused by heartbeat over different vital bins. The residue of the decomposition contains noise including car vibrations, as shown in FIGS. 20A and 20B. In some embodiments, to further reduce the noise impact, the system can reconstruct the vital signals by combining the signals of all vital bins using empirical mean, i.e., $$s_r(t) = \frac{1}{B}\sum_b u_{i,b}(t) \text{ and } s_h(t) = \frac{1}{B}\sum_b u_{j,b}(t),$$

where the i-th and j-th components correspond to the respiration signal and heartbeat signal respectively. The RR is estimated by finding the first peak of the ACF of the estimated respiration signal, as shown in FIG. 19C. In addition, the FFT is further performed on the estimated heartbeat signal to get the estimation of HR. Moreover, the exact time of each heartbeat can be further extracted from the reconstructed heartbeat wave to estimate the IBI.

Figure 21B:
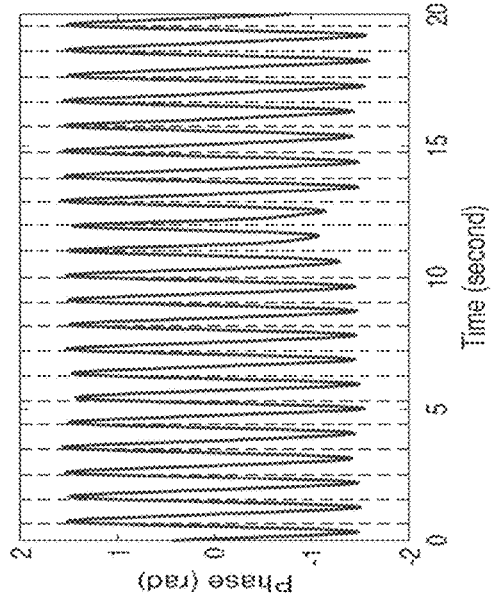
FIG. 21B illustrates estimated heartbeat signal of a vital sign monitoring system compared with the ECG sensor result, where the ground-truth from ECG sensor are marked as vertical dashed lines, according to some embodiments of the present disclosure.
Figure 21A:
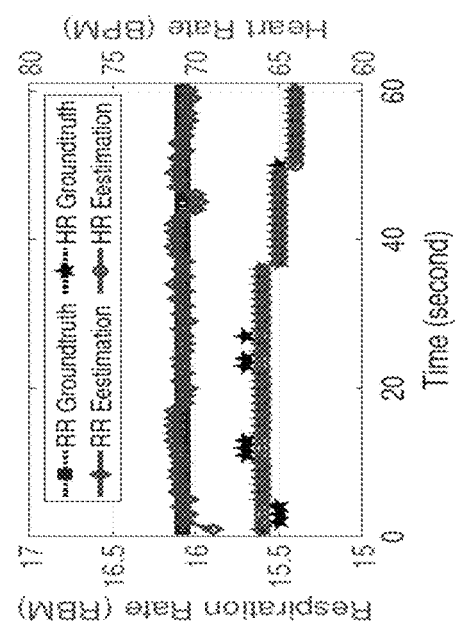
FIG. 21A illustrates exemplary RR and HR estimation result of a vital sign monitoring system, according to some embodiments of the present disclosure.
Figure 21C:
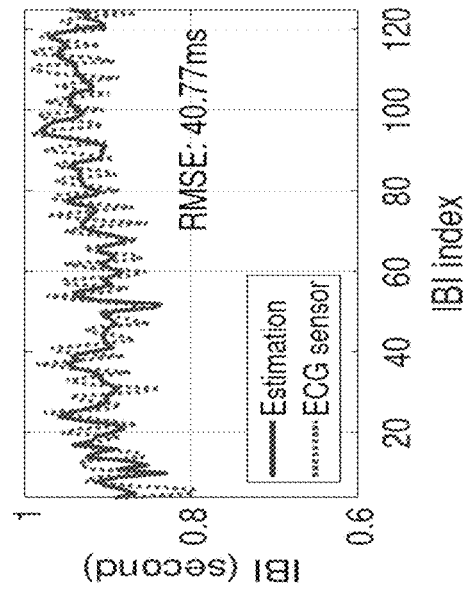
FIG. 21C illustrates estimated IBI of a vital sign monitoring system compared with ground-truth from the ECG sensor, according to some embodiments of the present disclosure.

FIGS. 21A to 21C show the estimated vital signs versus their ground-truths of a 2-minute dataset, where a 1-minute window is employed for the time-frequency domain transform (i.e., ACF and FFT). The estimated RR and HR are shown in solid lines in FIG. 21A, which match with the ground-truth, shown as dashed lines in FIG. 21A. FIG. 21B shows a segment of the estimated heartbeat wave, and the ground-truth of the exact time of each heartbeat is marked as vertical dashed lines. The estimated IBIs of the whole data and their corresponding ground-truth are shown in FIG. 21C. Clearly, the disclosed system achieves high accuracy in vital signs estimation, and the Root-Mean-Squared-Error (RMSE) of IBI estimation in FIG. 21C is 40.77 ms, corresponding to the 96% relative accuracy.

According to some embodiments, extensive experiments are performed to evaluate the performance of the disclosed system. One can compare the performance with the state-of-art work under different experimental settings. In some embodiments, one can conduct experiments using a COTS mmWave radar, where the 2 Tx antennas and 4 Rx antennas are configured in TDM-MIMO mode. The device can achieve a theoretical azimuth resolution of 15°, and the field-of-view (FoV) is 100° in horizontal plane, which is large enough to cover the driver. The parameters corresponding to the FMCW radar setting are listed in Table II. The ground truth of heartbeat is captured by a commercial ECG sensor, and the ground truth of breathing is measured by a respiration belt.

TABLE II

| Parameters used | | | |
|---|---|---|---|
| System Parameters | Value | System Parameters | Value |
| Starting Frequency | 77 GHz | Max. Range | 1.2 m |
| Slow Time Sampling | 1000 chirps/sec | Range Resolution | 3.75 cm |
| Chirp Duration | 57.14 us | Field-of-View | [−50°, 50°] |

In some embodiments, 4 volunteers (2 males and 2 females) are recruited to help on the data collection including 2 different device locations. All of the participants do not have any cardiac history, and more information about the testers is shown in Table III. The driving route is a cycle of 50.7 miles including local routes and highway, where the road conditions can be referred to GIS Dataset. During the data collection, the driver is driving following their own habits with no further constraints, and a copilot is responsible for collecting data.

TABLE III

| Information of the participants | | | | |
|---|---|---|---|---|
| Subject ID | 1 | 2 | 3 | 4 |
| Gender | M | M | F | F |
| Height (cm) | 174 | 172 | 160 | 166 |
| Weight (Kg) | 79.8 | 70 | 61.4 | 50 |
| BMI | 26.36 | 23.66 | 23.98 | 18.14 |

To further evaluate the performance of the disclosed system, one can compare it with the state-of-art work, $V^2$iFi, which estimates driver's vital signs using the CIR of a UWB radar. With assumption that the distance change caused by vital signals are identical in different vital bins, $V^2$iFi estimates the respiration and heartbeat signal by Multi-Sequence Variational Mode Decomposition (MS-VMD). The $V^2$iFi cannot estimate vital signs when drivers have body motion. For fair comparison, motion compensation disclosed here is also applied to $V^2$iFi to remove the motion artifacts before estimating the vital signals.

Figure 22:
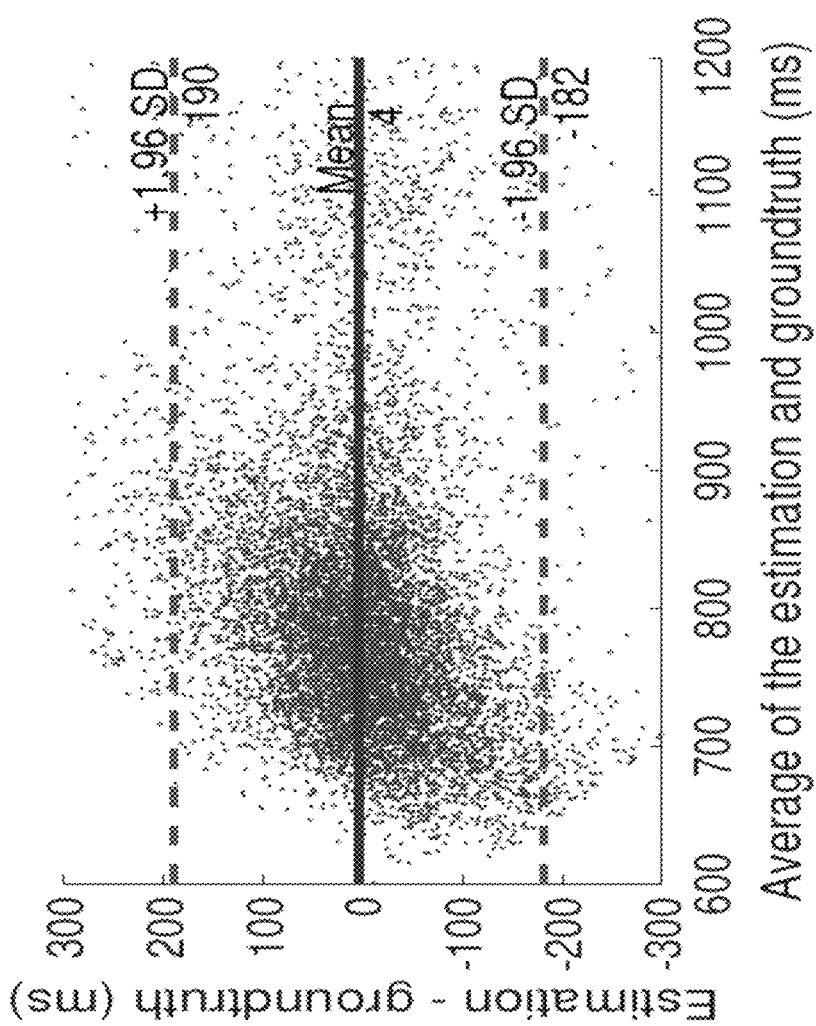
FIG. 22 illustrates an exemplary overall performance of a vital sign monitoring system based on a Bland-Altman plot, according to some embodiments of the present disclosure.
Figure 23A:
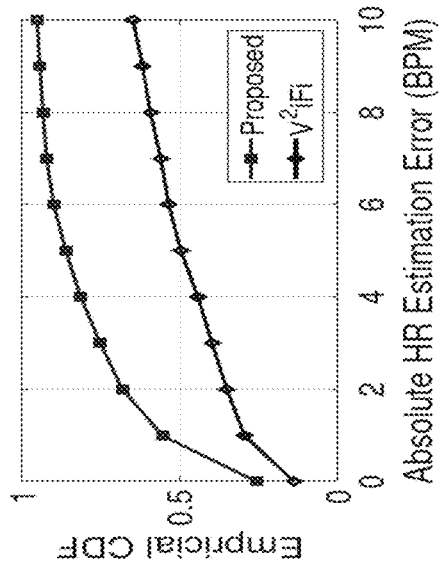
FIGS. 23A-23C illustrate an exemplary comparison of vital sign estimation performance between a disclosed system and another system, according to some embodiments of the present disclosure.
Figure 23B:
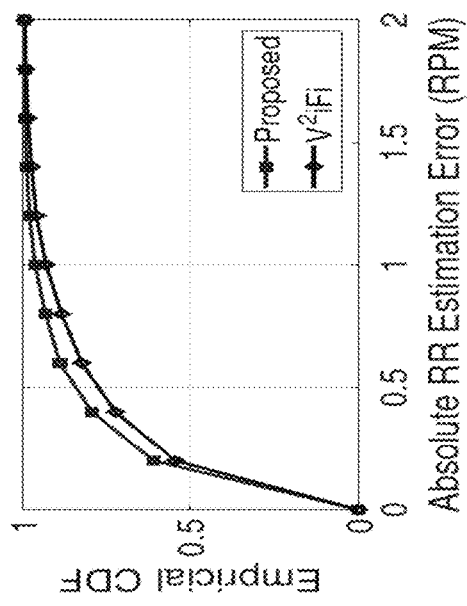
Figure 23C:
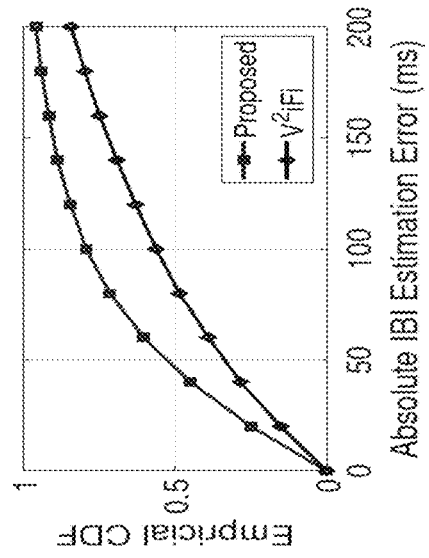

FIGS. 23A to 23C depict the overall performance of the disclosed system and $V^2$iFi. The experiments include road tests with different pavement conditions, device locations, as well as the controlled experiments with different motion types, including stationary, head motion, hand motion and back-and-forth torso motion for 4 different users. FIG. 23A plots the empirical Cumulative Distribution Function (CDF) of absolute RR estimation error, where the 90-percentile error for the disclosed system and $V^2$iFi are 0.64 RPM and 0.86 RPM respectively. The performance improvement is more significant for HR estimation, where the disclosed system achieves a median error of 0.82 BPM, and the median error of $V^2$iFi is 5.12 BPM, as shown in FIG. 23B. FIG. 23C shows the performance of IBI estimation for the two systems, where $V^2$iFi yields about 84 ms medium error, while the disclosed system achieves a medium error of 46 ms, outperforming $V^2$iFi by about 45.2%. The Bland-Altman plot is shown in FIG. 22, where the solid line shows the mean of the difference between the estimation and the ground-truth, and the dashed lines show the ±1.96 times of standard deviation of the difference. The estimation is nearly unbiased compared with the ground-truth.

Figure 24B:
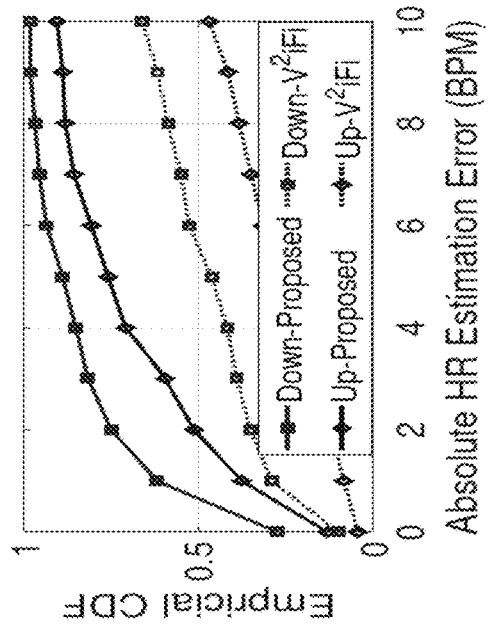
FIGS. 24A-24C illustrate vital sign estimation performance versus different device locations, according to some embodiments of the present disclosure.
Figure 24A:
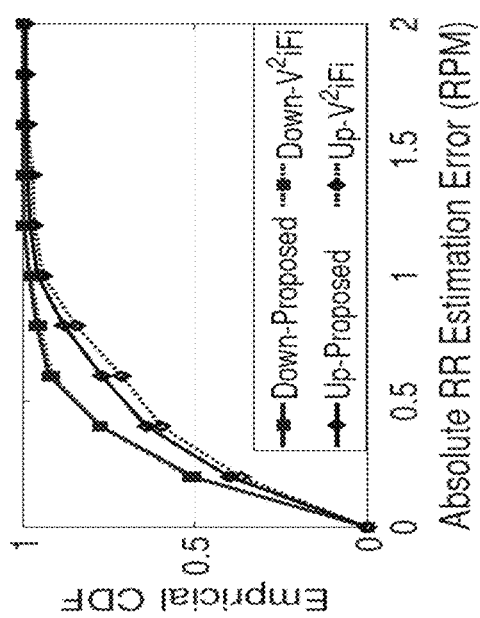
Figure 24C:
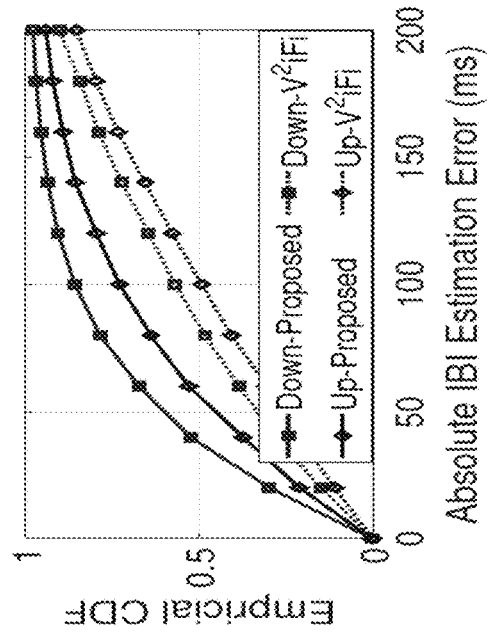

In some embodiments, one can investigate the impact of device location on vital signs estimation. The radar is placed at the top of windshield (denoted as "up"), and under the steering wheel (denoted as "down"). FIGS. 24A to 24C plot the CDF of the absolute error of RR, HR and IBI estimations, where lines marked with squares correspond to the "down" setting, and lines marked with diamonds correspond to the "up" setting.

It is shown that the "down" setting achieves better performance for all estimations. Specifically, for the disclosed system, the median error for RR, HR and IBI estimation are 0.2 RPM, 0.65 BPM and 38 ms respectively for the "down" setting. However, it increases to 0.28 RPM, 1.91 BPM and 56 ms for the "up" setting, corresponding to 40%, 193.85% and 47.37% performance degradation, respectively. One can observe the similar phenomenon in $V^2$iFi, where the median error for all the 3 metrics increases when the device is place as the "up" setting, as shown in dashed lines in FIGS. 24A to 24C. The reason is that when the device is mounted on the windshield, the vital bins mainly correspond to the chest, whereas, for the "down" setting, the vital bins mainly correspond to the lower chest and the abdomen. For the same scenario (e.g., car decelerates due to brake), severer motion will be involved in the upper chest than the abdomen. Therefore, the SNR of vital signals for the "down" setting is larger than the "up" setting. However, compared to the disclosed system, $V^2$iFi yields larger estimation error for all the 3 metrics, because it is less robust to noise.

Figure 25B:
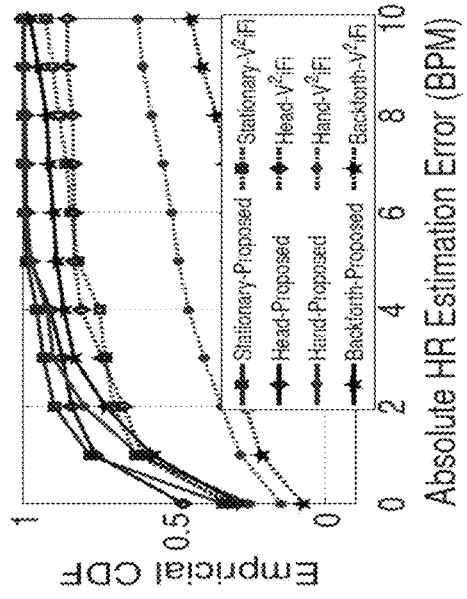
FIGS. 25A-25C illustrate vital sign estimation performance versus different motion types, according to some embodiments of the present disclosure.
Figure 25A:
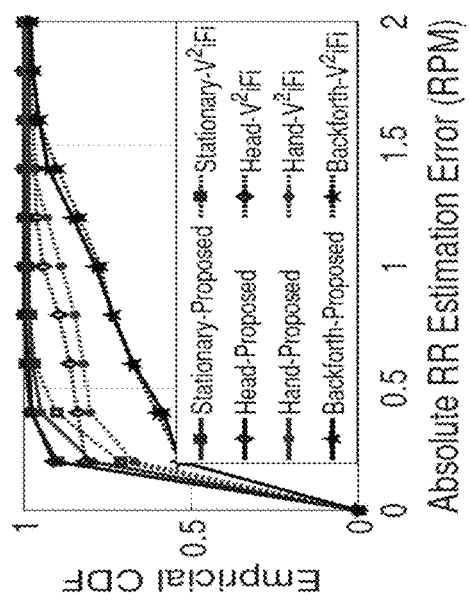
Figure 25C:
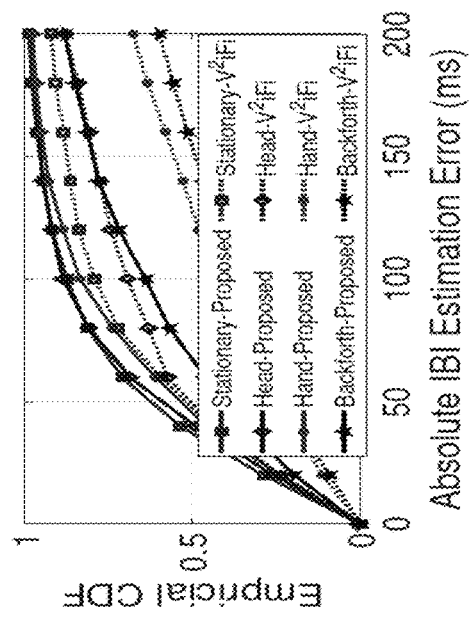

In some embodiments, as driving involves different kinds of motion of head, hand and body when looking at the side mirror, or controlling the steering wheel, etc., to better understand the impact of different motion types, one can conduct controlled experiments and analyze their corresponding impact, as shown in FIGS. 25A to 25C. During the experiment, drivers are asked to continuously perform specific type of motion in a parked car, including sitting stationary, head motion to check the surroundings, hand motion to operate steering wheel and randomly sway their body back-and-forth to emulate the body motion caused by acceleration and deceleration. Every data collection lasts for 2 minutes for both "up" setting and "down" setting, where 32 sets of data are collected for analysis.

FIG. 25A shows the CDF of RR estimation error with different motion types, where one can see that the median estimation error when driver performs head motion is nearly the same as the stationary case. The performance slightly degrade when the driver performs hand motion, where the median error increase from 0.11 RPM to 0.12 RPM compare to the stationary setting. However, for the large back-and-forth motion, one can observe a severe performance degradation, and its median error of RR estimation is 0.19 RPM, 72.73% worse than the stationary setting. Similar performance degradation can be observed in terms of HR and IBI estimation.

FIG. 25B shows that the median error of HR estimation increases from 0.35 BPM corresponding to the stationary setting to 0.68 BPM and 0.75 BPM when the driver performs hand and back-and-forth motion, respectively. As for IBI estimation, the median error when the driver performs sitting stationary, head motion, hand motion and random back-and-forth motion are 37 ms, 41 ms, 45 ms and 68 ms, respectively, as shown in FIG. 25C.

The estimation performance of $V^2$iFi are also plotted in dashed lines in FIGS. 25A to 25C, where the similar performance degradation can be observed. One can see that $V^2$iFi is more vulnerable to motion artifacts, and the performance degradation of hand and back-and-forth motion is more severe compared to the disclosed system. Specifically, one can see that the median error of HR estimation for the back-and-forth setting is larger than 10 BPM, which is almost useless for driver's HR estimation.

Figure 26A:
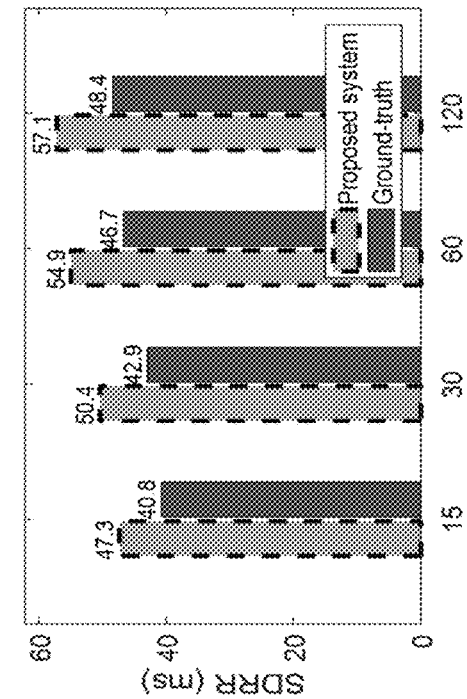
FIGS. 26A-26D illustrate an exemplary impact of window length to a vital sign monitoring system based on HRV metrics, according to some embodiments of the present disclosure.
Figure 26B:
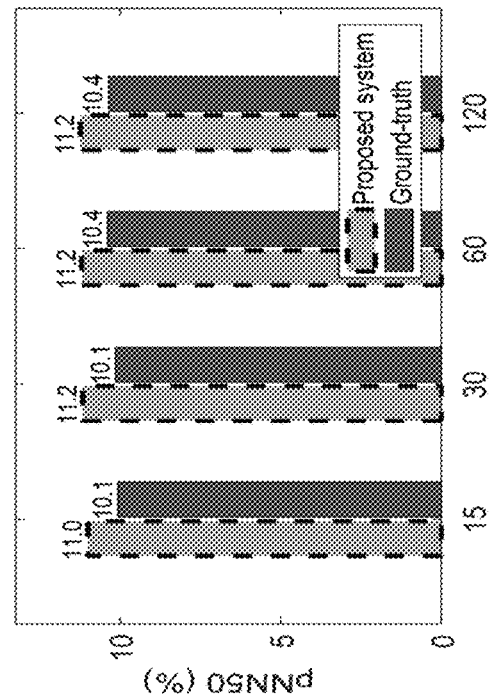
Figure 26C:
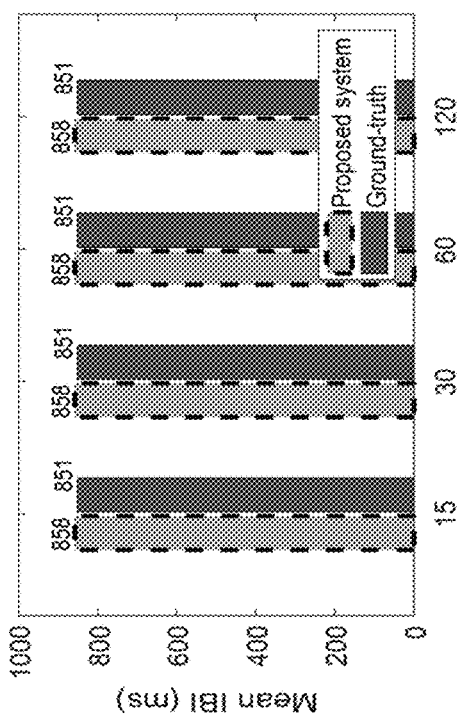
Figure 26D:
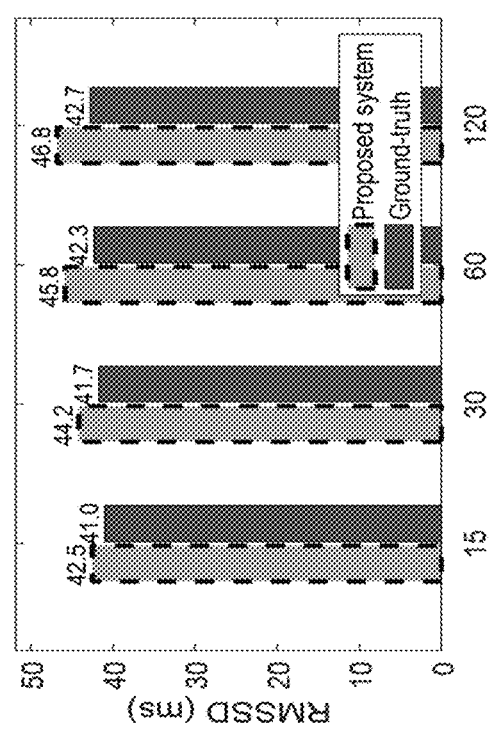

In some embodiments, one can investigate the impact of the window length on HRV calculation. Known that the HRV metrics can be derived from the IBI sequence, FIGS. 26A to 26D show 4 different commonly used HRV metrics with window length ranging from 15 s to 120 s. The mean of IBI and the standard deviation of the IBIs (SDRR) under different time window are shown in FIG. 26A and FIG. 26B, respectively. The Root-Mean-Square-of-Successive-Differences (RMSSD) is shown in FIG. 26C, which can be calculated by $$RMSSD = \sqrt{\frac{1}{N_{IBI} - 1} \sum_{i=2}^{N_{IBI}} (IBI(i) - IBI(i-1))^2}, \quad (46)$$

where $N_{IBI}$ is the total number of IBIs in the given time window. FIG. 26D shows the percentage of successive IBI that differ by more than 50 ms (pNN50), which can be calculated by $$pNN50 = \frac{\sum_{i=2}^{N_{IBI}} 1\{(IBI(i) - IBI(i-1)) > 50 \text{ ms}\}}{N_{IBI}}, \quad (47)$$

where $1\{\cdot\}$ is the indicator function. As shown in FIG. 26A, the mean of IBI barely changes over the window length. However, the other 3 metrics (i.e., SDRR, RMSSD and pNN50) increase with the window length for both estimation and ground-truth, as shown in FIGS. 26B to 26D. Furthermore, the estimation error of SDRR increases from 6.5 ms to 8.7 ms when the window length increases from 15 s to 120 s. Similar performance/trend can be observed in RMSSD, where the estimation error increases from 1.5 ms to 4.1 ms when the window length increases from 15 s to 120 s.

Figure 27:
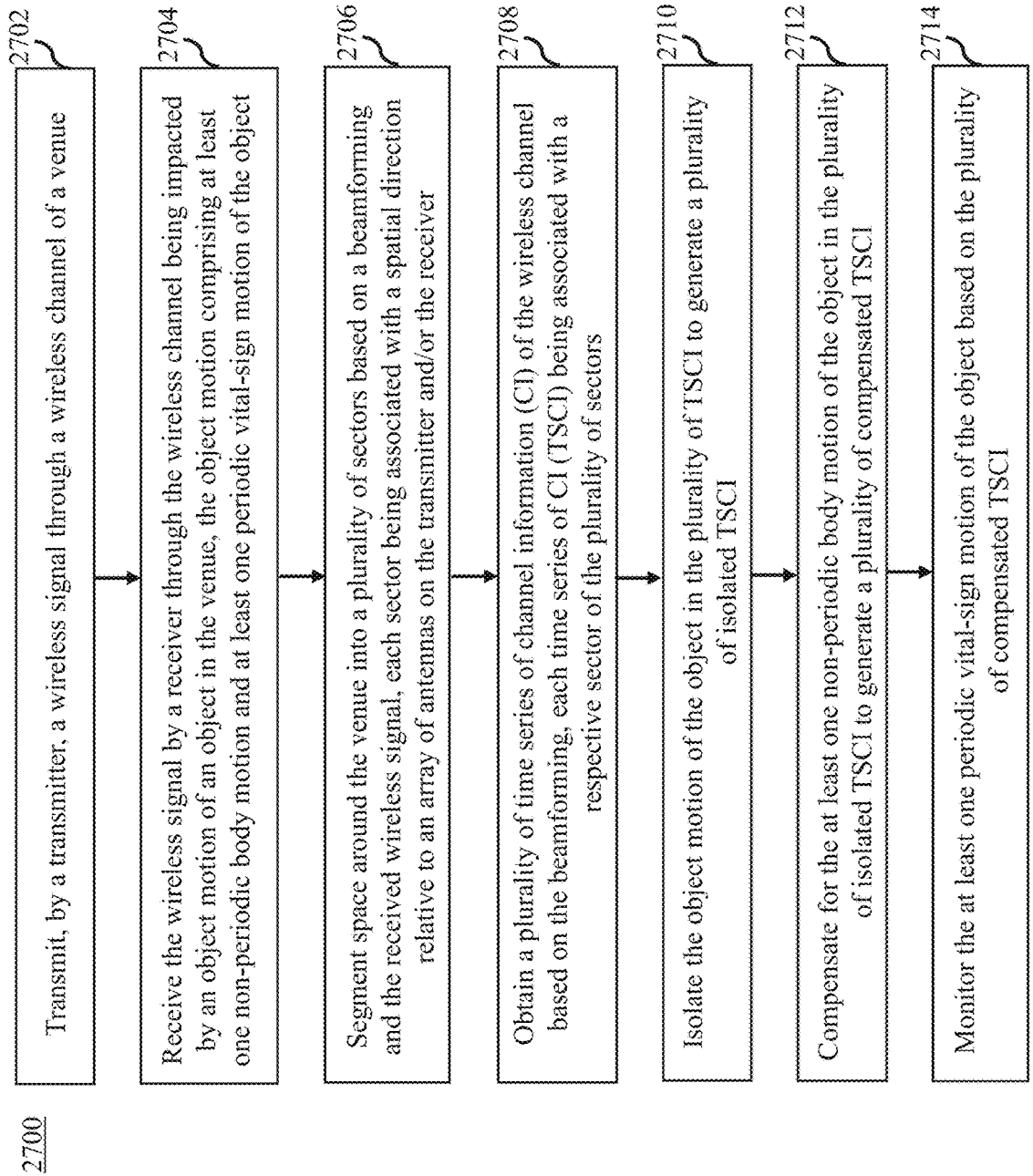
FIG. 27 illustrates a flow chart of an exemplary method for wireless vital sign monitoring, according to some embodiments of the present disclosure.

FIG. 27 illustrates a flow chart of an exemplary method 2700 for wireless vital sign monitoring, according to some embodiments of the present disclosure. At operation 2702, a wireless signal is transmitted by a transmitter through a wireless channel of a venue. At operation 2704, the wireless signal is received by a receiver through the wireless channel, wherein the wireless channel is being impacted by an object motion of an object in the venue, and wherein the object motion comprises at least one non-periodic body motion and at least one periodic vital-sign motion of the object. At operation 2706, the space around the venue is segmented into a plurality of sectors based on a beamforming and the received wireless signal, wherein each sector is associated with a spatial direction relative to an array of antennas on the transmitter and/or the receiver. At operation 2708, a plurality of time series of channel information (CI) of the wireless channel is obtained based on the beamforming, wherein each time series of CI (TSCI) is associated with a respective sector of the plurality of sectors. At operation 2710, the object motion of the object is isolated in the plurality of TSCI to generate a plurality of isolated TSCI. At operation 2712, the at least one non-periodic body motion of the object is compensated for in the plurality of isolated TSCI to generate a plurality of compensated TSCI. At operation 2714, the at least one periodic vital-sign motion of the object is monitored based on the plurality of compensated TSCI. The order of the operations in FIG. 27 may be changed according to various embodiments of the present teaching.

Thus, the present teaching discloses a novel system that can accurately detect driver's vital signs in the presence of practical driving motions using the reflections of RF signals off the human subject only. This is the first contact-free driver vital sign monitoring system that can detect driver's HRV considering driver's motion artifacts using commercial millimeter-wave (mmWave) radio. The system can detect the driver's vital signs without any prior calibration. A novel two-step motion compensation module is devised, where the motion artifact that is larger than the range-azimuth resolution is first eliminated by using the 2D cross correlation of the CIR. Then the fine motion artifact that is smaller than the range-azimuth bin is compensated by smoothing spline. Vital signals are obtained by jointly decomposing the phase measurements of all the reflections containing vital motions with several band-limited components, where the respiration and heartbeat are the component whose amplitude and center frequency satisfy the typical respiration and heartbeat signals.

For example, to locate the reflections from the driver, the system first performs beamforming to get the CIR with different range-azimuth bins, followed by a clutter removal module to remove the reflection from the background. Then the 2-dimensional correlation between different CIR samples have been used to eliminate large displacement caused by body roaming. Finer motion artifacts are further removed by the smoothing spline, which can accurate estimate motion artifacts without dedicated choose of hyper-parameter as in polynomial fitting. The displacement caused by respiration and heartbeat are then estimated by jointly optimizing the decomposition of vital signals in all vital bins, and the RR, HR and IBI can be extracted from the reconstructed respiration and heartbeat wave.

The system may be prototyped using a commercial mmWave radio to conduct experiments in the real driving scenario to evaluate the performance. Experimental results show that the disclosed system can estimate vital signs accurately with driving motion artifacts, outperforming the state-of-art works.

While average CIR in a time window is used to estimate the reflections from the background for clutter removal in some embodiments, other clutter removal method, such as the CIR difference in slow time domain, can be used in other embodiments. In some embodiments, a detrending method, such as the polynomial fitting, may be used to estimate the fine motion artifacts.

In some embodiments, a wireless vital sign monitoring method includes steps s1 to s8 as described below.

At step s1: capture CSI using multiple transmit (Tx) antenna and multiple receive (Rx) antenna.

At step s2: apply beamforming to get directional CSI (e.g. CIR). At step s3: remove clutters to reduce the impact of static reflecting objects, which includes steps s3a and s3b.

At step s3a: compute the background profile at each (theta, distance, time index) by taking average of the CIR over a time window. At step s3b: subtract the background profile from the CIR.

At step s4: determine the point-of-interest (PoI) (i.e., the (theta, distance)) corresponding to the reflections of the drive for each time window, which includes steps s4a to s4c. At step s4a: compensate large body movement which is larger than the range-azimuth resolution, including step s4a1 to calculate 2-dimension (2D) cross correlation between consecutive CIRs and step s4a2 to circularly shift the CIR at each time instance to the point (i.e., (theta, distance)) correspond to the maximum cross correlation. At step s4b: determine subject is present in the direction if the time-averaged magnitude response is greater than a threshold T1, wherein the threshold T1 may be a 2-dimensional CFAR filtering of CIR magnitude |h| in theta and distance direction. At step s4c: compensate fine body motion which is smaller than the range-azimuth resolution, wherein the fine body motion may be estimated by the smoothing spline of the phase measurement corresponding to the reflection off the driver.

At step s5: determine the PoI containing vital motions, including step s5a, for each PoI, compute the ACF of the phase and find significant feature point (e.g. first peak) P1, and step s5b, classify the PoI as the vital bin if P1 is greater than a threshold T2.

At step s6: extract the respiration signal and heartbeat signal by jointly decomposing the vital signal in all vital bins with a few band-limited signals, which includes steps s6a to s6c.

At step s6a: given a default setting of component number K and the parameter $\alpha$ for balancing, the bandwidth constraint and data fidelity, alternatively optimize the components and their center frequencies. At step s6b: check whether there is a component corresponding to respiration by some features, wherein the component corresponds to respiration wave if the amplitude of the signal locate in range [T3, T4], and its center frequency should locate in range [T5, T6]. At step s6c: check whether there is a component corresponding to heartbeat by some features, wherein the component corresponds to heartbeat wave if the amplitude of the signal locate in range [T7, T8], and its center frequency should locate in range [T9, T10].

At step s7: reconstruct respiration wave and heartbeat wave by averaging the respiration and heartbeat wave over all the vital bins, wherein the reconstructed respiration and heartbeat signal may be further normalized by using their envelope to reduce the noise.

At step s8: calculate vital signs by using the reconstructed vital signals, which includes steps s8a to s8c. At step s8a: calculate the respiration rate (e.g., first peak location of the ACF). At step s8b: calculate the heart rate (e.g., highest peak of the spectrum in range [T9, T10]). At step s8c: identify the exact time of each heartbeat and then calculate the inter-beat intervals to estimate heart rate variability (HRV), wherein the exact time of each heartbeat can be identified by several ways, e.g., identify the peaks of the heartbeat waves or identify the zero-crossing points.

The following numbered clauses provide examples for vital sign monitoring based on wireless beamforming.

Clause A1. A method/device/system/software of a wireless beamforming vital sign monitoring system, comprising: receiving a wireless signal by a Type 2 heterogeneous wireless device, wherein the wireless signal is transmitted to the Type 2 device by a Type 1 heterogeneous wireless device through a wireless multipath channel of a venue, wherein at least one of the Type1 device and the Type2 device comprises an array of antennas for the transmission or reception of the wireless signal, wherein the wireless multipath channel is impacted by an object motion of an object in the venue, wherein the object motion comprises a non-periodic body motion of the object and at least one periodic vital-sign motion of the object; segmenting the space into a plurality of sectors based on a beamforming and the received wireless signal using a processor, a memory and a set of instructions, each sector being associated with a spatial direction relative to the array of antenna; obtaining a plurality of time series of channel information (CI) of the wireless multipath channel based on the beamforming, each time series of CI (TSCI) being associated with a respective sector; isolating the object motion of the object in the plurality of TSCI; compensating for the non-periodic body motion of the object in the plurality of the isolated TSCI; monitoring the at least one periodic vital-sign motion of the object based on the plurality of compensated TSCI.

Step s3 may be reflected in the following Clause According to some embodiments. Clutter removal to remove effect of background of the venue to isolate the object motion of the object in each TSCI. Clutter removal is achieved by subtracting an average of past few CSI from current CSI. Assuming the object (person) is moving around randomly, the effect of the object motion (especially for the periodic vital-sign motion) tends to cancel itself in the averaging. Thus the averaging is an estimation of the background CSI. The subtraction is a kind of filtering (MA filtering).

Clause A2. The method/device/system/software of the wireless vital sign monitoring system of Clause A1, further comprising: filtering each TSCI to isolate the object motion of the object in the TSCI.

Clause A3. The method/device/system/software of the wireless vital sign monitoring system of Clause A2, further comprising: wherein the filter is one of: a moving-average (MA) filter, an autoregressive (AR) filter, or an autoregressive-moving-average (ARMA) filter.

Clause A4. The method/device/system/software of the wireless vital sign monitoring system of Clause A2, further comprising: wherein the filter computes a filtered CI by subtracting a weighted average of a number of past CI from a current CI.

Step s4 includes steps s4a, s4b and s4c, and may be reflected in the following Clause According to some embodiments. Step s4a computes cross correlation and shift consecutive CIR to compensate for large body movement. Shifting a first CI w.r.t. a second CI to compensate large body movement during the time duration between the first CI and the second CI.

Clause A5. The method/device/system/software of the wireless vital sign monitoring system of Clause A2, further comprising: shifting a first CI of a first TSCI; replace a second CI of a second TSCI with the shifted first CI to compensate for a large non-periodic body motion of the object.

According to some embodiments, the following Clause A may reflect computing cross correlation between first CI and second CI, and finding max point to find the shift amount.

Clause A6. The method/device/system/software of the wireless vital sign monitoring system of Clause A5, further comprising: wherein both the first CI and the second CI are associated with a common time stamp; determining a third CI of the second TSCI as a reference CI, wherein the third CI is temporally adjacent to the common time stamp of both the first CI and the second CI; for each of the plurality of TSCI: computing a respective cross correlation function between the temporal profile of the reference CI and the temporal profile of a respective CI of the respective TSCI, wherein the respective CI is associated with the common time stamp, computing a respective maximum point of the respective cross correlation function, computing a shift amount; computing a dominant maximum point among all the maximum points; determining the TSCI associated with the dominant maximum point as the first TSCI; shifting the temporal profile of the first CI of the first TSCI by an amount equal to a time shift associated with the dominant maximum point; replacing the second CI of the second TSCI by the shifted first CI.

According to some embodiments, the following Clause may reflect a special case when object body moves in radial direction (or radial body motion, i.e. no change in direction/sector, with change in distance). Only one TSCI is involved.

Clause A7. The method/device/system/software of the wireless vital sign monitoring system of Clause A5, further comprising: wherein the first TSCI and the second TSCI are a common TSCI; wherein the first CI is the second CI; wherein each CI comprises a temporal profile; wherein shifting the first CI is to shift the temporal profile of the first CI; computing a cross correlation function between the temporal profile of first CI and the temporal profile of a third CI of the common TSCI, wherein the third CI is temporally adjacent to the first CI; computing a maximum point of the cross correlation function; shifting the temporal profile of the first CI by an amount equal to a time shift associated with the maximum point; replacing the first CI of the first TSCI by the shifted fast CI.

Clause A8. The method/device/system/software of the wireless vital sign monitoring system of Clause A5, further comprising: shifting the fast CI using one of: circular shifting, or non-circular shifting.

Step s4b may be reflected in the following Clause according to some embodiments to use smoothing spline to compensate for small body movement.

Clause A9. The method/device/system/software of the wireless vital sign monitoring system of Clause A5, further comprising: for each of the plurality of TSCI: computing a magnitude feature of a weighted average of the respective CI of the respective TSCI in a time window, associating the respective TSCI, and a respective associated sector, with the object if the magnitude feature is greater than a threshold.

Step s4c may be reflected in the following Clause according to some embodiments to use smoothing spline to compensate for small body movement.

Clause A10. The method/device/system/software of the wireless vital sign monitoring system of Clause A9, further comprising: computing at least one time series of CI feature (CIF), each time series of CIF (TSCIF) associated with a respective TSCI associated with the object with each of its CIF being a feature of a respective CI of the respective TSCI; computing an estimate of a small non-periodic body motion of the object based on a smoothing spline; subtracting the estimate from the TSCIF to compensate for a small non-periodic body motion of the object.

Clause A11. The method/device/system/software of the wireless vital sign monitoring system of Clause A10, further comprising: wherein the feature of a CI comprises at least one of: a phase, a magnitude, a function of phase, a function of magnitude, a function of phase and magnitude, or the CI.

Step s5 may be reflected in the following Clause according to some embodiments to identify vital-sign bin/sector.

Clause A12. The method/device/system/software of the wireless vital sign monitoring system of Clause A10, further comprising: classifying a sector as a vital-sign sector based on the associated TSCIF, wherein the vital-sign sector associated with the at least one periodic vital-sign motion of the object.

Clause A13. The method/device/system/software of the wireless vital sign monitoring system of Clause A12, further comprising: computing an autocorrelation function (ACF) of each TSCIF; computing a second feature of the ACF; classifying the sector associated with the TSCI associated with the TSCIF as a vital-sign sector if the second feature exceeds is threshold.

Clause A14. The method/device/system/software of the wireless vital sign monitoring system of Clause A13, further comprising: wherein the second feature comprises at least one of: a maximum point, a local maximum point, a first positive local maximum point, a second local maximum point, a global maximum point, a magnitude of a maximum point, a time associated with a maximum point, a timing associated with a maximum point, a minimum point, a local minimum point, a first positive local minimum point, a second local minimum point, a global minimum point, a magnitude of a minimum point, a time associated with a minimum point, a timing associated with a minimum point, a zero-crossing point, a first positive zero-crossing point, a second positive zero-crossing point, a time associated with a zero-crossing point, a time duration between two zero-crossing points, or a timing associated with a zero-crossing point.

Step s6a may be reflected in the following Clause According to some embodiments to decompose phase of TSCI into a sum of breathing signal and a heart-beat signal.

Clause A15. The method/device/system/software of the wireless vital sign monitoring system of Clause A12, further comprising: wherein there is at least one vital-sign section; decomposing each TSCIF associated with a respective vital-sign section into at least one respective periodic component, each periodic component corresponding to a periodic vital-sign motion of the object, wherein each periodic component is associated with a respective frequency.

Clause A16. The method/device/system/software of the wireless vital sign monitoring system of Clause A15, further comprising: decomposing each TSCIF into the at least one respective periodic component based on an iterative optimization.

Step s6b and s6c may be reflected in the following Clause According to some embodiments about amplitude range and frequency range constraint.

Clause A17. The method/device/system/software of the wireless vital sign monitoring system of Clause A15, further comprising: wherein each of the at least one respective periodic component is constrained to have at least one of: a respective frequency within a respective frequency range, or a respective amplitude within a respective amplitude range.

Clause A18. The method/device/system/software of the wireless vital sign monitoring system of Clause A17, further comprising: wherein each of the at least one respective periodic component is associated with a respective likelihood function within the respective frequency range.

Step s7 may be reflected in the following Clause According to some embodiments to aggregate multiple vital-sign sector by averaging them.

Clause A19. The method/device/system/software of the wireless vital sign monitoring system of Clause A15, further comprising: computing at least one aggregate periodic component, each aggregate periodic component comprising a weighted average of the respective decomposed periodic components associated with the at least one vital-sign sector; monitoring each periodic vital-sign motion by analyzing the corresponding aggregate periodic component.

Step s8 may be reflected in the following Clause According to some embodiments to compute various statistics/analytics.

Clause A20. The method/device/system/software of the wireless vital sign monitoring system of Clause A19, further comprising: analyzing an aggregate periodic component by computing at least one of: an instantaneous frequency, instantaneous period, instantaneous timing, vital sign timing, maximum, minimum, zero-crossing, instantaneous vital sign beat, instantaneous vital-sign interval, instantaneous beat interval between adjacent beat, average, average frequency, average period, average interval, moving average, statistics, statistics of the frequency, statistics of the period, statistics of the interval, mean, median, mode, variance, standard deviation, variation, derivative, slope, total variation, absolute variation, square variation, spread, dispersion, variability, deviation, absolute deviation, square deviation, total deviation, divergence, range, interquartile range, skewness, kurtosis, L-moment, coefficient of variation, quartile coefficient of dispersion, mean absolute difference, Gini coefficient, relative mean difference, median absolute deviation, average absolute deviation, coefficient of dispersion, entropy, variance-to-mean ratio, maximum-to-minimum ratio, variation measure, regularity measure, similarity measure, likelihood, probability distribution function, histogram, sample distribution, moment generating function, expected value, expected function, correlation, correlation of two CI, correlation of two DI, correlation coefficient, correlation indicator, autocorrelation, a feature of autocorrelation function (ACF), cross correlation, inner product, dot product, outer product, covariance, auto-covariance, cross covariance, discrimination score, similarity score, similarity measure, similarity between two CI, similarity between two CI, similarity between two vectors of CI, similarity between two windows of CI, similarity between two windows of CI with unequal window length, similarity between two DI, similarity between two DI, similarity between two vectors of DI, similarity between two windows of DI, similarity between two windows of DI with unequal window length, distance, distance score, distance measure between two CI, distance measure between two vectors of CI, distance measure between two windows of CI, distance measure between two windows of CI aligned and mapped, distance measure between two windows of CI aligned using dynamic time warping (DTW), distance measure between two DI, distance measure between two vectors of DI, distance measure between two windows of DI, distance measure between two windows of DI aligned and mapped, distance measure between two windows of DI aligned using dynamic time warping (DTW), Euclidean distance, absolute distance, L-1 distance, L-2 distance, L-k distance, weighted distance, graph distance, distance metric, norm, L-1 norm, L-2 norm, L-k norm, location, localization, location coordinate, change in location, position, map position, height, horizontal location, vertical location, distance, displacement, speed, acceleration, rotational speed, rotational acceleration, direction, angle of motion, azimuth, direction of motion, rotation, path, deformation, transformation, shrinking, expanding, positional characteristics, gait, gait cycle, gesture, handwriting, head motion, mouth motion, hand motion, leg motion, body motion, heart motion, internal organ motion, tool motion, machine motion, complex motion, combination of multiple motions, motion trend, repeatedness, periodicity, pseudo-periodicity, impulsiveness, sudden-ness, fall-down occurrence, recurrence, transient event, behavior, transient behavior, period, time trend, temporal profile, temporal characteristics, occurrence, time, timing, starting time, initiating time, ending time, duration, history, motion classification, motion type, change, temporal change, frequency change, CI change, DI change, timing change, gait cycle change, measure of at least one of: repeatedness, periodicity, measure of variability, frequency spectrum, frequency characteristics, frequency, presence, absence, proximity, approaching, receding, object identifier, object composition, mouth-related rate, eye-related rate, walking rate, breathing rate, heart rate, tidal volume, depth of breath, inhale time, exhale time, inhale time to exhale time ratio, airflow rate, heart beat-to-beat interval, heart rate variability, motion detection statistics, motion identification statistics, motion recognition statistics, signal statistics, signal dynamics, anomaly, parameter, motion magnitude, motion phase, motion signal transformation, motion feature, presence of object, absence of object, entrance of object, exit of object, change of object, motion cycle, motion count, gait cycle, motion rhythm, deformation motion, size, length, area, volume, capacity, shape, form, tag, starting/initiating location, ending location, starting/initiating quantity, ending quantity, event occurrence, event statistics, fall-down event, security event, accident event, home event, office event, factory event, warehouse event, manufacturing event, assembly line event, maintenance event, vehicle-related event, navigation event, tracking event, door event, door-open event, door-close event, window event, window-open event, window-close event, repeatable event, one-time event, consumed quantity, unconsumed quantity, state, physical state, health state, well-being state, emotional state, mental state, another event, analytics, or output responses.

The features described above may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., C, Java), including compiled or interpreted languages, and it may be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data.

Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

While the present teaching contains many specific implementation details, these should not be construed as limitations on the scope of the present teaching or of what may be claimed, but rather as descriptions of features specific to particular embodiments of the present teaching. Certain features that are described in this specification in the context of separate embodiments may also be implemented in combination in a single embodiment. Conversely, various features that are described in the context of a single embodiment may also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Particular embodiments of the subject matter have been described. Any combination of the features and architectures described above is intended to be within the scope of the following claims. Other embodiments are also within the scope of the following claims. In some cases, the actions recited in the claims may be performed in a different order and still achieve desirable results. In addition, the processes depicted in the accompanying figures do not necessarily require the particular order shown, or sequential order, to achieve desirable results. In certain implementations, multitasking and parallel processing may be advantageous.

We claim:

1. A system for vital sign monitoring based on wireless beamforming, comprising:
   a transmitter configured to transmit a wireless signal through a wireless channel of a venue;
   a receiver configured to receive the wireless signal through the wireless channel that is being impacted by an object motion of an object in the venue, wherein
      at least one of the transmitter or the receiver comprises an array of antennas used to transmit or receive the wireless signal,
      the object motion comprises at least one non-periodic body motion of the object and at least one periodic vital-sign motion of the object; and
   a processor configured for:
      segmenting space around the venue into a plurality of sectors based on a beamforming and the received wireless signal, wherein each sector of the plurality of sectors is associated with a spatial direction relative to the array of antennas,
      obtaining a plurality of time series of channel information (CI) of the wireless channel based on the beamforming, wherein each time series of CI (TSCI) of the plurality of TSCI is associated with a respective sector of the plurality of sectors,
      isolating the object motion of the object in the plurality of TSCI to generate a plurality of isolated TSCI,
      compensating for the at least one non-periodic body motion of the object in the plurality of isolated TSCI to generate a plurality of compensated TSCI, wherein the compensating comprises:
         determining a first CI of a first TSCI in the plurality of isolated TSCI,
         determining a second CI and a third CI of a second TSCI in the plurality of isolated TSCI, wherein the first CI and the second CI are associated with a common time stamp, wherein the third CI is temporally adjacent to the common time stamp,
         computing a cross correlation function between a temporal profile of the first CI and a temporal profile of the third CI,
         computing a maximum point of the cross correlation function, computing a best shifting amount for the temporal profile of the first CI with respect to the third CI based on the maximum point of the cross correlation function, computing a shifted first CI by shifting the temporal profile of the first CI based on the best shifting amount, and replacing the second CI with the shifted first CI, and monitoring the at least one periodic vital-sign motion of the object based on the plurality of compensated TSCI.

2. The system of claim 1, wherein isolating the object motion of the object comprises:

filtering each TSCI of the plurality of TSCI based on a filter to isolate the object motion of the object in the TSCI.

3. The system of claim 2, wherein the filter is one of: a moving-average (MA) filter, an autoregressive (AR) filter, or an autoregressive-moving-average (ARMA) filter.

4. The system of claim 3, wherein filtering each TSCI comprises:

subtracting a weighted average of a number of past CI from a current CI in the TSCI to generate a filtered CI.

5. The system of claim 1, wherein a first non-periodic body motion of the object is larger than a range-azimuth resolution.

6. The system of claim 1, wherein compensating for the at least one non-periodic body motion of the object further comprises:

determining the third CI of the second TSCI as a reference CI;

for each respective TSCI of the plurality of isolated TSCI:

determining a respective candidate first CI of the respective TSCI, wherein the second CI and the candidate first CI are associated with the common time stamp, computing a respective cross correlation function between a temporal profile of the reference CI and a temporal profile of a respective candidate first CI of the respective TSCI, and computing a respective maximum point of the respective cross correlation function;

computing a dominant maximum point among all of the maximum points;

determining the isolated TSCI associated with the dominant maximum point as the first TSCI;

determining the respective candidate first CI associated with the dominant maximum point as the first CI; and computing the best shifting amount for the temporal profile of the first CI based on a time shift associated with the dominant maximum point.

7. The system of claim 1, wherein:

the first TSCI and the second TSCI are a common TSCI;

the first CI is the second CI;

each CI comprises a temporal profile;

shifting the first CI comprises shifting the temporal profile of the first CI; and compensating for the at least one non-periodic body motion of the object further comprises:

computing a cross correlation function between the temporal profile of the first CI and the temporal profile of a third CI of the common TSCI, wherein the third CI is temporally adjacent to the first CI, computing a maximum point of the cross correlation function, shifting the temporal profile of the first CI by an amount equal to a time shift associated with the maximum point, and replacing the first CI of the first TSCI by the shifted first CI.

8. The system of claim 1, wherein:

the first CI is shifted using one of: circular shifting or non-circular shifting; and compensating for the at least one non-periodic body motion of the object comprises:

for each respective TSCI of the plurality of TSCI, computing a magnitude feature of a weighted average of a respective CI of the respective TSCI in a time window, and for each respective TSCI of the plurality of TSCI, associating the respective TSCI and a respective associated sector with the object when the magnitude feature is greater than a threshold.

9. The system of claim 8, wherein compensating for the at least one non-periodic body motion of the object further comprises:

computing at least one time series of CI feature (CIF), wherein each respective time series of CIF (TSCIF) of the at least one TSCIF is associated with a corresponding TSCI associated with the object, each CIF of the respective TSCIF is a feature of a respective CI of the corresponding TSCI;

computing an estimate of a second non-periodic body motion of the object based on a smoothing spline, wherein the second non-periodic body motion is smaller than the range-azimuth resolution; and subtracting the estimate from the at least one TSCIF to compensate for the second non-periodic body motion of the object.

10. The system of claim 8, wherein the feature of the respective CI comprises at least one of: a phase, a magnitude, a function of phase, a function of magnitude, or a function of phase and magnitude, of the respective CI.

11. The system of claim 10, wherein monitoring the at least one periodic vital-sign motion of the object comprises:

classifying a particular sector among the plurality of sectors as a vital-sign sector based on the at least one TSCIF, wherein the vital-sign sector is associated with the at least one periodic vital-sign motion of the object.

12. The system of claim 11, wherein classifying the sector comprises:

computing at least one autocorrelation function (ACF) based on the at least one TSCIF, each ACF being an ACF of a respective TSCIF associated with a respective TSCI of a respective sector;

computing at least one feature point of the at least one ACF, each feature point being of a respective ACF associated with a respective sector; and classifying the particular sector associated with a particular feature point as the vital-sign sector when the particular feature point exceeds a threshold.

13. The system of claim 12, wherein the feature point comprises at least one of:

a maximum point, a magnitude of a maximum point, a timing associated with a maximum point, a minimum point, a magnitude of a minimum point, a timing associated with a minimum point, a zero-crossing point, a time duration between two zero-crossing points, or a timing associated with a zero-crossing point.

14. The system of claim 13, wherein monitoring the at least one periodic vital-sign motion of the object further comprises:
decomposing each TSCIF associated with any vital-sign sector into at least one respective periodic component, wherein each periodic component corresponds to a respective periodic vital-sign motion of the object, wherein each periodic component is associated with a respective frequency.

15. The system of claim 14, wherein each TSCIF is decomposed into the at least one respective periodic component based on an iterative optimization.

16. The system of claim 15, wherein each of the at least one respective periodic component is constrained to have at least one of:
a respective frequency within a respective frequency range, or
a respective amplitude within a respective amplitude range.

17. The system of claim 16, wherein each of the at least one respective periodic component is associated with a respective likelihood function within the respective frequency range.

18. The system of claim 17, wherein monitoring the at least one periodic vital-sign motion of the object further comprises:
computing at least one aggregate periodic component based on the at least one periodic component of a plurality of TSCIF associated with any vital-sign sector, wherein each of the at least one aggregate periodic component comprises a weighted average of the respective periodic components associated with the plurality of TSCIF; and
monitoring each periodic vital-sign motion based on analyzing an aggregate periodic component corresponding to the periodic vital-sign motion, wherein the aggregate periodic component is analyzed based on at least one of: an instantaneous frequency, instantaneous period, vital sign timing, average, range, histogram, variance, correlation, variability, deviation, or periodicity.

19. A method of a vital sign monitoring system, comprising:
transmitting, by a transmitter, a wireless signal through a wireless channel of a venue;
receiving, by a receiver, the wireless signal through the wireless channel that is being impacted by an object motion of an object in the venue, wherein
at least one of the transmitter or the receiver comprises an array of antennas used to transmit or receive the wireless signal,
the object motion comprises at least one non-periodic body motion of the object and at least one periodic vital-sign motion of the object;
segmenting space around the venue into a plurality of sectors based on a beamforming and the received wireless signal, wherein each sector of the plurality of sectors is associated with a spatial direction relative to the array of antennas;
obtaining a plurality of time series of channel information (CI) of the wireless channel based on the beamforming, wherein each time series of CI (TSCI) of the plurality of TSCI is associated with a respective sector of the plurality of sectors;
isolating the object motion of the object in the plurality of TSCI to generate a plurality of isolated TSCI;
compensating for the at least one non-periodic body motion of the object in the plurality of isolated TSCI to generate a plurality of compensated TSCI, wherein the compensating comprises:
determining a first CI of a first TSCI in the plurality of isolated TSCI,
determining a second CI and a third CI of a second TSCI in the plurality of isolated TSCI, wherein the first CI and the second CI are associated with a common time stamp, wherein the third CI is temporally adjacent to the common time stamp,
computing a cross correlation function between a temporal profile of the first CI and a temporal profile of the third CI,
computing a maximum point of the cross correlation function,
computing a best shifting amount for the temporal profile of the first CI with respect to the third CI based on the maximum point of the cross correlation function,
computing a shifted first CI by shifting the temporal profile of the first CI based on the best shifting amount, and
replacing the second CI with the shifted first CI; and
monitoring the at least one periodic vital-sign motion of the object based on the plurality of compensated TSCI.

20. A wireless device of a vital sign monitoring system, comprising:
a processor;
a memory communicatively coupled to the processor; and
a receiver communicatively coupled to the processor, wherein:
an additional wireless device of the vital sign monitoring system is configured for transmitting a wireless signal through a wireless channel of a venue,
the receiver is configured for receiving the wireless signal through the wireless channel that is being impacted by an object motion of an object in the venue,
at least one of the transmitter or the receiver comprises an array of antennas used to transmit or receive the wireless signal,
the object motion comprises at least one non-periodic body motion of the object and at least one periodic vital-sign motion of the object, and
the processor is configured for:
segmenting space around the venue into a plurality of sectors based on a beamforming and the received wireless signal, wherein each sector of the plurality of sectors is associated with a spatial direction relative to the array of antennas,
obtaining a plurality of time series of channel information (CI) of the wireless channel based on the beamforming, wherein each time series of CI (TSCI) of the plurality of TSCI is associated with a respective sector of the plurality of sectors,
isolating the object motion of the object in the plurality of TSCI to generate a plurality of isolated TSCI,
compensating for the at least one non-periodic body motion of the object in the plurality of isolated TSCI to generate a plurality of compensated TSCI, wherein the compensating comprises:
determining a first CI of a first TSCI in the plurality of isolated TSCI,
determining a second CI and a third CI of a second TSCI in the plurality of isolated TSCI, wherein the first CI and the second CI are associated with a common time stamp, wherein the third CI is temporally adjacent to the common time stamp, computing a cross correlation function between a temporal profile of the first CI and a temporal profile of the third CI, computing a maximum point of the cross correlation function, computing a best shifting amount for the temporal profile of the first CI with respect to the third CI based on the maximum point of the cross correlation function, computing a shifted first CI by shifting the temporal profile of the first CI based on the best shifting amount, and replacing the second CI with the shifted first CI, and monitoring the at least one periodic vital-sign motion of the object based on the plurality of compensated TSCI.

* * * * *